US008008459B2

(12) United States Patent
Goldsmith et al.

(10) Patent No.: US 8,008,459 B2
(45) Date of Patent: Aug. 30, 2011

(54) CONCATEMERS OF DIFFERENTIALLY EXPRESSED MULTIPLE GENES

(75) Inventors: Neil Goldsmith, Oxford (GB); Alexandra M. P. Santana Sorensen, Holte (DK); Soren V. S. Nielsen, Allerod (DK); Michael Naesby, Valby (DK)

(73) Assignee: Evolva SA, Reinach (CH)

( * ) Notice: Subject to any disclaimer, the term of this patent is extended or adjusted under 35 U.S.C. 154(b) by 1490 days.

(21) Appl. No.: 10/466,959

(22) PCT Filed: Jan. 25, 2002

(86) PCT No.: PCT/DK02/00055
§ 371 (c)(1),
(2), (4) Date: Dec. 18, 2003

(87) PCT Pub. No.: WO02/059296
PCT Pub. Date: Aug. 1, 2002

(65) Prior Publication Data
US 2004/0110174 A1    Jun. 10, 2004

Related U.S. Application Data

(60) Provisional application No. 60/301,022, filed on Jun. 27, 2001.

(30) Foreign Application Priority Data

Jan. 25, 2001 (DK) ................................ 2001 00127

(51) Int. Cl.
*C07H 21/04* (2006.01)
*C12N 5/10* (2006.01)
*C12N 15/11* (2006.01)
*C12N 1/16* (2006.01)

(52) U.S. Cl. ................. 536/23.1; 435/325; 435/320.1; 435/254.2

(58) Field of Classification Search .................. None
See application file for complete search history.

(56) References Cited

U.S. PATENT DOCUMENTS

| | | |
|---|---|---|
| 4,464,472 A | 8/1984 | Carbon et al. |
| 4,870,013 A | 9/1989 | Gelfand et al. |
| 4,945,046 A | 7/1990 | Horii et al. |
| 5,035,996 A | 7/1991 | Hartley |
| 5,089,398 A | 2/1992 | Rosenberg et al. |
| 5,270,201 A | 12/1993 | Richards et al. |
| 5,316,922 A | 5/1994 | Brown et al. |
| 5,436,136 A | 7/1995 | Hinnen et al. |
| 5,559,027 A | 9/1996 | Filmus et al. |
| 5,641,661 A | 6/1997 | Kumagai et al. |
| 5,667,986 A | 9/1997 | Goodey et al. |
| 5,783,431 A | 7/1998 | Peterson et al. |
| 5,798,227 A | 8/1998 | Hoffman et al. |
| 5,824,485 A | 10/1998 | Thompson et al. |
| 5,837,458 A | 11/1998 | Minshull et al. |
| 5,877,018 A | 3/1999 | Filmus et al. |
| 5,888,732 A | 3/1999 | Hartley et al. |
| 5,952,195 A | 9/1999 | Nacken et al. |
| 5,958,672 A | 9/1999 | Short |
| 5,977,439 A | 11/1999 | Hamilton |
| 6,001,574 A | 12/1999 | Short et al. |
| 6,004,788 A | 12/1999 | Short |
| 6,025,155 A | 2/2000 | Hadlaczky et al. |
| 6,030,779 A | 2/2000 | Short |
| 6,054,267 A | 4/2000 | Short |
| 6,057,103 A | 5/2000 | Short |
| 6,072,050 A | 6/2000 | Bowen et al. |
| 6,077,697 A | 6/2000 | Hadlaczky et al. |
| 6,117,679 A | 9/2000 | Stemmer |
| 6,133,503 A | 10/2000 | Scheffler et al. |
| 6,136,567 A | 10/2000 | Duchars et al. |
| 6,165,793 A | 12/2000 | Stemmer |
| 6,174,673 B1 | 1/2001 | Short et al. |
| 6,268,140 B1 | 7/2001 | Stuart |

(Continued)

FOREIGN PATENT DOCUMENTS

EP      0329203      8/1989

(Continued)

OTHER PUBLICATIONS

Jeffrey L. Stein et al., Nucleotide sequence and expression of a deep-sea ribulose-1,5,-bisphosphate carboxylase gene cloned from a chemoautotropic bacterial endosymbiont, Proc. Natl. Acad. Sci. USA, vol. 87, pp. 8850-8854, Nov. 1990.

(Continued)

*Primary Examiner* — Michael Burkhart
(74) *Attorney, Agent, or Firm* — McDonnell Boehnen Hulbert & Berghoff LLP

(57) ABSTRACT

In the present invention are disclosed concatemers of concatenated expression cassettes and vectors that enable the synthesis of such concatemers. The concatemer comprises in the 5'→3' direction a cassette of nucleotide sequence of the general formula [rs2-SP-PR-X-TR-SP-rs1]n wherein rs1 and rs2 together denote a functional restriction site, SP individually denotes a spacer of at least two nucleotide bases, PR denotes a promoter, capable of functioning in a cell, X denotes an expressible nucleotide sequence, TR denotes a terminator, and SP individually denotes a spacer of at least two nucleotide bases, and n>/=2, and wherein at least a first cassette is different from a second cassette. The main purpose of these concatemers is the controllable and co-ordinated expression of large numbers of heterologous genes in a single host. Furthermore, the invention relates to a concatemer of cassettes of nucleotide sequences and a method for preparing the concatemers. In a further aspect, the invention relates to transgenic host cells comprising at least one concatemer according to the invention, as well as to a method for preparing the transgenic host cells. Finally, the invention relates to a vector comprising a cassette of nucleotides, a method for preparing said vector, a nucleotide library comprising at least two primary vectors each comprising a cassette of nucleotides, a method for preparing the library.

24 Claims, 13 Drawing Sheets

U.S. PATENT DOCUMENTS

| | | |
|---|---|---|
| 6,294,325 B1 | 9/2001 | Wetmur |
| 7,052,876 B1 | 5/2006 | Finney et al. |
| 7,105,297 B2 | 9/2006 | Minshull et al. |
| 2001/0041333 A1 | 11/2001 | Short et al. |
| 2002/0025517 A1 | 2/2002 | Minshull et al. |
| 2003/0175678 A1 | 9/2003 | Bowen et al. |
| 2004/0133941 A1 | 7/2004 | Bowen et al. |
| 2004/0241672 A1 | 12/2004 | Goldsmith et al. |
| 2005/0019924 A1 | 1/2005 | Hitzeman et al. |
| 2005/0158860 A1 | 7/2005 | Goldsmith et al. |
| 2005/0164162 A1 | 7/2005 | Sorensen et al. |
| 2006/0068472 A1 | 3/2006 | Caldwell et al. |
| 2006/0252156 A1 | 11/2006 | Goldsmith et al. |

FOREIGN PATENT DOCUMENTS

| | | |
|---|---|---|
| WO | 89/10566 | 11/1989 |
| WO | WO 91/00420 | 1/1991 |
| WO | 95/08647 | 3/1995 |
| WO | 95/11986 | 5/1995 |
| WO | WO 96/34112 | 10/1996 |
| WO | WO 9731118 A1 * | 8/1997 |
| WO | WO 97/35966 | 10/1997 |
| WO | WO 97/40183 | 10/1997 |
| WO | 97/44470 | 11/1997 |
| WO | WO 98/17811 | 4/1998 |
| WO | WO 98/31837 | 7/1998 |
| WO | 98/38490 | 9/1998 |
| WO | 98/41869 | 9/1998 |
| WO | 98/54339 | 12/1998 |
| WO | 98/58085 | 12/1998 |
| WO | WO 99/10539 | 3/1999 |
| WO | WO 99/45154 | 3/1999 |
| WO | 99/35260 | 7/1999 |
| WO | WO 00/04190 | 1/2000 |
| WO | 00/08212 | 2/2000 |
| WO | WO 00/06715 | 2/2000 |
| WO | 00/17643 | 3/2000 |
| WO | WO 00/12680 | 3/2000 |
| WO | WO 00/52180 | 9/2000 |
| WO | WO 00/53744 | 9/2000 |
| WO | WO 98/01573 | 9/2000 |
| WO | WO 00/58517 | 10/2000 |
| WO | WO 00/77262 | 12/2000 |
| WO | 01/32829 | 5/2001 |
| WO | WO 01/73000 | 10/2001 |
| WO | 02/059290 | 8/2002 |
| WO | 02/059296 | 8/2002 |
| WO | 02/059297 | 8/2002 |
| WO | 02/059330 | 8/2002 |
| WO | 03/062419 | 7/2003 |
| WO | 03/106639 | 12/2003 |
| WO | 2004/016791 | 2/2004 |

OTHER PUBLICATIONS

T. Lotan et al., Cloning and expression in *Escherichia coli* of the gene encoding β-C-4-oxygenase, that coverts β carotene to the ketocarotenoid canthaxanthin in *Haematococcus pluvialis*, FEBS letters 364, 1995, pp. 125-128.
J. Staudinger, Interactions among vertebrate helix-loop-helix proteins in yeast using the two-hybrid system., J Biol Chem. Mar. 5, 1993; 268(7): 4608-11. Abstract only.
Raphael Nir et al., Flow cytometry sorting of viable bacteria and yeasts according to β-galactosidase activity, Applied and environmental microbiology, Dec. 1990, p. 3861-3866, vol. 56, No. 12.
P. J. McCormack et al., Production of antibacterial compounds by phylloplane-inhabiting yeasts and yeastlike fungi, Applied and environmental microbiology, Mar. 1994, p. 927-931, vol. 60, No. 3.
Smith, et al., Constuction and Use of Signal Sequence Selection Vectors in *Escherichia coli* and *Bacillus subtilis*, Journal of Bacteriology, vol. 169, No. 7, pp. 3321-3328, Jul. 1987.
Leahy, et al., "Transcription from plasmid expression vectors is increased up to 14-fold when plasmids are transfected as concatermers", *Nucleic Acids Research*, vol. 25, No. 2, pp. 449-450, 1997.
Gift et al., "FACS-based isolation of slowly growing cells: Double encapsulation of yeast in gel microdrops," Nature Biotechnology, 14:884-887 (1996).
International Search Report for WO 2002/059290 mailed Dec. 23, 2002.
International Search Report for WO 2002/059296 mailed Oct. 23, 2002.
International Search Report for WO 2002/059297 mailed Jan. 15, 2003.
International Search Report for WO 2003/062419 mailed Jun. 11, 2003.
International Search Report for WO 2004/016791 mailed Dec. 5, 2003.
Pierce et al., "A positive selection vector for cloning high molecular weight DNA by the bacteriophage P1 system: Improved cloning efficacy," Proc. Natl. Acad. Sci. USA, 89:2056-2060 (1992).
Zhu et al., "Three-Color Flow Cytometry Analysis of Tricistronic Expression of eBFP, eGFP, and eYFP Using EMCV-IRES Linkages," Cytometry, 37:51-59 (1999).
Blattner et al., "The Complete Genome Sequence of *Escherichia coli* K-12," Science, 277:1453-1462 (Sep. 5, 1997).
Diatchenko et al., "Suppression subtractive hybridization: A method for generating differentially regulated or tissue-specific cDNA probes and libraries," PNAS, 93:6025-6030 (Jun. 1996).
Carninci et al., "Normalization and Subtraction of Cap-Trapper-Selected cDNAs to Prepare Full-Length cDNA Libraries for Rapid Discovery of New Genes," Genome Res., 10:1617-1630 (2000).
Wood et al., "Complementary DNA Coding Click Beetle Luciferases Can Elicit Bioluminescence of Different Colors," Science, 244:700-702 (May 12, 1989).
Sehested et al., "Chinese Hamster Ovary Cells Resistant to the Topoisomerase II Catalytic Inhibitor ICRF-159: A Typr49Phe Mutation Confers High-Level Resistance to Bisdioxopiperazines," Cancer Research, 58:1460-1468 (Apr. 1, 1998).
Weinshilbourn, R.M. et al., "Sulfotransferase molecular biology: cDNAs and genes," The FASEB Journal, 11:3-14 (Jan. 1997).
Bouska. et al., "Improving the In Vivo Duration of 5-Lipoxygenase Inhibitors—Application of an In Vitro Glucuronosyltransferase Assay," Drug Metab. Dispos., 25(9):1032-1038 (1997).
Burke et al., "Cloning of Large Segments of Exogenous DNA into Yeast by Means of Artificial Chromosome Vectors," Science, 236:806-812 (May 15, 1987).
Foster, Barbara et al., "Pharmacological Rescue of Mutant p53 Conformation and Function," Science, 286:2507-2510 (1999).
Bonaldo et al., "Normalization and Subtraction: Two Approaches to Facilitate Gene Discovery," Genome Research, 6:791-806 (1996).
Benderitter, M. et al., "Simultaneous analysis of radio-induced membrane alteration and cell viability by flow cytometry," Cytometry, 39(2):151-157 (2000).
Sears, D.D. et al., "An Implanted Recombination Hot Spot Stimulates Recombination and Enhances Sister Chromatid Cohesion of Heterologous YACs During Yeast Meiosis," Genetics, 138:1055-1065 (Aug. 26, 1994).
Dubois, R. et al., "Cyclooxygenase in biology and disease," Faseb J., 12:1063- 1073 (Sep. 1998).
Jordan, S.P. et al., "Activity and dimerization of human immunodeficiency virus protease as a function of solvent composition and enzyme concentration," J. Biol. Chem., 267(28):20028-20032 (Oct. 5, 1992).
Rao et al., "Choroid plexus epithelial expression of MDR1 P glycoprotein and multidrug resistance-associated protein contribute to the blood-cerebrospinal-fluid drug-permeability barrier," Proc. Natl. Acad. Sci., 96(7): 3900-3905 (Mar. 1999).
Salerno et al., "Differential transcriptional regulation of the apoA1 gene by retinoic acid receptor homo-and heterodimers in yeast," Nucleic Acids Res., 24(4):566-572 (1996).
Schinkel et al., "Normal viability and altered pharmacokinetics in mice lacking mdr1-type (drug-transporting) P-glycoproteins," Proc. Natl. Acad. Sci., 94: 4028-4033 (Apr. 1997).
Sive et al., "A simple subtractive hybridization technique employing photoactivatable biotin and phenol extraction," Nucleic Acid Res., 16:10937 (Sep. 29, 1988).
Smith et al., "Amplification of large artificial chromosomes," Proc. Natl. Acad. Sci., 87:8242-8246 (Nov. 1990).

Wasserman R. et al., "Use of Yeast in the Study of Anticancer Drugs Targeting DNA Topoisomerases: Expression of a Functional Recombinant Human DNA Topoisomerase IIα in Yeast," Cancer Research, 53:3591-3596 (Aug. 1, 1993).

Wijnholds J et al., "Multidrug resistance protein 1 protects the choroid plexus epithelium and contributes to the blood-cerebrospinal fluid barrier," J Clin Invest, 105(3): 279-85 (Feb. 2000).

Ziegler, J. et al., "Cancer and Arthritis Share Underlying Processes," J. Nat. Cancer Inst., 90(11):802-803 (1998).

Ihler, G.M., "Erythrocyte Carriers," Pharm. Ther., 20(2): 151-169 (1983).

Kunst et al., "The complete genome sequence of the Gram-positive bacterium *Bacillus subtilis*," Nature, 390:249-256 (Nov. 20, 1997).

Armitage, B., "Photocleavage of nucleic acids," Chem. Rev. 98:1171-1200 (1998).

Dervan, P.B. et al., "Sequence-specific DNA recognition by polyamides," Curr. Opin. Chem. Biol., 3:688-693 (Dec. 1, 1999).

Nielsen, P.E., "Peptide nucleic acid: a versatile tool in genetic diagnostic and molecular biology," Curr. Opin. Biotechnol., 12:16-20 (Feb. 1, 2001).

Bashkin, J.K., "Introduction to RNA/DNA Cleavage," Chem Rev, 98(3): 937-938 (Apr. 17, 1998).

Spingola, M. et al., "Genome-wide bioinformatic and molecular analysis of introns in *Saccharomyces cerevisiae*," RNA, 5(2):221-234 (1999).

Tsang et al., "Entrapment of Proteins, Viruses, Bacteria, and DNA in Erythrocytes during Endocytosis," Journal of Applied Biochemistry, 4:418-435 (1982).

Ali et al, "Normalisation of cereal endosperm EST libraries for structural and functional genomic analysis," Plant Mol. Biol. Reporter, 18:123-132 (Jun. 2000).

Metcalf et al., "Construction of new β-glucuronidase cassettes for making transcriptional fusions and their use with new methods for allele replacement," Gene, 129:17-25 (Jul. 15, 1993).

Sahar et al., "Flow cytometric analysis of entire microbial colonies," Cytometry, 15:213-221 (1994).

Murray et al.., "Construction of artificial chromosomes in yeast," Nature, 305:189-193 (Sep. 15, 1983).

Sauer, B., "[53] Manipulation of transgenes by site-specific recombination: Use of cre recombinase," Methods Enzymol., 225:890-900 (1993).

Landy, A., "Dynamic, Structural, and Regulatory Aspects of lambda Site-Specific Recombination," Ann. Rev. Biochem., 58:913-941 (Jul. 1989).

Hugerat Y. et al., "A Versatile Method for Efficient YAC Transfer between Any Two Strains," Genomics, 22 (1):108-117 (Jul. 1, 1994).

Curran, B.P. et al., "Protoplast Fusion in *Saccharomyces cerevisiae*," Methods Mol. Biol., Chapter 5, vol. 53:45-49 (1996).

An, G.H. et al., "Isolation and characterization of carotenoid hyperproducing mutants of yeast by flow cytometry and cell sorting," Biotechnology, 9:70-73 (Jan. 1991).

McCall, J. et al., "Pyrimidine and triazine 3-oxide sulfates: a new family of vasodilators," J. Med. Chem., 26:1791-1793 (1983).

Wittrup, K.D. et al., "Microencapsulation selection for isolation of yeast mutants with increased secretion of *Aspergillus awamori* glucoamylase," Biotechnolog. Bioeng., 42:351-356 (Jul. 1993).

Chen et al., "Inhibition of Fumarate Reductase in Leishmania major and L. donovani by Chalcones," Antimicrob. Agents Chemother., 45(7):2023-2029 (2001).

Raftogianis, R.B. et al., "Phenol sulfotransferase pharmacogenetics in humans: Association of common SULT1A1 alleles with TS PST phenotype," Biochem Biophys Res Commun. (BBRC), 239:298-304 (Oct. 9, 1997).

Radominska-Pandya, A. et al., "Structural and functional studies of UDP-glucuronosyltransferases," Drug Metab. Rev., 31:817-899 (Nov. 1999).

Karin, M., "The NF-kappa B activation pathway: its regulation and role in inflammation and cell survival," Cancer J Sci Am, 4:S92-9 (1998).

Barnes, Peter, "Nuclear factor-κB," Int. J. Biochem. Cell. Biol., 29(6):867-870 (Jun. 1997).

Handel, ML, "Transcription factors AP-1 and NFkB: where steroids meet the gold standard of anti-rheumatic drugs," Inflamm. Res., 46:282-286 (1997).

Malonne, H. et al., "DNA topoisomerase targeting drugs: mechanisms of action and perspectives," Anti-Cancer Drugs, 8(9):811-822 (Oct. 1997).

Nitiss et al, "Yeast Systems for Demonstrating the Targets of Antitopoisomerase II Agents," Methods in Molecular Biology, 95:315-327 (2001).

Inui K. et al., "Transepithelial transport of oral cephalosporins by monolayers of intestinal epithelial cell line Caco-2: specific transport systems in apical and basolateral membranes.," J. Pharmacol Exp Ther., 261:195-201 (Apr. 1992).

Lu, S. et al., "Effect of Subculturing on the Epithelial Properties of Caco-2 Cells as a Transport Model," Pharm. Res. 11:S-258 (Oct. 14, 1994).

Bjorge, S. et al., "Evidence for Glucuronide Conjugation of p-Nitrophenol in the Caco-2 Cell Model," Pharm Res., 8(11):1441-1443 (Nov. 1991).

Gottesman MM et al., "Biochemistry of Multidrug Resistance Mediated by the Multidrug Transporter," Ann. Rev. Biochem, 62: 385-427 (1993).

Kurelec, B. et al., "Distinct glutathione-dependent enzyme activities and a verapamil-sensitive binding of xenobiotics in a fresh-water mussel Anodonta cygnea," Biochem Biophys Res Comm, 164(2): 934-940 (Oct. 31, 1989).

Kurelec, B, "The multixenobiotic resistance mechanism in aquatic organisms," Crit Rev Toxicol, 22(1): 23-43 (1992).

Ohgiya, S. et al., "Cloning of Human Cytochrome P-450 cDNA and its Expression in *Saccharomyces cerevisiae*," Biochem Int., 18(2):429-438 (Feb. 1989).

Winters, D.K., "Expression of a catalytically active human cytochrome P-4502E1 in *Escherichia coli*," Biochim Biophys Acta, 1156:43-49 (Dec. 8, 1992).

Crespi, C.L. et al., "A Metabolically Competent Human Cell Line Expressing Five cDNAs Encoding Procarcinogen-Activating Enzymes: Application to Mutagenicity Testing," Chem. Res. Toxicol., 4:566-572 (1991).

Nelson, D.R., "Cytochrome P450 and the individuality of species," Arch Biochem Biophys, 369:1-10 (1999).

Guengerich, F.P., Cytochrome, P450: Structure, Mechanism, and Biochemistry (2nd Edition), Chapter 14, edited by Paul R. Ortiz de Montellano, Plenum Press, New York, (1995).

Shimada, T. et al., "Interindividual variations in human liver cytochrome P-450 enzymes involved in the oxidation of drugs, carcinogens and toxic chemicals: studies with liver microsomes of 30 Japanese and 30 Caucasians," J. Pharmacol. Exp. Ther., 270(1):414-423 (Jul. 1994).

Ortiz De Montellano, P.R., Cytochrome, P450: Structure, Mechanism, and Biochemistry (2nd Edition), Chapter 8, edited by Paul R. Ortiz de Montellano, Plenum Press, New York, (1995).

Rettie, A.E. et al., Handbook of Drug Metabolism, edited by Thomas F. Woolf, Marcel Dekker, Inc., New York, pp. 131-147 (1999).

Ziegler, D.M., "Recent studies on the structure and function of multisubstrate flavin-containing monooxygenases," Annu. Rev. Pharmacol. Toxicol., 33:179-199 (1993).

Miller, J.A., "Sulfonation in Chemical Carcinogenesis • History and Present Status," Chem. Biol. Interact., 92:329-341 (1994).

Coffman, B. et al., "Accelerated Communication: Human UGT2B7 Catalyzes Morphine Glucuronidation," Drug Metabolism and Disposition, 25(1):1-4 (1996).

Chen and Struhl, "Yeast mRNA initiation sites are determined primarily by specific sequences, not by the distance from the TATA element," EMBO J., 4(12):3273-3280 (1985).

Yamazaki et al., "Lack of Electron Transfer from Cytochrome b5 in stimulation of Catalytic Activities of Cytochrome P450 3A4," The Journal of Biological Chemistry, 271(44):27438-27444 (Nov. 1, 1996).

Chang, LMS, et al., "Deoxynucleotide-polymerizing Enzymes of Calf Thymus Gland," J. Biol. Chem., 246:909-916 (Feb. 25, 1971).

Coldham et al., " Evaluation of a Recombinant Yeast Cell Estrogen Screening Assay," Environ. Health Perspect., 105(7):734-742 (Jul. 1997).

Cordon-Cardo et al., "Multidrug-resistance gene (P-glycoprotein) is expressed by endothelial cells at blood-brain barrier sites," Proc. Natl. Acad. Sci., 86(2): 695-698 (Jan. 1989).

Davis, CA et al., "Test of intron predictions reveals novel splice sites, alternatively spliced mRNAs and new introns in meiotically regulated genes of yeast," Nucleic Acids Res., 28(8):1700-1706 (Mar. 1, 2000).

* cited by examiner pYAC4-AscI
Vector for providing EVACS arms

CONCATEMERS OF DIFFERENTIALLY EXPRESSED MULTIPLE GENES

This application is a section 371 of PCT/DK2002/000055, filed Jan. 25, 2002 which claims priority from Danish patent application No. PA 2001 00127, filed Jan. 25, 2001 and the benefit of priority of U.S. provisional application Ser. No. 60/301,022, filed Jun. 27, 2001, which are hereby incorporated by reference in its entirety. All patent and nonpatent references cited in the application, or in the present application, are also hereby incorporated by reference in their entirety.

In the present invention are disclosed concatemers of concatenated expression cassettes and vectors that enable the synthesis of such concatemers. The main purpose of these concatemers is the controllable and co-ordinated expression of large numbers of heterologous genes in a single host cell. Furthermore, the invention relates to a concatemer of cassettes of nucleotide sequences and a method for preparing the concatemers. In a further aspect, the invention relates to transgenic host cells comprising at least one concatemer according to the invention, as well as to a method for preparing the transgenic host cells. Finally, the invention relates to a vector comprising a cassette of nucleotides, a method for preparing said vector, a nucleotide library comprising at least two primary vectors each comprising a cassette of nucleotides, a method for preparing the library.

PRIOR ART

The design of expression constructs and expression libraries is well known in the art.

WO 96/34112 discloses a combinatorial gene expression library with a pool of expression constructs each construct containing a cDNA or genomic DNA fragment from a plurality of donor organisms. The DNA fragments are operably associated with regulatory regions that drive expression in a host cell. The publication also discloses a combinatorial gene expression library in which each cell comprises a concatemer of cDNA fragments being operably associated with regulatory regions to drive expression of the genes encoded by the concatenated cDNA in a host organism. The host organism may be a yeast cell. The vector used for constructing the library may be a plasmid vector, a phage, a viral vector, a cosmid vector or an artificial chromosome (BAC or YAC). Suitable promoters include natural and synthetic promoters as well as constitutive and inducible promoters.

The genes used for the concatemers are prepared in a highly ordered multi-step procedure consisting of a number of discrete reaction steps. First, cDNA inserts are prepared using PCR and methylated dCTP to protect internal Not I and Bam HI restriction sites from later digestion. Promoter and terminator fragments are ligated to the 5' and 3' ends respectively using modified Bam HI adapters. The gene cassettes have the basic structure: promoter-coding sequence-terminator with different restriction sites in each end. The restriction site in the 3' end is protected. Similar gene cassettes can be prepared from genomic DNA which is randomly fragmented using a restriction enzyme.

The concatemers disclosed in WO 96/34112 are prepared in a highly ordered multi-step procedure, where the first gene cassette is ligated to an adapter nucleotide sequence linked to a bead having a blunt end corresponding to the blunt 5' end of the gene cassette. After ligation, the restriction site is no longer functional, since it was assembled using two compatible but not identical restriction sites. After linking the first gene cassette to the bead, the protected restriction site in the 3' end is "opened" and the second gene cassette is linked to the first. After 5 to 10 rounds of ligation of gene cassettes, the vector is ligated to the 3' end of the concatemer, the concatemer-vector construct is liberated from the bead and the 5' end is ligated to the other end of the vector. It is emphasised that the 3' and 5' ends of the concatemer should be non-compatible to avoid self assembly during cloning into the vector.

Due to the plurality of discrete steps in the preparation procedure, the method is not suitable for preparing concatemers of significantly larger size. Once the gene cassettes have been cloned into the vector, it is not possible to excise the cassettes or the complete concatemer from the vector using a restriction enzyme.

U.S. Pat. No. 6,057,103 (Diversa) discloses a method for identification of clones having a specified enzyme activity through isolation of DNA from a microorganism and hybridisation with a probe DNA comprising at least part of a sequence encoding an enzyme having a specified activity. The identified sequences are linked to a promoter sequence (e.g. eukaryotic promoters: CMV immediate/early, HSV thymidine kinase, early and late SV40, LTRs from retrovirus, and mouse metallothionein-I) and inserted into a vector, which may be a YAC or a P1 based artificial chromosome. Host cells used for transformation with the identified nucleotide sequences include bacterial cells, yeast, insect cells, mammalian cells. The disclosed vectors are not adapted for cloning of high numbers of expressible nucleotide sequences, and the reference does not disclose the concatemers for cloning of multiple genes into a host cell. More specifically the reference does not render possible the combination and screening of combinations of genes under conditions that allow genes to be combined in new ways.

U.S. Pat. No. 5,958,672 (Diversa) discloses a method for identifying protein activity of interest by culturing a gene expression library obtained from uncultivated microorganisms (or lower eukaryotic species). The gene expression library may be obtained from genomic DNA or from cDNA. The DNA clones are controllably associated to regulatory sequences, which drive the expression of the sequences in the host cell. The libraries may be screened against a DNA probe as described in U.S. Pat. No. 6,054,267. As is the case in the other references cited above, the combination of genes isolated from the uncultivated microorganisms is a static combination. Once, the isolated genes are inserted into the host cells, no further gene combinations and no further optimisation of gene combinations are intended.

It is one objective of the present invention to provide methods and vectors for cloning of large numbers of expressible nucleotide sequences, which are especially adapted for later random ligation into concatemers, which can in turn be inserted into an expression host for expression of the genes in the concatemer or a sub-set of the genes or of different subsets of the genes in the concatemer. Thereby it becomes possible to optimise combinations of expressible nucleotide sequences for any screenable trait.

It is a further objective of the present invention to provide methods and vectors, which allow for the production of concatemers, which are flexible. By flexible in this context is meant, that the gene cassettes of the concatemers can be disassembled and reassembled easily using standard molecular techniques, such as excision by the use of restriction enzymes.

SUMMARY OF THE INVENTION

According to a first aspect the invention relates to a nucleotide concatemer comprising in the 5'→3' direction a cassette of nucleotide sequence of the general formula

[rs$_2$-SP-PR-X-TR-SP-rs$_1$]$_n$ wherein
rs$_1$ and rs$_2$ together denote a restriction site,
SP individually denotes a spacer of at least two nucleotide bases,
PR denotes a promoter, capable of functioning in a cell,
X denotes an expressible nucleotide sequence,
TR denotes a terminator, and
SP individually denotes a spacer of at least two nucleotide bases, and
n≧2, and
wherein at least a first cassette is different from a second cassette.

The concatemers according to the invention may comprise a selection of expressible nucleotide sequences from just one expression state and can thus be assembled from one library representing this expression state or it may comprise cassettes from a number of different expression states mixed in any suitable ratio. The concatemers according to the invention are especially suitable for ligating into an artificial chromosome, which may be inserted into a host cell for co-ordinated expression. For this purpose, the variation among and between cassettes may be such as to minimise the chance of cross over as the host cell undergoes cell division such as through minimising the level of repeat sequences occurring in any one concatemer, since it is not an object of this embodiment of the invention to obtain recombination of concatemers with a segment in the host genome or an epitope of the host cells or any intraconcatemer recombination.

The concatemers can be used to make novel and non-native combinations of genes for co-ordinated expression in a host cell. Thereby new metabolic pathways can be generated, which may lead to the production of new metabolites, and/or to the metabolisation of compounds, which are otherwise not metabolisable by the host cells. The new gene combinations may also lead to metabolic pathways which produce metabolites in new quantities or in new compartments of the cell or outside the cell. Depending on the purpose, the selection of genes can be made completely random based on sourcing of expressible nucleotide sequences across the different kingdoms. However, it may also be advantageous to source genes from sources known to have certain metabolic pathways in order to make targeted new gene combinations. It may also be advantageous to source genes from organisms/tissues known to have relevant properties, e.g. pharmaceutical activity.

One of several advantages of the concatemers of the present invention is that the expression cassettes can be cut out from the concatemers at any point to make new combinations of expression cassettes. During re-assembly, further genes comprised in similar expression cassettes may be added if desired to modify the expression pattern. In this way, the concatemers according to the present invention present a powerful tool in generating novel gene combinations.

One advantage of the structure of the concatemer is that cassettes can be recovered from the host cell through nucleotide isolation and subsequent digestion with a restriction enzyme specific for the rs$_1$-rs$_2$ restriction site. The building blocks of the concatemers may thus be disassembled and reassembled at any point.

The cassettes of the concatemer may be joined head to tail or head to head or tail to tail, which does not affect expression of the expressible nucleotide sequences because each expressible nucleotide sequence is under the control of its own promoter. This is due to the fact that most restriction enzymes leave two identical overhangs, which may combine in either orientation at the same frequency.

However the restriction sites can also be selected so that head to tail arrangement is favoured, for example by using restriction enzymes that generate non-palindromic overhangs. Examples of such enzymes are listed in example 6c and most of the enzymes in 6d. Non-palindromic overhangs will prevent head to head and tail to tail ligation. By the use of two or more different entry vectors, the sequence of the cutting region can be designed to yield different overhangs after digestion with a single of these enzymes. Examples of such enzymes are most of the enzymes in example 6c and one in 6d, and have variable nucleotides (N or W) in the overhang. In this way a cassette can be excised with one enzyme that has non-identical overhangs. This will prevent intramolecular religation and prevent that identical cassettes ligate to each other, decreasing the risk of intramolecular recombination.

The invention in a further aspect relates to a method for concatenation comprising the steps of concatenating at least two cassettes of nucleotide sequences each cassette comprising a first sticky end, a spacer sequence, a promoter, an expressible nucleotide sequence, a terminator, and a second sticky end.

Preferably, the method comprises starting from primary vectors comprising a cassette having the following nucleotide sequence

[RS1-RS2-SP-PR-X-TR-SP-RS2'-RS1'], wherein X denotes an expressible nucleotide sequence,
RS1 and RS1' denote restriction sites,
RS2 and RS2' denote restriction sites different from RS1 and RS1',
SP individually denotes a spacer sequence of at least two nucleotides,
PR denotes a promoter,
TR denotes a terminator,
i) cutting the primary vector with the aid of at least one restriction enzyme specific for RS2 and RS2' obtaining cassettes having the general formula [rs$_2$-SP-PR-X-TR-SP-rs$_1$] wherein rs$_1$ and rs$_2$ together denote a functional restriction site RS2 or RS2',
ii) assembling the cut out cassettes through interaction between rs$_1$ and rs$_2$.

According to this embodiment, excision and concatenation is carried out in a "one step" reaction, i.e. without an intervening purification step, starting from vectors containing the expression cassettes. The expression cassettes can be cut out using two restriction enzymes specific for RS1 and RS2. Preferably for this one step reaction RS1 leaves blunt ends and RS2 leaves sticky ends. Upon addition of a ligase, the concatemer can be assembled in the mixture without any need for purification, since the vector backbone and the small RS1-RS2 fragments do not interfere with the concatenation reaction.

In the case, where the concatemer is to be inserted into an artificial chromosome vector for later transformation into an expression host cell, the AC vector arms can be added directly to the concatenation reaction mixture, so that the complete artificial chromosome vector containing the concatemer can be assembled in one step. By controlling the ratio of vector arms to cassettes, the size of the concatemer can be controlled. It is of course also possible to control the size of the concatemers by adding stopper fragments, the stopper fragments each having a RS2 or RS2' in one end and a non-complementary overhang or a blunt end in the other end. Vector arms may also be added later on in a separate step.

Advantageously, the method comprises addition of vector arms each having a RS2 or RS2' in one end and a non-complementary overhang or a blunt end in the other end. These can be added to the concatenation mixture, and even in this complex mixture, concatemers with one vector arm in each end will be produced under appropriate conditions. Host cells transformed with the desired construction, including the appropriate vector arms, can be selected by utilizing marker genes present on the arms.

In one aspect the invention relates to a host cell, which comprises at least one concatemer of individual oligonucleotide cassettes, each concatemer comprising oligonucleotide of the following formula in 5'→3' direction: $[rs_2\text{-SP-PR-X-TR-SP-}rs_1]_n$, wherein $rs_1$ and $rs_2$ together denote a restriction site, SP individually denotes a spacer of at least two nucleotide bases, PR denotes a promoter, capable of functioning in the cell, X denotes an expressible nucleotide sequence, TR denotes a terminator, and SP individually denotes a spacer of at least two nucleotide bases, wherein $n \geq 2$, and wherein at least two expressible nucleotide sequences are from different expression states.

In another aspect the invention relates to a cell comprising at least one concatemer of individual oligonucleotide cassettes, each concatemer comprising oligonucleotide of the following formula in 5'→3' direction:

$[rs_2\text{-SP-PR-X-TR-SP-}rs_1]_n$ wherein
$rs_1$ and $rs_2$ together denote a restriction site,
SP individually denotes a spacer of at least two nucleotide bases,
PR denotes a promoter, capable of functioning in the cell,
X denotes an expressible nucleotide sequence,
TR denotes a terminator, and
SP individually denotes a spacer of at least two nucleotide bases,
wherein $n \geq 2$, and
wherein $rs_1$-$rs_2$ in at least two cassettes is recognised by the same restriction enzyme.

Thereby non-naturally occurring combinations of expressible genes can be combined in one cell in such a way that co-ordinated expression of a subset of genes is made possible or all the inserted genes may be expressed at the same time. Through external regulation of the promoters controlling the expressible nucleotides sequences novel and non-naturally occurring combinations of expressed genes can be obtained. Since these novel and non-natural combinations of gene products are found in one and the same cell, the heterologous gene products may affect the metabolism of the host cell in novel ways and thus cause it to produce novel and/or non-native primary or secondary metabolites and/or known metabolites in novel amounts and/or known metabolites in novel compartments of the cell or outside the cells. The novel metabolic pathways and/or novel or modified metabolites may be obtained without substantially recombining the introduced genes with any segment in the host genome or any episome of the host cells.

The cells containing the concatemers, preferably in the form of artificial chromosomes, may be used for directed evolution by subjecting populations of cells to selective conditions. One advantage of the structure of the concatemers is that expression cassettes from different cells or from different populations of cells can be combined easily in a few steps thereby increasing the potential of the evolution. When the concatemers are inserted in the form of artificial chromosomes, evolution may also be carried out using traditional breeding and selection.

It is likely that through the combination of a high number of non-native genes in a host cell combinations of genes or single genes are inserted that are lethal or sub-lethal to the host cell. Through the co-ordinated expression of the genes in the host cell it is possible not only to induce the expression of any subset of genes but also to repress such expression, e.g. of lethal or sub-lethal genes.

By producing cells with combinations of concatemers comprising cassettes with expressible nucleotide sequences from a number of different expression states, which may be from any number of expression states, from the same or from selected species, from unrelated or distantly related species, or from species from different kingdoms, novel and random combinations of gene products are produced in one single cell. By furthermore having expressible nucleotide sequences under the control of a number of independently inducible or repressible promoters, a large number of different expression states can be created inside one single cell by selectively turning on and off groups of the inserted expressible nucleotide sequences. The number of independently inducible and/or repressible promoters in one cell may vary from 1 to 100, 1 to 50, 1 to 10, or such as up to 15, 20, 25 or above 50 promoters.

By inserting novel genes into the host cell, and especially by inserting a high number of novel genes from a wide variety of species into a host cell, it is highly likely that the gene products from this array of novel genes will interact with the pool of metabolites of the host cell and modify known metabolites and/or intermediates in novel ways to create novel compounds. Since the interaction is performed at the enzyme level it is furthermore likely that the result will be novel compounds with chiral centres, which are especially difficult to synthesise via chemical synthesis.

Novel metabolic pathways may also be made that are not capable of functioning, due to the absence of a substrate in the host cell. Such metabolic pathways may be made active by addition of non-host-cell specific substrates, which are metabolisable by the novel pathways.

One special advantage of the cells according to the present invention, is that incompatibility barriers between species do not limit the combinations of genes in one single cell.

According to a further aspect the invention relates to a method for producing a transgenic cell comprising inserting into a host cell a concatemer comprising a heterologous nucleotide sequence comprising at least two genes each controlled by a promoter, wherein the two genes and/or the two promoters are different.

According to a further aspect, the invention concerns a primary vector comprising a nucleotide sequence cassette of the general formula in 5'→3' direction:

[RS1-RS2-SP-PR-CS-TR-SP-RS2'-RS1']

wherein
RS1 and RS1' denote restriction sites,
RS2 and RS2' denote restriction sites different from RS1 and RS1',
SP individually denotes a spacer sequence of at least two nucleotides,
PR denotes a promoter,
CS denotes a cloning site,
TR denotes a terminator.

The cassette within the primary vector is useful for cloning and storing in a host cell random expressible nucleotide sequences, which are under the control of the promoter comprised in the cassette. The cassette may be inserted and removed by using restriction enzymes specific for either of the four restriction sites, of which RS1 and RS1' are preferably identical and RS2 and RS2' are also preferably identical. One special advantage of the cassette is that a collection of cassettes may be assembled into a concatemer of cassettes according to the invention by excising the cassettes from the primary vector, e.g. through use of the restriction enzyme(s) specific for RS2 and RS2', and concatenation of a population of random cassettes in a solution. The easiest concatenation is obtained when RS1 and RS1' leave blunt ends and RS2 and RS2' leave sticky ends. In this way it can be avoided that the empty vector takes part in the concatenation. Furthermore, it has been observed that the small fragments containing RS1-RS2 and RS1'-RS2' do not have to be removed, since they do not interfere with the concatenation. If desired, the small fragments can easily be removed using e.g. precipitation or filtration.

The primary vector according to the invention is especially adapted for expression with cDNA into it, because it is equipped with a promoter. Integration of genomic DNA is also possible however this may cause interaction between the native promoter sequences of the inserted genomic DNA and the external control obtainable through the promoter of the vector.

Preferably, PR is not functional in the host of the primary vector but only functional in the expression host, into which the concatemers are going to be inserted for expression. This is to avoid selection against genes which are lethal to the library host, in which the primary vector is stored and/or amplified.

The spacer sequence is inserted in the cassette in order to increase stability of the concatemers after concatenation. The cassettes are built so that they can be joined head to tail, head to head or tail to tail after concatenation. A concatemer of two cassettes can thus have the following structure:

3'rs$_2$-SP-PR-X-TR-SP-rs$_1$-rs$_2$-SP-PR-X-TR-SP-rs$_1$5'

3'rs$_2$-SP-TR-X-PR-SP-rs$_1$-rs$_2$-SP-PR-X-TR-SP-rs$_1$5'

3'rs$_2$-SP-PR-X-TR-SP-rs$_1$-rs$_2$-SP-TR-X-PR-SP-rs$_1$5'

(rs$_1$-rs$_2$ together denote a restriction site)

The presence of the spacer reduces the risk of hairpin formation between two adjacent terminator or promoter sequences, which may be identical. As a consequence, the presence of the spacer is also intended to increase the stability of the concatemers in the expression host into which they are inserted.

Using enzymes that leave non-palindromic overhangs it is possible to generate concatemers with essentially head to tail orientation.

In another aspect the invention relates to a method of preparing a primary vector comprising
   inserting an expressible nucleotide sequence into a cloning site in a primary vector comprising a cassette, the cassette comprising a nucleotide sequence of the general formula in 5'→3' direction:

[RS1-RS2-SP-PR-CS-TR-SP-RS2'-RS1']

wherein
   RS1 and RS1' denote restriction sites,
   RS2 and RS2' denote restriction sites different from RS1 and RS1',
   SP individually denotes a spacer sequence of at least two nucleotides,
   PR denotes a promoter,
   CS denotes a cloning site, and
   TR denotes a terminator.

In a further aspect the invention relates to a nucleotide library comprising at least two primary vectors each vector comprising a nucleotide sequence cassette of the general formula in 5'→3' direction:

[RS1-RS2-SP-PR-X-TR-SP-RS2'-RS1']

wherein
   RS1 and RS1' denote restriction sites,
   RS2 and RS2' denote restriction sites different from RS1 and RS1',
   SP individually denotes a spacer sequence of at least two nucleotides,
   PR denotes a promoter,
   X denotes an expressible nucleotide sequence,
   TR denotes a terminator.
   wherein the expressible nucleotide sequences are isolated from one expression state, and
   wherein at least two cassettes are different.

The nucleotide library may also be referred to as an entry (=initial) library, the intention being to use the nucleotide library as a suitable means for storing and amplifying a high number of vectors comprising the nucleotide cassettes according to the invention. It is also intended to excise the cassettes after amplification in order to use the excised cassettes for concatenation. Conveniently one nucleotide library may cover expressible nucleotide sequences from the same source pool, such as from the same expression state. Therefore, the library is conveniently used for introducing cDNA synthesised from mRNA isolated from one expression state.

Preferably, the PR sequences are not capable of functioning in the library host cells. This is to ensure that none of the expressible nucleotide sequences are lethal to the library host cell and therefore may be lost.

The nucleotide library furthermore provides a suitable means for later assembly of concatemers of cassettes stored in the library. According to an especially preferred embodiment of the invention, substantially all cassettes in the library are different. This difference is partly introduced to be able to co-ordinately express different subset of genes and partly to minimise the level of repeat sequences occurring in the concatemers.

In a still further aspect the invention relates to a method for preparing a nucleotide library comprising obtaining expressible nucleotide sequences, cloning the expressible nucleotide sequences into cloning sites of a mixture of primary vectors, the primary vectors comprising a cassette, the cassettes comprising a nucleotide sequence of the general formula in 5'→3' direction:

[RS1-RS2-SP-PR-CS-TR-SP-RS2'-RS1']

wherein
   RS1 and RS1' denote restriction sites,
   RS2 and RS2' denote restriction sites different from RS1 and RS1',
   SP individually denotes a spacer sequence of at least two nucleotides,
   PR denotes a promoter,
   CS denotes a cloning site, and
   TR denotes a terminator,
and transferring the primary vectors into a host cell obtaining a library.

Conveniently the method may comprise building a cDNA library from mRNA isolated from one expression state or starting from a cDNA library and cloning the cDNA sequences into a mixture of primary vectors according to the invention. In order to have the library and sub-libraries organised in a proper manner, each library comprises expressible nucleotide sequences representative of a given expression state.

For all the concatemers and libraries discussed herein the spacers (SP, promotors (PR), and terminators (TR) may be identical in all cassettes, but in preferred embodiments the spacers (SP, promotors (PR), and terminators (TR) are different for at least a part of the cassettes in a concatemer and a library.

BRIEF DESCRIPTION OF THE DRAWINGS

FIG. 2 shows a flow chart of the steps leading from an entry library comprising expressible nucleotide sequences to evolvable artificial chromosomes (EVAC) transformed into an appropriate host cell.

| Lane | F/Y |
|------|-----|
| 1 | 100/1 |
| 2 | 50/1 |
| 3 | 20/1 |
| 4 | 10/1 |
| 5 | 5/1 |
| 6 | 2/1 |
| 7 | 1/1 |
| 8 | 1/2 |
| 9 | 1/5 |

Legend: Lane M: molecular weight marker, λ-phage DNA digested w.Pst1. Lanes 1-9, concatenation reactions. Ratio of fragments to yac-arms(F/Y) as in table.

Figure 9A:
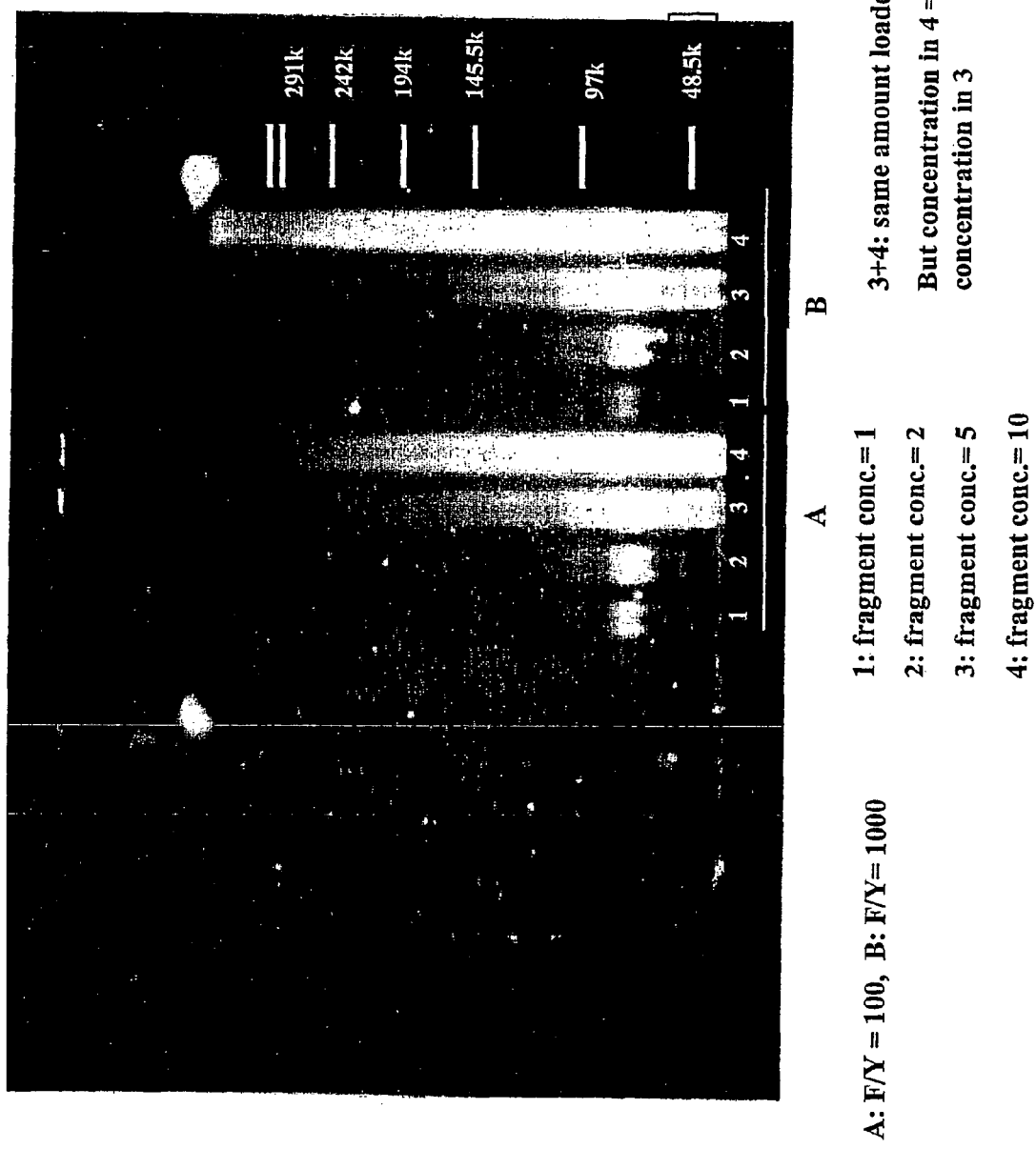
Figure 9B:
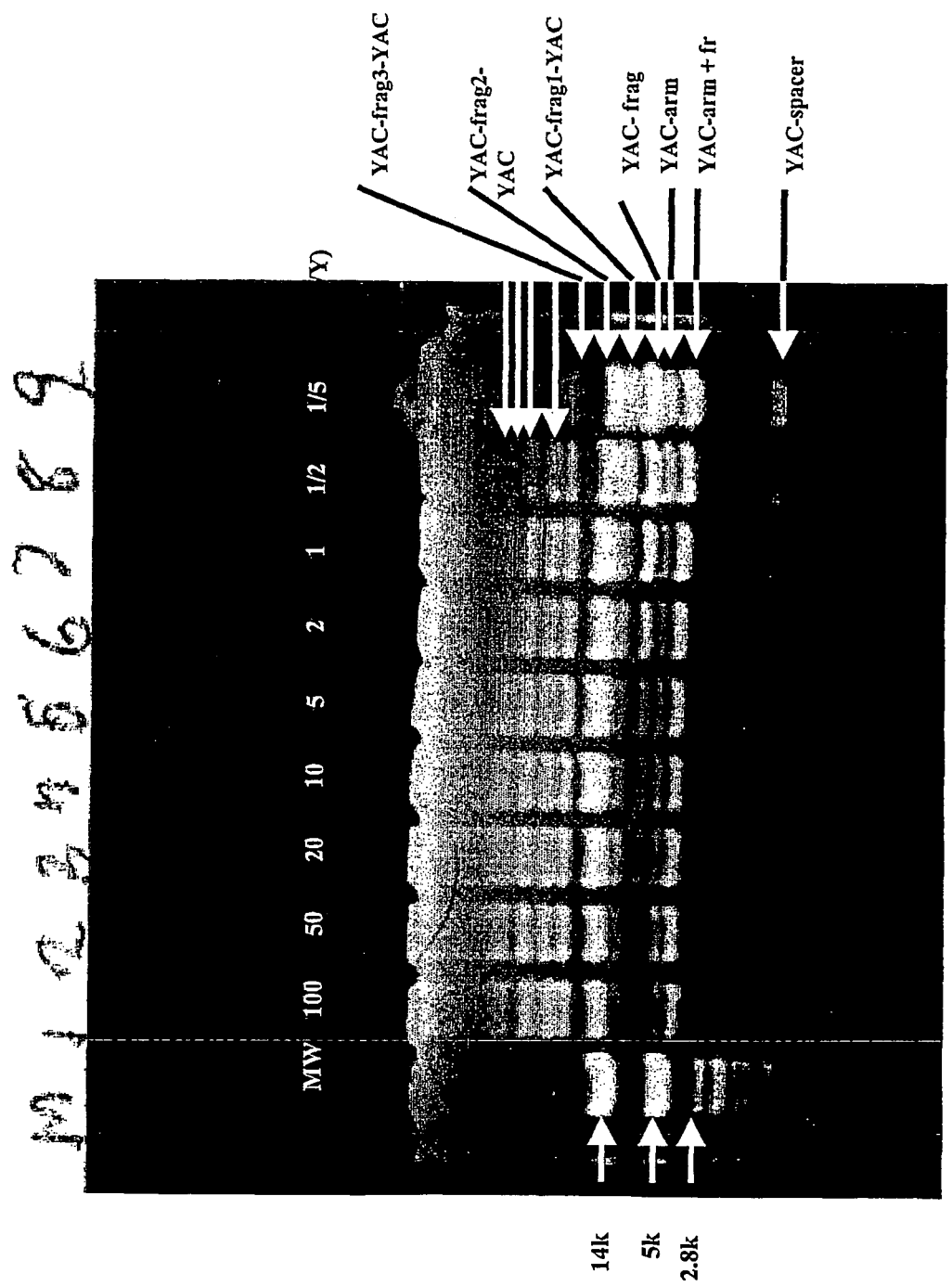

FIGS. 9a and 9b. illustrates the integration of concatenation with synthesis of evolvable artificial chromosomes and how concatemer size can be controlled by controlling the ratio of vector arms to expression cassettes, as described in example 7.

Figure 10:
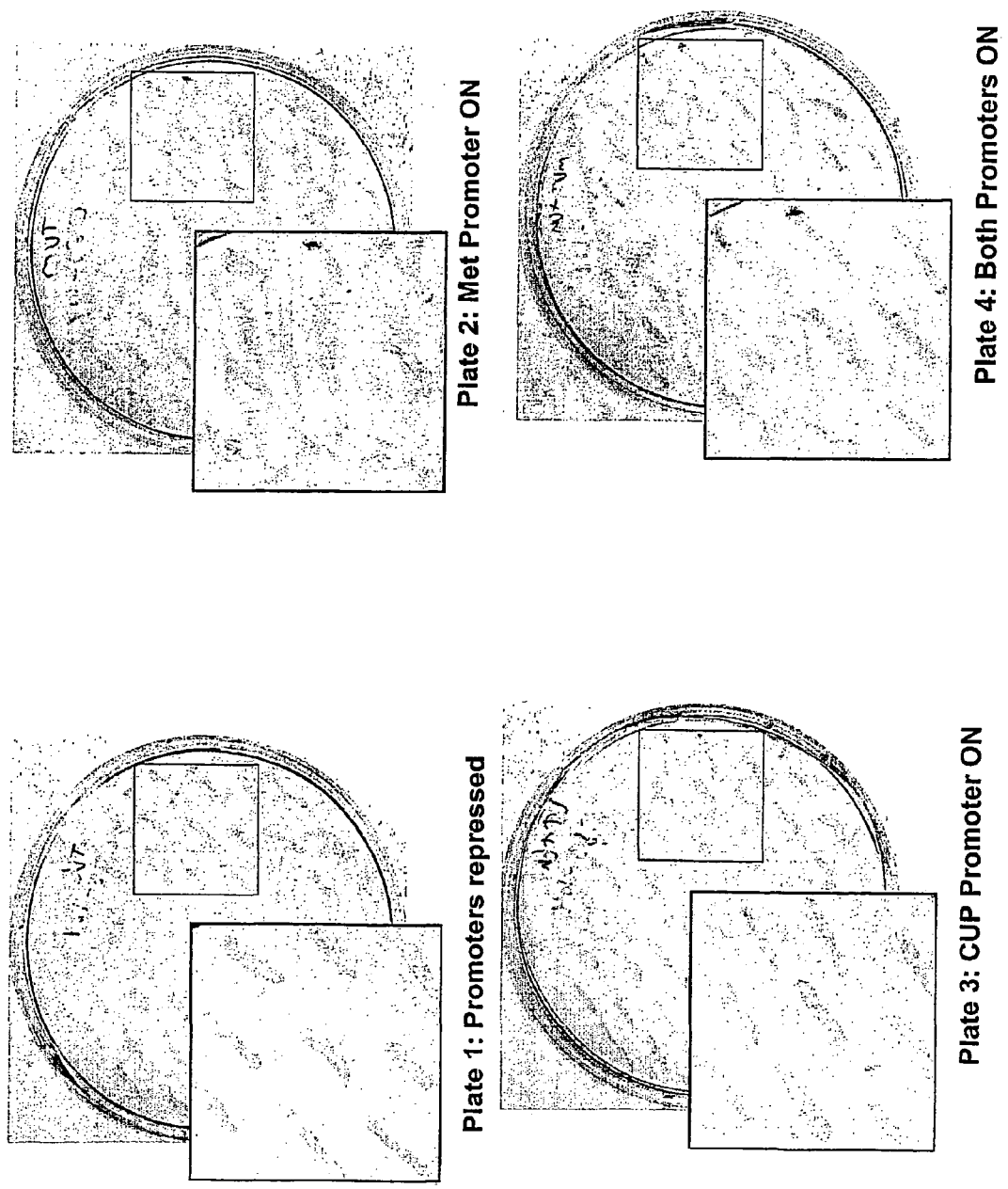

FIG. 10. Library of EVAC transformed population shown under 4 different growth conditions. Coloured phenotypes can be readily detected upon induction of the Met25 and/or the Cap1 promoters.

Figure 11:

FIG. 11. EVAC gel Legend: PFGE of EVAC containing clones: Lanes. a: Yeast DNA PFGE markers (strain YNN295), b: lambda ladder, c: non-transformed host yeast, 1-9: EVAC containing clones. EVACs in size range 1400-1600 kb. Lane 2 shows a clone containing 2 EVACs sized ~1500 kb and ~550 kb respectively. The 550 kb EVAC is comigrating with the 564 kb yeast chromosome and is resulting in an increased intensity of the band at 564 kb relative to the other bands in the lane. Arrows point up to EVAC bands.

DEFINITIONS

Oligonucleotides

Any fragment of nucleic acids having approximately from 2 to 10000 nucleic acids.
Restriction Site For the purposes of the present invention the abbreviation RSn (n=1, 2, 3, etc) is used to designate a nucleotide sequence comprising a restriction site. A restriction site is defined by a recognition sequence and a cleavage site. The cleavage site may be located within or outside the recognition sequence. The abbreviation "$rs_1$" or "$rs_2$" is used to designate the two ends of a restriction site after cleavage. The sequence "$rs_1$-$rs_2$" together designate a complete restriction site.

The cleavage site of a restriction site may leave a double stranded polynucleotide sequence with either blunt or sticky ends. Thus, "$rs_1$" or "$rs_2$" may designate either a blunt or a sticky end.

In the notation used throughout the present invention, formulae like:

RS1-RS2-SP-PR-X-TR-SP-RS2-RS1 should be interpreted to mean that the individual sequences follow in the order specified. This does not exclude that part of the recognition sequence of e.g. RS2 overlap with the spacer sequence, but it is a strict requirement that all the items except RS1 and RS1' are functional and remain functional after cleavage and re-assemblage. Furthermore the formulae do not exclude the possibility of having additional sequences inserted between the listed items. For example introns can be inserted as described in the invention below and further spacer sequences can be inserted between RS1 and RS2 and between TR and RS2. Important is that the sequences remain functional.

Furthermore, when reference is made to the size of the restriction site and/or to specific bases within it, only the bases in the recognition sequence are referred to.

Expression State

An expression state is a state in any specific tissue of any individual organism at any one time. Any change in conditions leading to changes in gene expression leads to another expression state. Different expression states are found in different individuals, in different species but they may also be found in different organs in the same species or individual, and in different tissue types in the same species or individual. Different expression states may also be obtained in the same organ or tissue in any one species or individual by exposing the tissues or organs to different environmental conditions comprising but not limited to changes in age, disease, infection, drought, humidity, salinity, exposure to xenobiotics, physiological effectors, temperature, pressure, pH, light, gaseous environment, chemicals such as toxins.

Artificial Chromosome

As used herein, an artificial chromosome (AC) is a piece of DNA that can stably replicate and segregate alongside endogenous chromosomes. For eukaryotes the artificial chromosome may also be described as a nucleotide sequence of substantial length comprising a functional centromer, functional telomeres, and at least one autonomous replicating sequence. It has the capacity to accommodate and express heterologous genes inserted therein. It is referred to as a mammalian artificial chromosome (MAC) when it contains an active mammalian centromere. Plant artificial chromosome and insect artificial chromosome (BUGAC) refer to chromosomes that include plant and insect centromers, respectively. A human artificial chromosome (HAC) refers to a chromosome that includes human centromeres, AVACs refer to avian artificial chromosomes. A yeast artificial chromosome (YAC) refers to chromosomes are functional in yeast, such as chromosomes that include a yeast centromere.

As used herein, stable maintenance of chromosomes occurs when at least about 85%, preferably 90%, more preferably 95% of the cells retain the chromosome. Stability is measured in the presence of a selective agent. Preferably these chromosomes are also maintained in the absence of a selective agent. Stable chromosomes also retain their structure during cell culturing, suffering neither intrachromosomal nor interchromosomal rearrangements.

DETAILED DESCRIPTION OF THE INVENTION

In the following the invention is described in the order in which the steps of obtaining a transformed host cell containing an evolvable artificial chromosome may be performed, starting with the entry vector.

Origin of Expressible Nucleotide Sequences

The expressible nucleotide sequences that can be inserted into the vectors, concatemers, and cells according to this invention encompass any type of nucleotide such as RNA, DNA. Such a nucleotide sequence could be obtained e.g. from cDNA, which by its nature is expressible. But it is also possible to use sequences of genomic DNA, coding for specific genes. Preferably, the expressible nucleotide sequences correspond to full length genes such as substantially full length cDNA, but nucleotide sequences coding for shorter peptides than the original full length mRNAs may also be used. Shorter peptides may still retain the catalytic activity similar to that of the native proteins.

Another way to obtain expressible nucleotide sequences is through chemical synthesis of nucleotide sequences coding for known peptide or protein sequences. Thus the expressible DNA sequences does not have to be a naturally occurring sequence, although it may be preferable for practical purposes to primarily use naturally occurring nucleotide sequences. Whether the DNA is single or double stranded will depend on the vector system used.

In most cases the orientation with respect to the promoter of an expressible nucleotide sequence will be such that the coding strand is transcribed into a proper mRNA. It is however conceivable that the sequence may be reversed generating an antisense transcript in order to block expression of a specific gene.

Cassettes

An important aspect of the invention concerns a cassette of nucleotides in a highly ordered sequence, the cassette having the general formula in 5'→3' direction:

[RS1-RS2-SP-PR-CS-TR-SP-RS2'-RS1']

wherein RS1 and RS1' denote restriction sites, RS2 and RS2' denote restriction sites different from RS1 and RS1', SP individually denotes a spacer sequence of at least two nucleotides, PR denotes a promoter, CS denotes a cloning site, and TR denotes a terminator.

It is an advantage to have two different restriction sites flanking both sides of the expression construct. By treating the primary vectors with restriction enzymes cleaving both restriction sites, the expression construct and the primary vector will be left with two non-compatible ends. This facilitates a concatenation process, since the empty vectors do not participate in the concatenation of expression constructs.

Restriction Sites

In principle, any restriction site, for which a restriction enzyme is known can be used. These include the restriction enzymes generally known and used in the field of molecular biology such as those described in Sambrook, Fritsch, Maniatis, "A laboratory Manual", $2^{nd}$ edition. Cold Spring Harbor Laboratory Press, 1989.

The restriction site recognition sequences preferably are of a substantial length, so that the likelihood of occurrence of an identical restriction site within the cloned oligonucleotide is minimised. Thus the first restriction site may comprise at least 6 bases, but more preferably the recognition sequence comprises at least 7 or 8 bases. Restriction sites having 7 or more non N bases in the recognition sequence are generally known as "rare restriction sites" (see example 6). However, the recognition sequence may also be at least 10 bases, such as at least 15 bases, for example at least 16 bases, such as at least 17 bases, for example at least 18 bases, such as at least 18 bases, for example at least 19 bases, for example at least 20 bases, such as at least 21 bases, for example at least 22 bases, such as at least 23 bases, for example at least 25 bases, such as at least 30 bases, for example at least 35 bases, such as at least 40 bases, for example at least 45 bases, such as at least 50 bases.

Preferably the first restriction site RS1 and RS1' is recognised by a restriction enzyme generating blunt ends of the double stranded nucleotide sequences. By generating blunt ends at this site, the risk that the vector participates in a subsequent concatenation is greatly reduced. The first restriction site may also give rise to sticky ends, but these are then preferably non-compatible with the sticky ends resulting from the second restriction site, RS2 and RS2' and with the sticky ends in the AC.

According to a preferred embodiment of the invention, the second restriction site, RS2 and RS2' comprises a rare restriction site. Thus, the longer the recognition sequence of the rare restriction site the more rare it is and the less likely is it that the restriction enzyme recognising it will cleave the nucleotide sequence at other—undesired—positions.

The rare restriction site may furthermore serve as a PCR priming site. Thereby it is possible to copy the cassettes via PCR techniques and thus indirectly "excise" the cassettes from a vector.

Spacer Sequence

The spacer sequence located between the RS2 and the PR sequence is preferably a non-transcribed spacer sequence. The purpose of the spacer sequence(s) is to minimise recombination between different concatemers present in the same cell or between cassettes present in the same concatemer, but it may also serve the purpose of making the nucleotide sequences in the cassettes more "host" like. A further purpose of the spacer sequence is to reduce the occurrence of hairpin formation between adjacent palindromic sequences, which may occur when cassettes are assembled head to head or tail to tail. Spacer sequences may also be convenient for introducing short conserved nucleotide sequences that may serve e.g. as PCR primer sites or as target for hybridization to e.g. nucleic acid or PNA or LNA probes allowing affinity purification of cassettes.

The cassette may also optionally comprise another spacer sequence of at least two nucleotides between TR and RS2. When cassettes are cut out from a vector and concatenated into concatemers of cassettes, the spacer sequences together ensure that there is a certain distance between two successive identical promoter and/or terminator sequences. This distance may comprise at least 50 bases, such as at least 60 bases, for example at least 75 bases, such as at least 100 bases, for example at least 150 bases, such as at least 200 bases, for example at least 250 bases, such as at least 300 bases, for example at least 400 bases, for example at least 500 bases, such as at least 750 bases, for example at least 1000 bases, such as at least 1100 bases, for example at least 1200 bases, such as at least 1300 bases, for example at least 1400 bases, such as at least 1500 bases, for example at least 1600 bases, such as at least 1700 bases, for example at least 1800 bases, such as at least 1900 bases, for example at least 2000 bases, such as at least 2100 bases, for example at least 2200 bases, such as at least 2300 bases, for example at least 2400 bases, such as at least 2500 bases, for example at least 2600 bases, such as at least 2700 bases, for example at least 2800 bases, such as at least 2900 bases, for example at least 3000 bases, such as at least 3200 bases, for example at least 3500 bases, such as at least 3800 bases, for example at least 4000 bases, such as at least 4500 bases, for example at least 5000 bases, such as at least 6000 bases.

The number of the nucleotides between the spacer located 5' to the PR sequence and the one located 3' to the TR sequence may be any. However, it may be advantageous to ensure that at least one of the spacer sequences comprises between 100 and 2500 bases, preferably between 200 and 2300 bases, more preferably between 300 and 2100 bases, such as between 400 and 1900 bases, more preferably between 500 and 1700 bases, such as between 600 and 1500 bases, more preferably between 700 and 1400 bases.

If the intended host cell is yeast, the spacers present in a concatemer should perferably comprise a combination of a few ARSes with varying lambda phage DNA fragments.

Preferred examples of spacer sequences include but are not limited to: Lamda phage DNA, prokaryotic genomic DNA such as E. coli genomic DNA, ARSes.

Promoter

A promoter is a DNA sequence to which RNA polymerase binds and initiates transcription. The promoter determines the polarity of the transcript by specifying which strand will be transcribed.

Bacterial promoters normally consist of −35 and −10 (relative to the transcriptional start) consensus sequences which are bound by a specific sigma factor and RNA polymerase.

Eukaryotic promoters are more complex. Most promoters utilized in expression vectors are transcribed by RNA polymerase II. General transcription factors (GTFs) first bind specific sequences near the transcriptional start and then recruit the binding of RNA polymerase II. In addition to these minimal promoter elements, small sequence elements are recognized specifically by modular DNA-binding/trans-activating proteins (e.g. AP-1, SP-1) which regulate the activity of a given promoter.

Viral promoters may serve the same function as bacterial and eukaryotic promoters. Upon viral infection of their host, viral promoters direct transcription either by using host transcriptional machinery or by supplying virally encoded enzymes to substitute part of the host machinery. Viral promoters are recognised by the transcriptional machinery of a large number of host organisms and are therefore often used in cloning and expression vectors.

Promoters may furthermore comprise regulatory elements, which are DNA sequence elements which act in conjunction with promoters and bind either repressors (e.g., lacO/LAC Iq repressor system in E. coli) or inducers (e.g., gal1/GAL4 inducer system in yeast). In either case, transcription is virtually "shut off" until the promoter is derepressed or induced, at which point transcription is "turned-on". The choice of promoter in the cassette is primarily dependent on the host organism into which the cassette is intended to be inserted. An important requirement to this end is that the promoter should preferably be capable of functioning in the host cell, in which the expressible nucleotide sequence is to be expressed.

Preferably the promoter is an externally controllable promoter, such as an inducible promoter and/or a repressible promoter. The promoter may be either controllable (repressible/inducible) by chemicals such as the absence/presence of chemical inducers, e.g. metabolites, substrates, metals, hormones, sugars. The promoter may likewise be controllable by certain physical parameters such as temperature, pH, redox status, growth stage, developmental stage, or the promoter may be inducible/repressible by a synthetic inducer/repressor such as the gal inducer.

In order to avoid unintentional interference with the gene regulation systems of the host cell, and in order to improve controllability of the co-ordinated gene expression the promoter is preferably a synthetic promoter. Suitable promoters are described in U.S. Pat. No. 5,798,227, U.S. Pat. No. 5,667,986. Principles for designing suitable synthetic eukaryotic promoters are disclosed in U.S. Pat. No. 5,559,027, U.S. Pat. No. 5,877,018 or U.S. Pat. No. 6,072,050.

Synthetic inducible eukaryotic promoters for the regulation of transcription of a gene may achieve improved levels of protein expression and lower basal levels of gene expression. Such promoters preferably contain at least two different classes of regulatory elements, usually by modification of a native promoter containing one of the inducible elements by inserting the other of the inducible elements. For example, additional metal responsive elements IR:Es) and/or glucocorticoid responsive elements (GREs) may be provided to native promoters. Additionally, one or more constitutive elements may be functionally disabled to provide the lower basal levels of gene expression.

Preferred examples of promoters include but is not limited to those promoters being induced and/or repressed by any factor selected from the group comprising carbohydrates, e.g. galactose; low inorganic phosphase levels; temperature, e.g. low or high temperature shift; metals or metal ions, e.g. copper ions; hormones, e.g. dihydrotestosterone; deoxycorticosterone; heat shock (e.g. 39° C.); methanol; redox-status; growth stage, e.g. developmental stage; synthetic inducers, e.g. gal inducer. Examples of such promoters include ADH 1, PGK 1, GAP 491, TPI, PYK, ENO, PMA 1, PHO5, GAL 1, GAL 2, GAL 10, MET25, ADH2, MEL 1, CUP 1, HSE, AOX, MOX, SV40, CaMV, Opaque-2, GRE, ARE, PGK/ARE hybrid, CYC/GRE hybrid, TPI/α2 operator, AOX 1, MOX A.

More preferably, however the promoter is selected from hybrid promoters such as PGK/ARE hybrid, CYC/GRE hybrid or from synthetic promoters. Such promoters can be controlled without interfering too much with the regulation of native genes in the expression host.

Yeast Promoters

In the following, examples of known yeast promoters that may be used in conjunction with the present invention are shown. The examples are by no way limiting and only serve to indicate to the skilled practitioner how to select or design promoters that are useful according to the present invention.

Although numerous transcriptional promoters which are functional in yeasts have been described in the literature, only some of them have proved effective for the production of polypeptides by the recombinant route. There may be mentioned in particular the promoters of the PGK genes (3-phosphoglycerate kinase, TDH genes encoding GAPDH (Glyceraldehyde phosphate dehydrogenase), TEF1 genes (Elongation factor 1), MFα1 (α sex pheromone precursor) which are considered as strong constitutive promoters or alternatively the regulatable promoter CYCI which is repressed in the presence of glucose or PHO5 which can be regulated by thiamine. However, for reasons which are often unexplained, they do not always allow the effective expression of the genes which they control. In this context, it is always advantageous to be able to have new promoters in order to generate new effective host/vector systems. Furthermore, having a choice of effective promoters in a given cell also makes it possible to envisage the production of multiple proteins in this same cell (for example several enzymes of the same metabolic chain) while avoiding the problems of recombination between homologous sequences.

In general, a promoter region is situated in the 5' region of the genes and comprises all the elements allowing the transcription of a DNA fragment placed under their control, in particular:

(1) a so-called minimal promoter region comprising the TATA box and the site of initiation of transcription, which determines the position of the site of initiation as well as the basal level of transcription. In *Saccharomyces cerevisiae*, the length of the minimal promoter region is relatively variable. Indeed, the exact location of the TATA box varies from one gene to another and may be situated from −40 to −120 nucleotides upstream of the site of the initiation (Chen and Struhl, 1985, EMBO J., 4, 3273-3280)

(2) sequences situated upstream of the TATA box (immediately upstream up to several hundreds of nucleotides) which make it possible to ensure an effective level of transcription either constitutively (relatively constant level of transcription all along the cell cycle, regardless of the conditions of culture) or in a regulatable manner (activation of transcription in the presence of an activator and/or repression in the presence of a repressor). These sequences, may be of several types: activator, inhibitor, enhancer, inducer, repressor and may respond to cellular factors or varied culture conditions.

Examples of such promoters are the ZZA1 and ZZA2 promoters disclosed in U.S. Pat. No. 5,641,661, the EF1-α protein promoter and the ribosomal protein S7 gene promoter disclosed in WO 97/44470, the COX 4 promoter and two unknown promoters (SEQ ID No: 1 and 2 in the document) disclosed in U.S. Pat. No. 5,952,195. Other useful promoters include the HSP150 promoter disclosed in WO 98/54339 and the SV40 and RSV promoters disclosed in U.S. Pat. No. 4,870,013 as well as the PyK and GAPDH promoters disclosed in EP 0 329 203 A1.

Synthetic Yeast Promoters

More preferably the invention employs the use of synthetic promoters. Synthetic promoters are often constructed by combining the minimal promoter region of one gene with the upstream regulating sequences of another gene. Enhanced promoter control may be obtained by modifying specific sequences in the upstream regulating sequences, e.g. through substitution or deletion or through inserting multiple copies of specific regulating sequences. One advantage of using synthetic promoters is that they may be controlled without interfering too much with the native promoters of the host cell.

One such synthetic yeast promoter comprises promoters or promoter elements of two different yeast-derived genes, yeast killer toxin leader peptide, and amino terminus of IL-1β (WO 98/54339).

Another example of a yeast synthetic promoter is disclosed in U.S. Pat. No. 5,436,136 (Hinnen et al), which concerns a yeast hybrid promoter including a 5' upstream promoter element comprising upstream activation site(s) of the yeast PHO5 gene and a 3' downstream promoter element of the yeast GAPDH gene starting at nucleotide −300 to −180 and ending at nucleotide −1 of the GAPDH gene.

Another example of a yeast synthetic promoter is disclosed in U.S. Pat. No. 5,089,398 (Rosenberg et al). This disclosure describes a promoter with the general formula -(P.R.(2)–P.R.(1))- wherein:

P.R.(1) is the promoter region proximal to the coding sequence and having the transcription initiation site, the RNA polymerase binding site, and including the TATA box, the CAAT sequence, as well as translational regulatory signals, e.g., capping sequence, as appropriate;

P.R.(2) is the promoter region joined to the 5'-end of P.R.(1) associated with enhancing the efficiency of transcription of the RNA polymerase binding region;

In U.S. Pat. No. 4,945,046 (Horii et al) discloses a further example of how to design a synthetic yeast promoter. This specific promoter comprises promoter elements derived both from yeast and from a mammal. The hybrid promoter consists essentially of *Saccharomyces cerevisiae* PHO5 or GAP-DH promoter from which the upstream activation site (UAS) has been deleted and replaced by the early enhancer region derived from SV40 virus.

Cloning Site

The cloning site in the cassette in the primary vector should be designed so that any nucleotide sequence can be cloned into it.

The cloning site in the cassette preferably allows directional cloning. Hereby is ensured that transcription in a host cell is performed from the coding strand in the intended direction and that the translated peptide is identical to the peptide for which the original nucleotide sequence codes.

However according to some embodiments it may be advantageous to insert the sequence in opposite direction. According to these embodiments, so-called antisense constructs may be inserted which prevent functional expression of specific genes involved in specific pathways. Thereby it may become possible to divert metabolic intermediates from a prevalent pathway to another less dominant pathway.

The cloning site in the cassette may comprise multiple cloning sites, generally known as MCS or polylinker sites, which is a synthetic DNA sequence encoding a series of restriction endonuclease recognition sites. These sites are engineered for convenient cloning of DNA into a vector at a specific position and for directional cloning of the insert.

Cloning of cDNA does not have to involve the use of restriction enzymes. Other alternative systems include but are not limited to:

Creator™ Cre-loxP system from Clontech, which uses recombination and loxP sites use of Lambda attachment sites (att-λ), such as the Gateway™ system from Life Technologies.

Both of these systems are directional.

Terminator

The role of the terminator sequence is to limit transcription to the length of the coding sequence. An optimal terminator sequence is thus one, which is capable of performing this act in the host cell.

In prokaryotes, sequences known as transcriptional terminators signal the RNA polymerase to release the DNA template and stop transcription of the nascent RNA.

In eukaryotes, RNA molecules are transcribed well beyond the end of the mature mRNA molecule. New transcripts are enzymatically cleaved and modified by the addition of a long sequence of adenylic acid residues known as the poly-A tail. A polyadenylation consensus sequence is located about 10 to 30 bases upstream from the actual cleavage site.

Preferred examples of yeast derived terminator sequences include, but are not limited to: ADN1, CYC1, GPD, ADH1 alcohol dehydrogenase.

Intron

Optionally, the cassette in the vector comprises an intron sequence, which may be located 5' or 3' to the expressible nucleotide sequence. The design and layout of introns is well known in the art. The choice of intron design largely depends on the intended host cell, in which the expressible nucleotide sequence is eventually to be expressed. The effects of having intron sequence in the expression cassettes are those generally associated with intron sequences.

Examples of yeast introns can be found in the literature and in specific databases such as Ares Lab Yeast Intron Database (Version 2.1) as updated on 15 Apr. 2000. Earlier versions of the database as well as extracts of the database have been published in: "Genome-wide bioinformatic and molecular analysis of introns in *Saccharomyces cerevisiae*." by Spingola M, Grate L, Haussler D, Ares M Jr. (RNA 1999 February; 5(2):221-34) and "Test of intron predictions reveals novel splice sites, alternatively spliced mRNAs and new introns in meiotically regulated genes of yeast." by Davis C A, Grate L, Spingola M, Ares M Jr, (Nucleic Acids Res Apr. 15, 2000; 28(8):1700-6).

Primary Vectors (Entry Vectors)

By the term entry vector is meant a vector for storing and amplifying cDNA or other expressible nucleotide sequences using the cassettes according to the present invention. The primary vectors are preferably able to propagate in *E. coli* or any other suitable standard host cell. It should preferably be amplifiable and amenable to standard normalisation and enrichment procedures.

The primary vector may be of any type of DNA that has the basic requirements of a) being able to replicate itself in at least one suitable host organism and b) allows insertion of foreign DNA which is then replicated together with the vector and c) preferably allows selection of vector molecules that contain insertions of said foreign DNA. In a preferred embodiment the vector is able to replicate in standard hosts like yeasts, and bacteria and it should preferably have a high copy number per host cell. It is also preferred that the vector in addition to a host specific origin of replication, contains an origin of replication for a single stranded virus, such as e.g. the f1 origin for filamentous phages. This will allow the production of single stranded nucleic acid which may be useful for normalisation and enrichment procedures of cloned sequences. A vast number of cloning vectors have been described which are commonly used and references may be given to e.g. Sambrook, J; Fritsch, E. F; and Maniatis T. (1989) Molecular Cloning: A laboratory manual. Cold Spring Harbour Laboratory Press, USA, Netherlands Culture Collection of Bacteria (www.cbs.knaw.nl/NCCB/collection.htm) or Department of Microbial Genetics, National Institute of Genetics, Yata 1111 Mishima Shizuoka 411-8540, Japan (www.shigen.nig.ac.jp/cvector/cvector.html). A few type-examples that are the parents of many popular derivatives are M13mp10, pUC18, Lambda. gt 10, and pYAC4. Examples of primary vectors include but are not limited to M13K07, pBR322, pUC18, pUC19, pUC118, pUC119, pSP64, pSP65, pGEM-3, pGEM-3Z, pGEM-3Zf(-), pGEM4, pGEM-4Z, πAN13, pBluescript II, CHARON 4A, λ$^+$, CHARON 21A, CHARON 32, CHARON 33, CHARON 34, CHARON 35, CHARON 40, EMBL3A, λ2001, λDASH, λFIX, λgt10, λgt11, λgt18, λgt20, λgt22, λORF8, λZAP/R, pJB8, c2RB, pcos1EMBL Methods for cloning of cDNA or genomic DNA into a vector are well known in the art. Reference may be given to J. Sambrook, E. F. Fritsch, T. Maniatis: Molecular Cloning, A Laboratory Manual (2$^{nd}$ edition, Cold Spring Harbor Laboratory Press, 1989).

Figure 3:
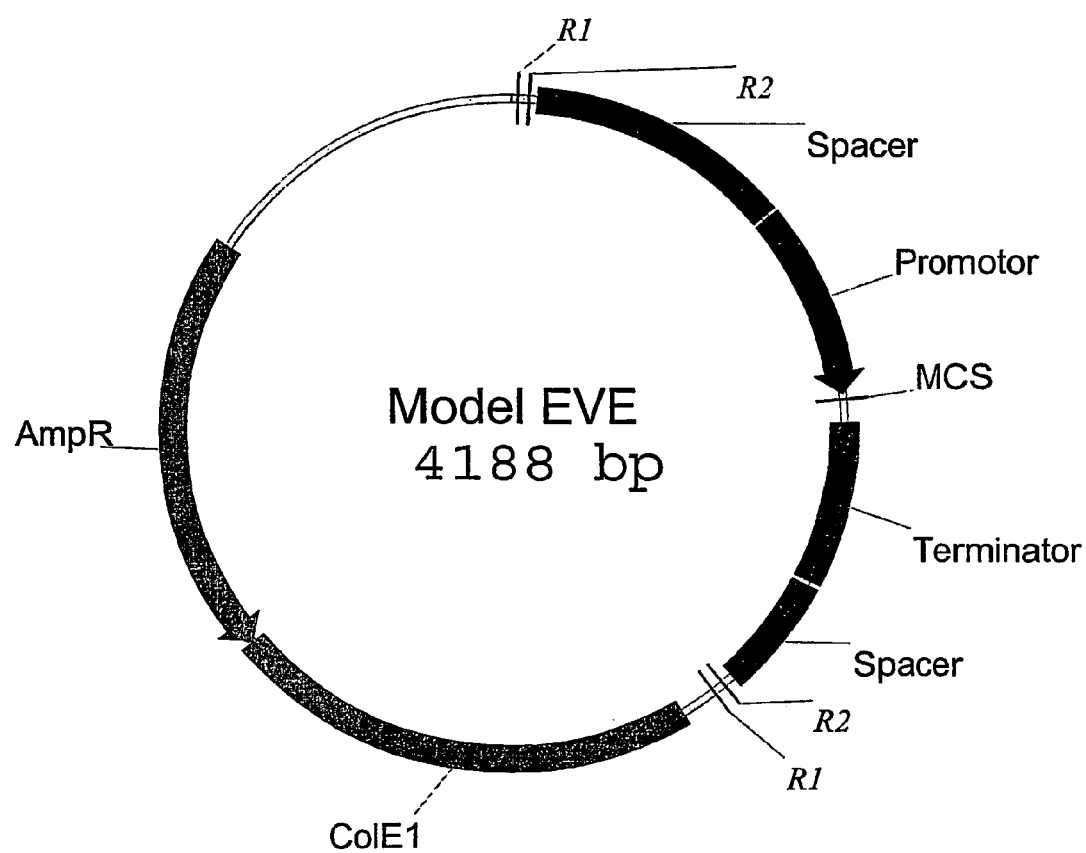
FIG. 3 shows a model entry vector. MCS is a multi cloning site for inserting expressible nucleotide sequences. Amp R is the gene for ampicillin resistance. Col E is the origin of replication in E. coli. R1 and R2 are restriction enzyme recognition sites.

One example of a circular model entry vector is described in FIG. 3. The vector, EVE contains the expression cassette, R1-R2-Spacer-Promoter-Multi Cloning Site-Terminator-Spacer-R2-R1. The vector furthermore contains a gene for ampicillin resistance, AmpR, and an origin of replication for *E. coli*, ColE1.

Figure 4:
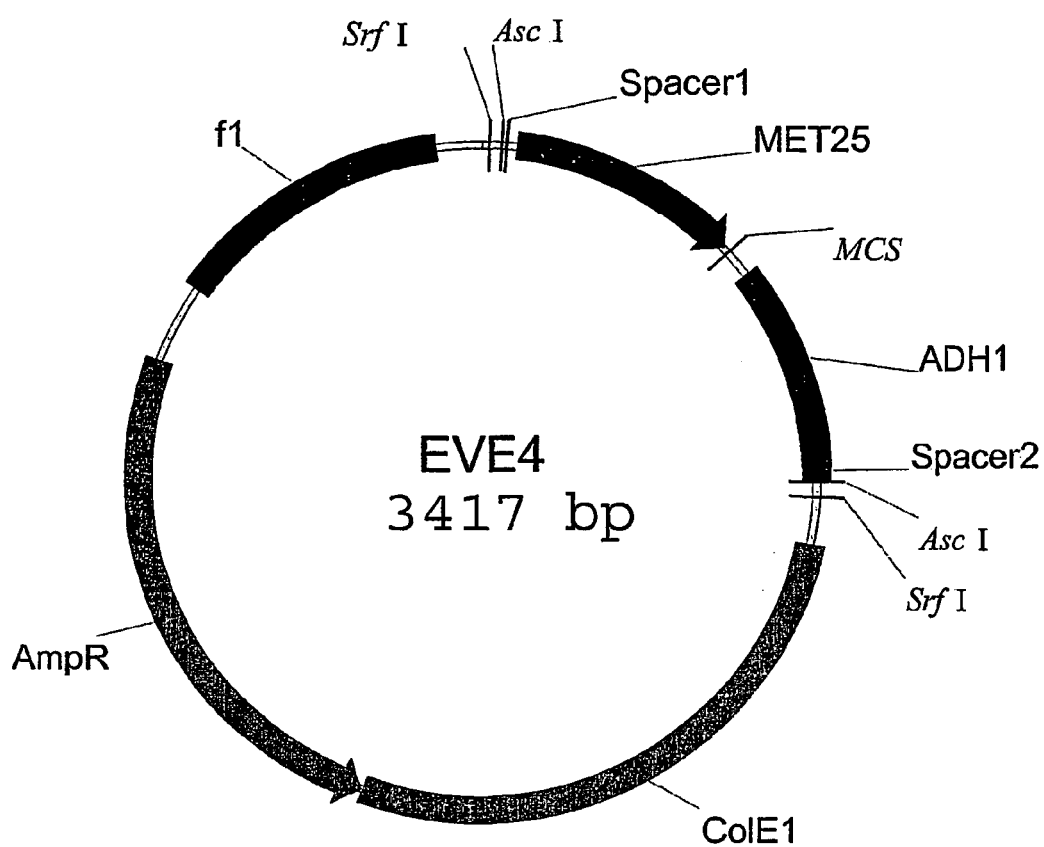
FIG. 4 shows an example of an entry vector according to the invention, EVE4. MET25 is a promoter, ADH1 is a terminator, f1 is an origin of replication for filamentous phages, e.g. M13. Spacer 1 and spacer 2 are constituted by a few nucleotides deriving from the multiple cloning site, MCS, SrfI and AscI are restriction enzyme recognition sites. Other abbreviations, see FIG. 3. The sequence of the vector is set forth in SEQ ID NO 1.
Figure 5:
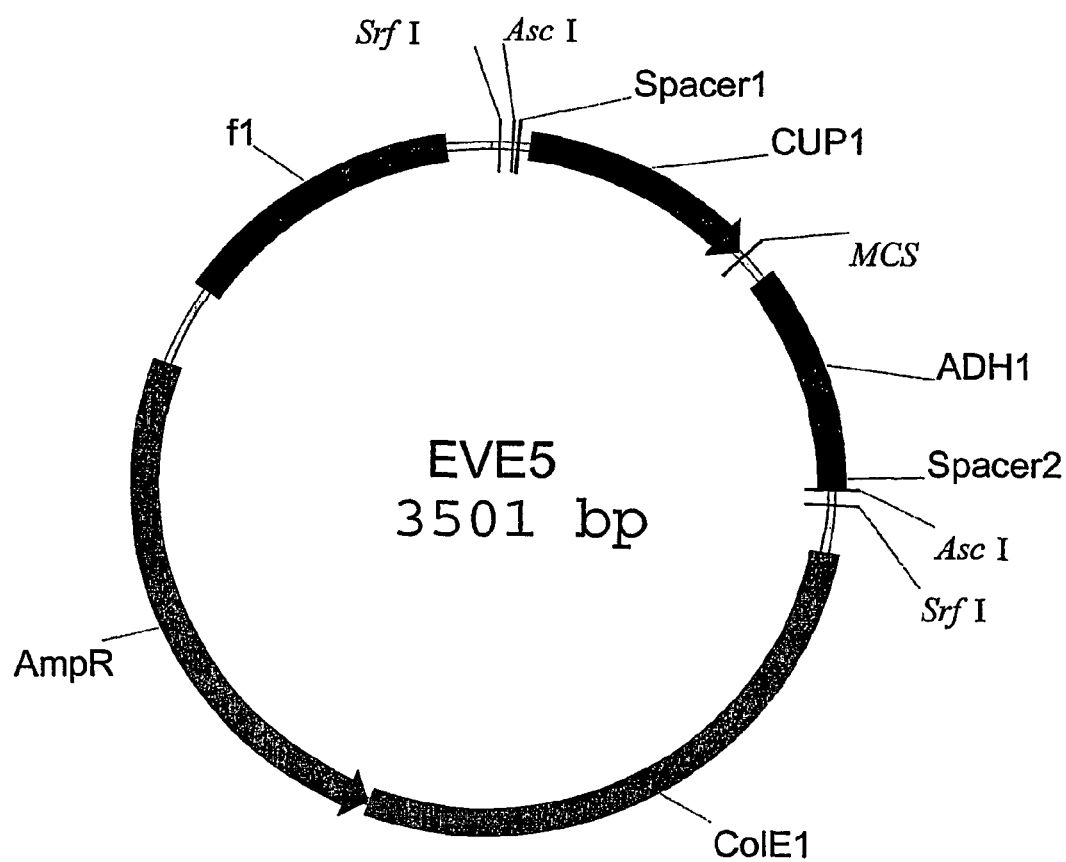
FIG. 5 shows an example of an entry vector according to the invention, EVE5. CUP1 is a promoter, ADH1 is a terminator, f1 is an origin of replication for filamentous phages, e.g. M13. Spacer 1 and spacer 2 are constituted by a few nucleotides deriving from the multiple cloning site, MCS, SrfI and AscI are restriction enzyme recognition sites. Other abbreviations, see FIG. 3. The sequence of the vector is set forth in SEQ ID NO 2.
Figure 6:
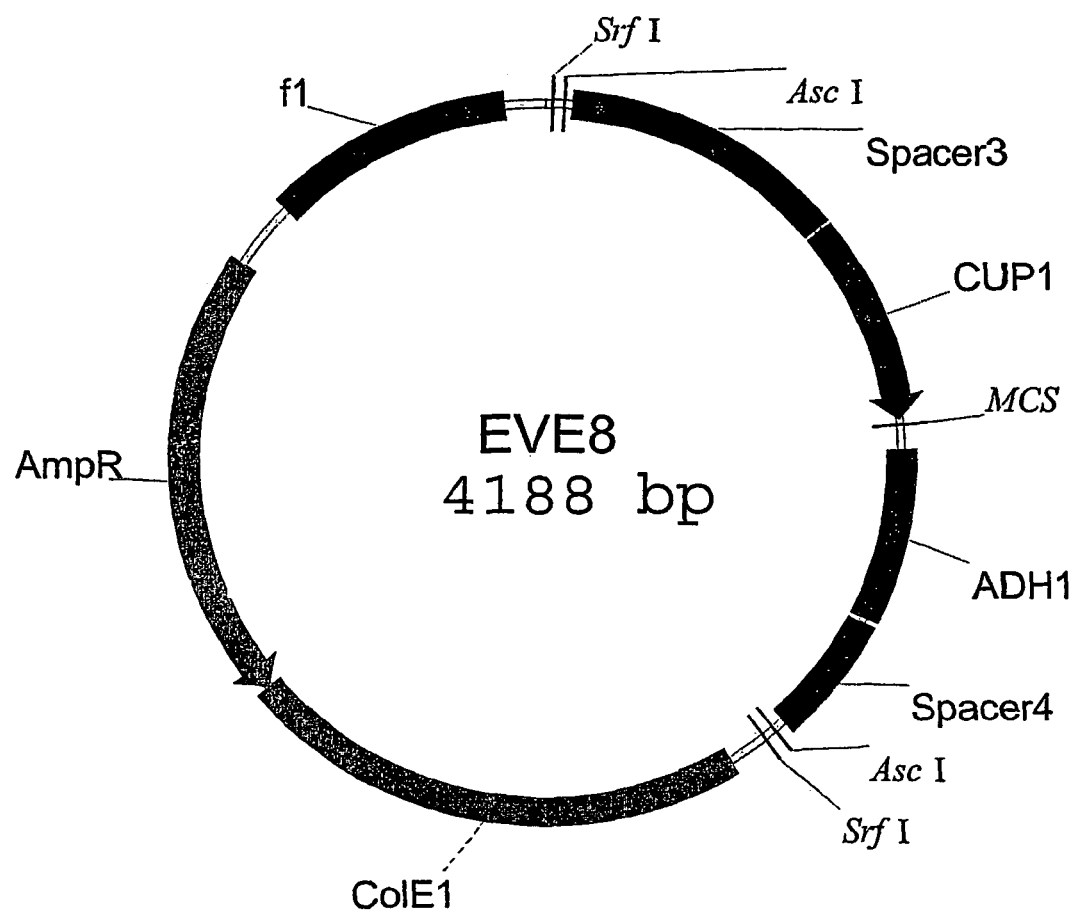
FIG. 6 shows an example of an entry vector according to the invention, EVE8. CUP1 is a promoter, ADH1 is a terminator, f1 is an origin of replication for filamentous phages, e.g. M13. Spacer 3 is a 550 bp fragment of lambda phage DNA fragment. Spacer 4 is a ARS1 sequence from yeast. SrfI and AscI are restriction enzyme recognition sites. Other abbreviations, see FIG. 3. The sequence of the vector is set forth in SEQ ID NO 3.

The entry vectors EVE4, EVE5, and EVE8 shown in FIGS. 4, 5, and 6. These all contain SrfI as R1 and AscI as R2. Both of these sites are palindromic and are regarded as rare restriction sites having 8 bases in the recognition sequence. The vectors furthermore contain the AmpR ampicillin resistance gene, and the ColE1 origin or replication for *E. coli* as well as f1, which is an origin of replication for filamentous phages, such as M13. EVE4 (FIG. 4) contains the MET25 promoter and the ADH1 terminator. Spacer 1 and spacer 2 are short sequences deriving from the multiple cloning site, MCS. EVE5 (FIG. 5) contains the CUP1 promoter and the ADH1 terminator. EVE8 (FIG. 6) contains the CUP1 promoter and the AD1 terminator. The spacers of EVE8 are a 550 bp lambda phage DNA (spacer 3) and an ARS sequence from yeast (spacer 4).

Nucleotide Library (Entry Library)

Methods as well as suitable vectors and host cells for constructing and maintaining a library of nucleotide sequences in a cell are well known in the art. The primary requirement for the library is that is should be possible to store and amplify in it a number of primary vectors (constructs)

according to this invention, the vectors (constructs) comprising expressible nucleotide sequences from at least one expression state and wherein at least two vectors (constructs) are different.

One specific example of such a library is the well known and widely employed cDNA libraries. The advantage of the cDNA library is mainly that it contains only DNA sequences corresponding to transcribed messenger RNA in a cell. Suitable methods are also present to purify the isolated mRNA or the synthesised cDNA so that only substantially full-length cDNA is cloned into the library.

Methods for optimisation of the process to yield substantially full length cDNA may comprise size selection, e.g. electrophoresis, chromatography, precipitation or may comprise ways of increasing the likelihood of getting full length cDNAs, e.g. the SMART™ method (Clonetech) or the Cap-Trap™ method (Stratagene).

Preferably the method for making the nucleotide library comprises obtaining a substantially full length cDNA population comprising a normalised representation of cDNA species. More preferably a substantially full length cDNA population comprises a normalised representation of cDNA species characteristic of a given expression state.

Normalisation reduces the redundancy of clones representing abundant mRNA species and increases the relative representation of clones from rare mRNA species.

Methods for normalisation of cDNA libraries are well known in the art. Reference may be given to suitable protocols for normalisation such as those described in U.S. Pat. No. 5,763,239 (DIVERSA) and WO 95/08647 and WO 95/11986. and Bonaldo, Lennon, Soares, Genome Research 1996, 6:791-806; Ali, Holloway, Taylor, Plant Mol Biol Reporter, 2000, 18:123-132.

Enrichment methods are used to isolate clones representing mRNA which are characteristic of a particular expression state. A number of variations of the method broadly termed as subtractive hybrisation are known in the art. Reference may be given to Sive, John, Nucleic Acid Res, 1988, 16:10937; Diatchenko, Lau, Campbell et al, PNAS, 1996, 93:6025-6030; Caminci, Shibata, Hayatsu, Genome Res, 2000, 10:1617-30, Bonaldo, Lennon, Soares, Genome Research 1996, 6:791-806; Ali, Holloway, Taylor, Plant Mol Biol Reporter, 2000, 18:123-132. For example, enrichment may be achieved by doing additional rounds of hybridization similar to normalization procedures, using e.g. cDNA from a library of abundant clones or simply a library representing the uninduced state as a driver against a tester library from the induced state. Alternatively mRNA or PCR amplified cDNA derived from the expression state of choice can be used to subtract common sequences from a tester library. The choice of driver and tester population will depend on the nature of target expressible nucleotide sequences in each particular experiment.

In the library an expressible nucleotide sequence coding for one peptide is preferably found in different but similar vectors under the control of different promoters. Preferably the library comprises at least three primary vectors with an expressible nucleotide sequence coding for the same peptide under the control of three different promoters. More preferably the library comprises at least four primary vectors with an expressible nucleotide sequence coding for the same peptide under the control of four different promoters. More preferably the library comprises at least five primary vectors with an expressible nucleotide sequence coding for the same peptide under the control of five different promoters, such as comprises at lest six primary vectors with an expressible nucleotide sequence coding for the same peptide under the control of six different promoters, for example comprises at least seven primary vectors with an expressible nucleotide sequence coding for the same peptide under the control of seven different promoters, for example comprises at least eight primary vectors with an expressible nucleotide sequence coding for the same peptide under the control of eight different promoters, such as comprises at least nine primary vectors with an expressible nucleotide sequence coding for the same peptide under the control of nine different promoters, for example comprises at least ten primary vectors with an expressible nucleotide sequence coding for the same peptide under the control of ten different promoters.

The expressible nucleotide sequence coding for the same peptide preferably comprises essentially the same nucleotide sequence, more preferably the same nucleotide sequence.

By having a library with what may be termed one gene under the control of a number of different promoters in different vectors, it is possible to construct from the nucleotide library an array of combinations of genes and promoters. Preferably, one library comprises a complete or substantially complete combination such as a two dimensional array of genes and promoters, wherein substantially all genes are found under the control of substantially all of a selected number of promoters.

According to another embodiment of the invention the nucleotide library comprises combinations of expressible nucleotide sequences combined in different vectors with different spacer sequences and/or different intron sequences. Thus any one expressible nucleotide sequence may be combined in a two, three, four or five dimensional array with different promoters and/or different spacers and/or different introns and/or different terminators. The two, three, four or five dimensional array may be complete or incomplete, since not all combinations will have to be present.

The library may suitably be maintained in a host cell comprising prokaryotic cells or eukaryotic cells. Preferred prokaryotic host organisms may include but are not limited to *Escherichia coli, Bacillus subtilis, Streptomyces lividans, Streptomyces coelicolor Pseudomonas aeruginosa, Myxococcus xanthus*.

Yeast species such as *Saccharomyces cerevisiae* (budding yeast), *Schizosaccharomyces pombe* (fission yeast), *Pichia pastoris*, and *Hansenula polymorpha* (methylotropic yeasts) may also be used. Filamentous ascomycetes, such as *Neurospora crassa* and *Aspergillus nidulans* may also be used. Plant cells such as those derived from Nicotiana and Arabidopsis are preferred. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York, Freeman & Co. 1990).

Concatemers

A concatemer is a series of linked units. In the present context a concatemer is used to denote a number of serially linked nucleotide cassettes, wherein at least two of the serially linked nucleotide units comprises a cassette having the basic structure $[rs_2\text{-SP-PR-X-TR-SP-}rs_1]$ wherein $rs_1$ and $rs_2$ together denote a restriction site, SP individually denotes a spacer of at least two nucleotide bases, PR denotes a promoter, capable of functioning in a cell, X denotes an expressible nucleotide sequence, TR denotes a terminator, and SP individually denotes a spacer of at least two nucleotide bases.

Optionally the cassettes comprise an intron sequence between the promoter and the expressible nucleotide sequence and/or between the terminator and the expressible sequence.

The expressible nucleotide sequence in the cassettes of the concatemer may comprise a DNA sequence selected from the group comprising cDNA and genomic DNA.

or monocots such as grasses, lilies, and orchids; from lower plants such as algae and gingko, from higher fungi such as terrestrial fruiting fungi, from marine actinomycetes. The expressible nucleotide sequences may also originate from protozoans such as malaria or trypanosomes, or from prokaryotes such as *E. coli* or archaebacteria. Furthermore, the expressible nucleotide sequences may originate from one or more preferably from more expression states from the species and genera listed in the table below.

| | |
|---|---|
| Bacteria | Streptomyces, Micromonospora, Norcadia, Actinomadura, Actinoplanes, Streptosporangium, Microbispora, Kitasatosporiam, Azobacterium, Rhizobium, Achromobacterium, Enterobacterium, Brucella, Micrococcus, Lactobacillus, Bacillus (B.t. toxins), Clostridium (toxins), Brevibacterium, Pseudomonas, Aerobacter, Vibrio, Halobacterium, Mycoplasma, Cytophaga, Myxococcus |
| Fungi | *Amanita muscaria* (fly agaric, ibotenic acid, muscimol), Psilocybe (psilocybin) Physarium, Fuligo, Mucor, Phytophtora, Rhizopus, Aspergillus, Penicillium (penicillin), Coprinus, Phanerochaete, Acremonium (Cephalosporin), Trochoderma, Helminthosporium, Fusarium, Alternaria, Myrothecium, Saccharomyces |
| Algae | *Digenea simplex* (kainic acid, antihelminthic), *Laminaria anqustata* (laminine, hypotensive) |
| Lichens | *Usnea fasciata* (vulpinicacid, antimicrobial; usnic acid, antitumor) |
| Higher Plants | Artemisia (artemisinin), Coleus (forskolin), Desmodium (K channel agonist), Catharanthus (Vinca alkaloids), Digitalis (cardiac glycosides), Podophyllum (podophyllotoxin), Taxus (taxol), Cephalotaxus (homoharringtonine), Camptotheca (Camptothecin), *Camellia sinensis* (Tea), *Cannabis indica*, *Cannabis sativa* (Hemp), *Erythroxylum coca* (Coca), *Lophophora williamsii* (Peyote *Myristica fragrans* (Nutmeg), Nicotiana, *Papaver somniferum* (Opium Poppy), *Phalaris arundinacea* (Reed canary grass) |
| Protozoa | *Ptychodiscus brevis*; Dinoflagellates (brevitoxin, cardiovascular) |
| Sponges | *Microciona prolifera* (ectyonin, antimicrobial) *Cryptotethya cryta* (D-arabino furanosides) |
| Coelenterata | Portuguese Man o War & other jellyfish and medusoid toxins. |
| Corals | Pseudoterogonia species (Pseudoteracins, anti-inflammatory), Erythropodium (erythrolides, anti-inflammatory) |
| Aschelminths | Nematode secretory compounds |
| Molluscs | Conus toxins, sea slug toxins, cephalapod neurotransmitters, squid inks |
| Annelida | *Lumbriconereis heteropa* (nereistoxin, insecticidal) |
| Arachnids | Dolomedes ("fishing spider" venoms) |
| Crustacea | Xenobalanus (skin adhesives) |
| Insects | Epilachna (mexican bean beetle alkaloids) |
| Spinunculida | *Bonellia viridis* (bonellin, neuroactive) |
| Bryozoans | *Bugula neritina* (bryostatins, anti cancer) |
| Echinoderms | Crinoid chemistry |
| Tunicates | *Trididemnum solidum* (didemnin, anti-tumor and anti-viral; *Ecteinascidia turbinata* ecteinascidins, anti-tumor) |
| Vertebrates | *Eptatretus stoutii* (eptatretin, cardioactive), *Trachinus draco* (proteinaceous toxins, reduce blood pressure, respiration and reduce heart rate). Dendrobatid frogs (batrachotoxins, pumiliotoxins, histrionicotoxins, and other polyamines); Snake venom toxins; *Orinthorhynohus anatinus* (duck-billed platypus venom), modified carotenoids, retinoids and steroids; Avians: histrionicotoxins, modified carotenoids, retinoids and steroids |

According to one aspect of the invention, a concatemer comprises cassettes with expressible nucleotide from different expression states, so that non-naturally occurring combinations or non-native combinations of expressible nucleotide sequences are obtained. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

For example, the expressible nucleotide sequences may originate from eukaryots such as mammals such as humans, mice or whale, from reptiles such as snakes crocodiles or turtles, from tunicates such as sea squirts, from *lepidoptera* such as butterflies and moths, from coelenterates such as jellyfish, anenomes, or corals, from fish such as bony and cartilaginous fish, from plants such as dicots, e.g. coffee, oak According to a preferred embodiment of the invention the concatemer comprises at least a first cassette and a second cassette, said first cassette being different from said second cassette. More preferably, the concatemer comprises cassettes, wherein substantially all cassettes are different. The difference between the cassettes may arise from differences between promoters, and/or expressible nucleotide sequences, and/or spacers, and/or terminators, and/or introns.

The number of cassettes in a single concatemer is largely determined by the host species into which the concatemer is eventually to be inserted and the vector through which the insertion is carried out. The concatemer thus may comprise at least 10 cassettes, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000 cassettes.

Each of the cassettes may be laid out as described above.

Once the concatemer has been assembled or concatenated it may be ligated into a suitable vector. Such a vector may advantageously comprise an artificial chromosome. The basic requirements for a functional artificial chromosome have been described in U.S. Pat. No. 4,464,472, the contents of which is hereby incorporated by reference. An artificial chromosome or a functional minichromosome, as it may also be termed must comprise a DNA sequence capable of replication and stable mitotic maintenance in a host cell comprising a DNA segment coding for centromere-like activity during mitosis of said host and a DNA sequence coding for a replication site recognized by said host.

Suitable artificial chromosomes include a Yeast Artificial Chromosome (YAC) (see e.g. Murray et al, Nature 305:189-193; or U.S. Pat. No. 4,464,472), a mega Yeast Artificial Chromosome (mega YAC), a Bacterial Artificial Chromosome (BAC), a mouse artificial chromosome, a Mammalian Artificial Chromosome (MAC) (see e.g. U.S. Pat. No. 6,133,503 or U.S. Pat. No. 6,077,697), an Insect Artificial Chromosome (BUGAC), an Avian Artificial Chromosome (AVAC), a Bacteriophage Artificial Chromosome, a Baculovirus Artificial Chromosome, a plant artificial chromosome (U.S. Pat. No. 5,270,201), a BIBAC vector (U.S. Pat. No. 5,977,439) or a Human Artificial Chromosome (HAC).

The artificial chromosome is preferably so large that the host cell perceives it as a "real" chromosome and maintains it and transmits it as a chromosome. For yeast and other suitable host species, this will often correspond approximately to the size of the smallest native chromosome in the species. For Saccharomyces, the smallest chromosome has a size of 225 Kb.

MACs may be used to construct artificial chromosomes from other species, such as insect and fish species. The artificial chromosomes preferably are fully functional stable chromosomes. Two types of artificial chromosomes may be used. One type, referred to as SATACs [satellite artificial chromosomes] are stable heterochromatic chromosomes, and the other type are minichromosomes based on amplificaton of euchromatin.

Mammalian artificial chromosomes provide extra-genomic specific integration sites for introduction of genes encoding proteins of interest and permit megabase size DNA integration, such as integration of concatemers according to the invention.

According to another embodiment of the invention, the concatemer may be integrated into the host chromosomes or cloned into other types of vectors, such as a plasmid vector, a phage vector, a viral vector or a cosmid vector.

A preferable artificial chromosome vector is one that is capable of being conditionally amplified in the host cell, e.g. in yeast. The amplification preferably is at least a 10 fold amplification. Furthermore, it is advantageous that the cloning site of the artificial chromosome vector can be modified to comprise the same restriction site as the one bordering the cassettes described above, i.e. RS2 and/or RS2'.

Concatenation

Cassettes to be concatenated are normally excised from a vector either by digestion with restriction enzymes or by PCR. After excision the cassettes may be separated from the vector through size fractionation such as gel filtration or through tagging of known sequences in the cassettes. The isolated cassettes may then be joined together either through interaction between sticky ends or through ligation of blunt ends.

Single-stranded compatible ends may be created by digestion with restriction enzymes. For concatenation a preferred enzyme for excising the cassettes would be a rare cutter, i.e. an enzyme that recognises a sequence of 7 or more nucleotides. Examples of enzymes that cut very rarely are the meganucleases, many of which are intron encoded, like e.g. I-Ceu I, I-Sce I, I-Ppo I, and PI-Psp I (see example 6d for more). Other preferred enzymes recognize a sequence of 8 nucleotides like e.g. Asc I, AsiS I, CciN I, CspB I, Fse I, MchA I, Not I, Pac I, Sbf I, Sda I, Sgf I, SgrA I, Sse232 I, and Sse8387 I, all of which create single stranded, palindromic compatible ends.

Other preferred rare cutters, which may also be used to control orientation of individual cassettes in the concatemer are enzymes that recognize non-palindromic sequences like e.g. Aar I, Sap I, Sfi I, Sdi I, and Vpa (see example 6c for more).

Alternatively, cassettes can be prepared by the addition of restriction sites to the ends, e.g. by PCR or ligation to linkers (short synthetic dsDNA molecules). Restriction enzymes are continuously being isolated and characterised and it is anticipated that many of such novel enzymes can be used to generate single-stranded compatible ends according to the present invention.

It is conceivable that single stranded compatible ends can be made by cleaving the vector with synthetic cutters. Thus, a reactive chemical group that will normally be able to cleave DNA unspecifically can cut at specific positions when coupled to another molecule that recognises and binds to specific sequences. Examples of molecules that recognise specific dsDNA sequences are DNA, PNA, LNA, phosphothioates, peptides, and amides. See e.g. Armitage, B. (1998) Chem. Rev. 98: 1171-1200, who describes photocleavage using e.g. anthraquinone and UV light; Dervan P. B. & Bürli R. W. (1999) Curr. Opin. Chem. Biol. 3: 688-93 describes the specific binding of polyamides to DNA; Nielsen, P. E. (2001) Curr. Opin. Biotechnol. 12: 16-20 describes the specific binding of PNA to DNA, and Chemical Reviews special thematic issue: RNA/DNA Cleavage (1998) vol. 98 (3) Bashkin J. K. (ed.) ACS publications, describes several examples of chemical DNA cleavers.

Single-stranded compatible ends may also be created by using e.g. PCR primers including dUTP and then treating the PCR product with Uracil-DNA glycosylase (Ref: U.S. Pat. No. 5,035,996) to degrade part of the primer. Alternatively, compatible ends can be created by tailing both the vector and insert with complimentary nucleotides using Terminal Transferase (Chang, L M S, Bollum T J (1971) J Biol Chem 246: 909).

It is also conceivable that recombination can be used to generate concatemers, e.g. through the modification of techniques like the Creator™ system (Clontech) which uses the Cre-loxP mechanism (Sauer B 1993 Methods Enzymol 225: 890-900) to directionally join DNA molecules by recombination or like the Gateway™ system (Life Technologies, U.S. Pat. No. 5,888,732) using lambda aft attachment sites for directional recombination (Landy A 1989, Ann Rev Biochem 58:913). It is envisaged that also lambda cos site dependent systems can be developed to allow concatenation.

More preferably the cassettes may be concatenated without an intervening purification step through excision from a vector with two restriction enzymes, one leaving sticky ends on the cassettes and the other one leaving blunt ends in the vectors. This is the preferred method for concatenation of cassettes from vectors having the basic structure of [RS1-RS2-SP-PR-X-TR-SP-RS2'-RS1'].

An alternative way of producing concatemers free of vector sequences would be to PCR amplify the cassettes from a single-stranded primary vector. The PCR product must include the restriction sites RS2 and RS2' which are subsequently cleaved by its cognate enzyme(s). Concatenation can then be performed using the digested PCR product, essentially without interference from the single stranded primary vector template or the small double stranded fragments, which have been cut from the ends.

Figure 1:
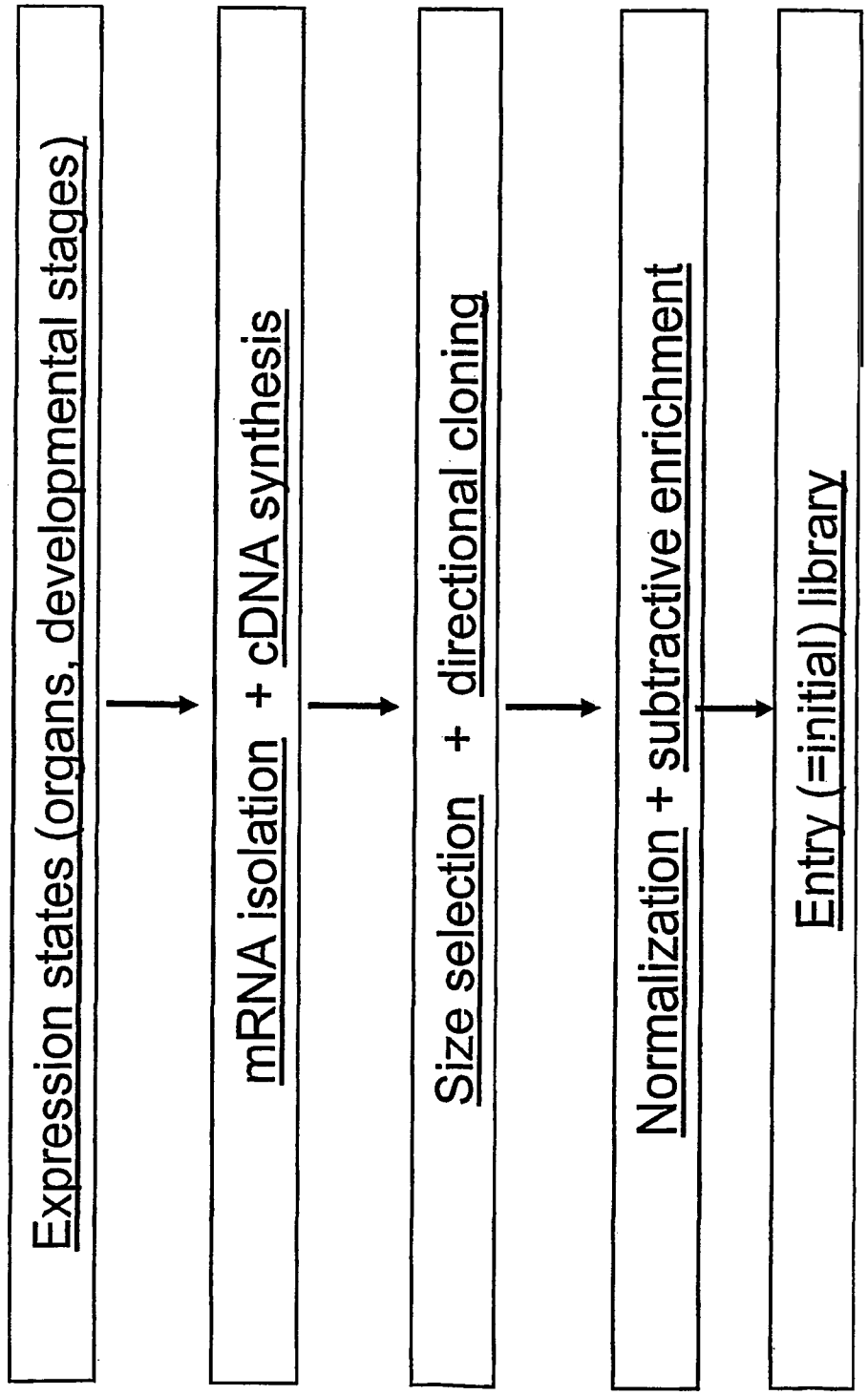
FIG. 1 shows a flow chart of the steps leading from an expression state to incorporation of the expressible nucleotide sequences in an entry library (a nucleotide library according to the invention).
Figure 2A:
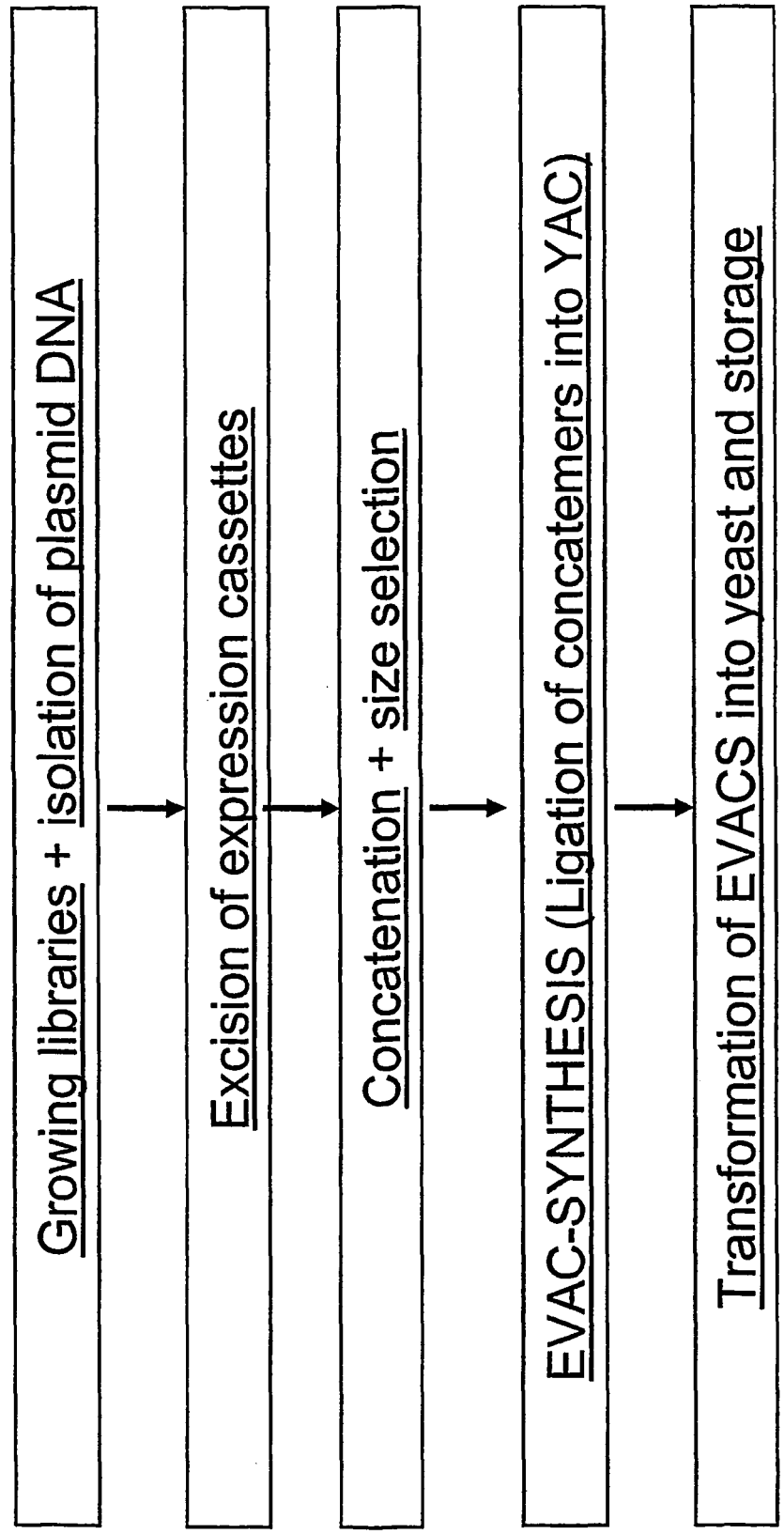
FIG. 2a shows one way of producing the EVACs which includes concatenation, size selection and insertion into an artificial chromosome vector.

The concatemer may be assembled or concatenated by concatenation of at least two cassettes of nucleotide sequences each cassette comprising a first sticky end, a spacer sequence, a promoter, an expressible nucleotide sequence, a terminator, a spacer sequence, and a second sticky end. A flow chart of the procedure is shown in FIG. 2a.

Preferably concatenation further comprises
starting from a primary vector [RS1-RS2-SP-PR-X-TR-SP-RS2'-RS1'],
wherein X denotes an expressible nucleotide sequence,
RS1 and RS1' denote restriction sites,
RS2 and RS2' denote restriction sites different from RS1 and RS1',
SP individually denotes a spacer sequence of at least two nucleotides,
PR denotes a promoter,
TR denotes a terminator,
i) cutting the primary vector with the aid of at least one restriction enzyme specific for RS2 and RS2' obtaining cassettes having the general formula [$rs_2$-SP-PR-X-TR-SP-$rs_1$] wherein $rs_1$ and $rs_2$ together denote a functional restriction site RS2 or RS2',
ii) assembling the cut out cassettes through interaction between $rs_1$ and $rs_2$.

In this way at least 10 cassettes can be concatenated, such as at least 15, for example at least 20, such as at least 25, for example at least 30, such as from 30 to 60 or more than 60, such as at least 75, for example at least 100, such as at least 200, for example at least 500, such as at least 750, for example at least 1000, such as at least 1500, for example at least 2000.

Figure 2B:
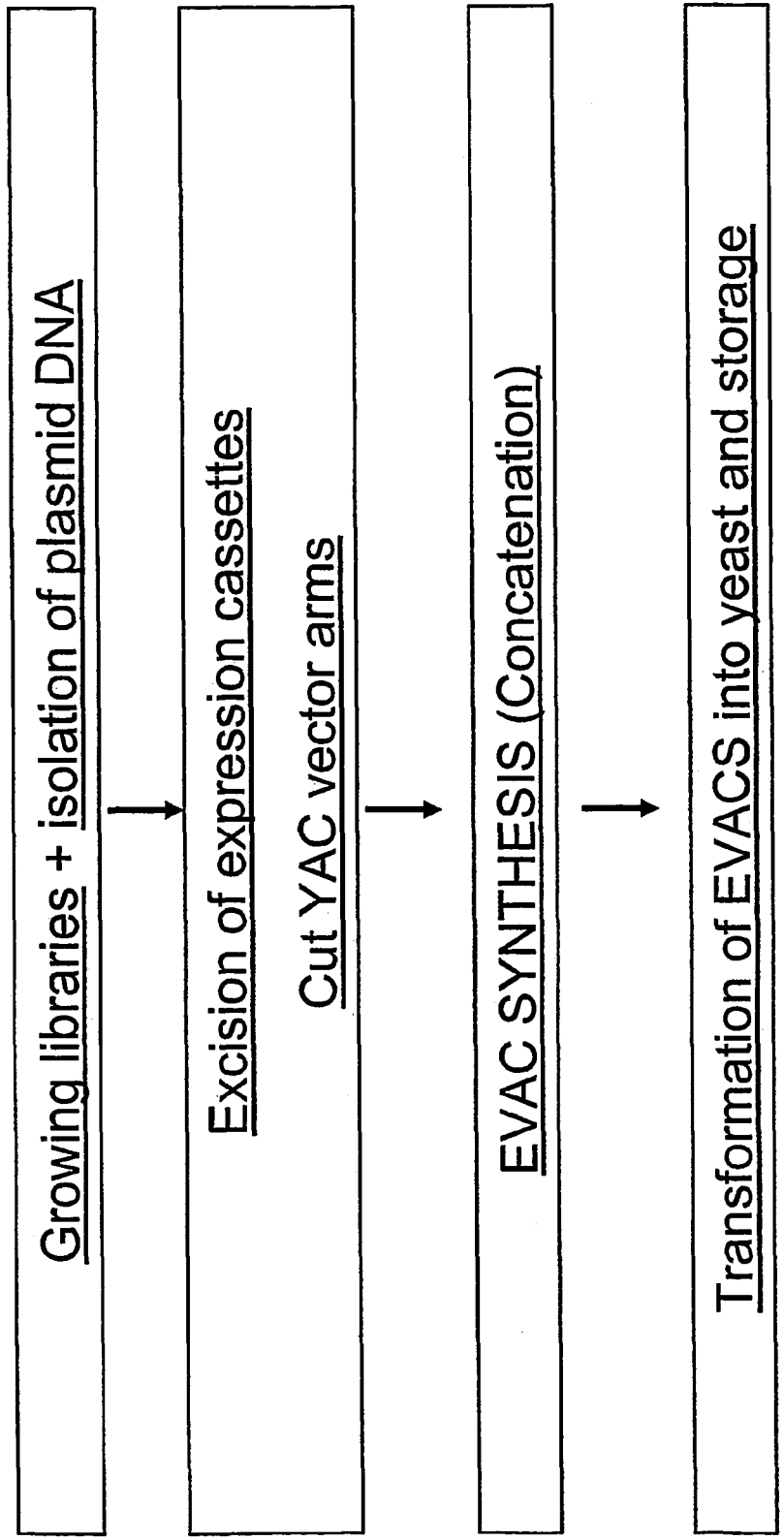
FIG. 2b shows a one step procedure for concatenation and ligation of vector arms to obtain EVACs.
Figure 7:
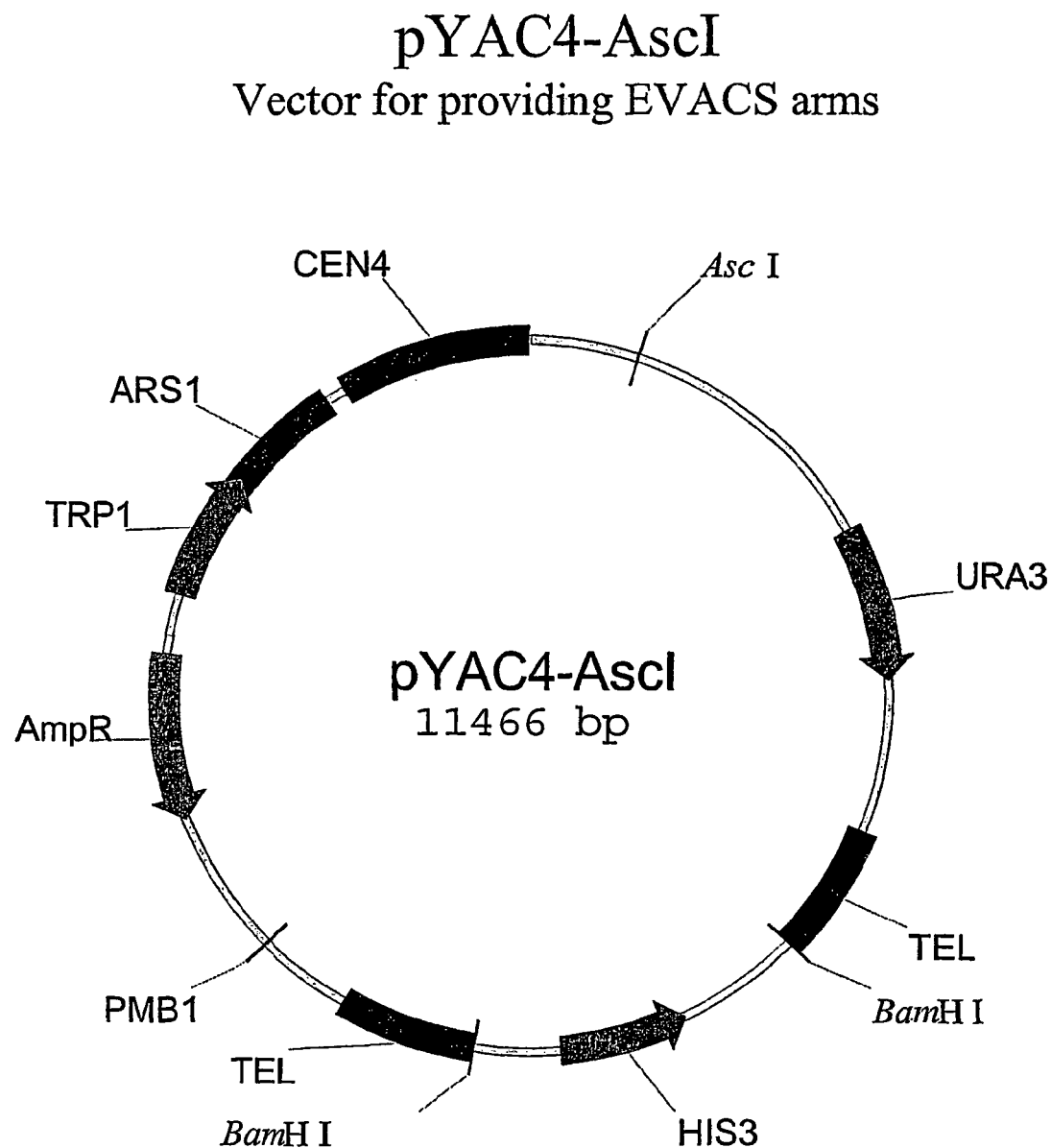
FIG. 7 shows a vector (pYAC4-AscI) for providing arms for an evolvable artificial chromosome (EVAC) into which a concatemer according to the invention can be cloned. TRP1, URA3, and HIS3 are yeast auxotrophic marker genes, and AmpR is an E. coli antibiotic marker gene. CEN4 is a centromere and TEL are telomeres. ARS1 and PMB1 allow replication in yeast and E. coli respectively. BamH I and Asc I are restriction enzyme recognition sites. The nucleotide sequence of the vector is set forth in SEQ ID NO 4.

According to an especially preferred embodiment, vector arms each having a RS2 or RS2' in one end and a non-complementary overhang or a blunt end in the other end are added to the concatenation mixture together with the cassettes described above to further simplify the procedure (see FIG. 2b). One example of a suitable vector for providing vector arms is disclosed in FIG. 7 TRP1, URA3, and HIS3 are auxotrophic marker genes, and AmpR is an E. coli antibiotic marker gene. CEN4 is a centromer and TEL are telomeres. ARS1 and PMB1 allow replication in yeast and E. coli respectively. BamH I and Asc I are restriction enzyme recognition sites. The nucleotide sequence of the vector is set forth in SEQ ID NO 4. The vector is digested with BamHI and AscI to liberate the vector arms, which are used for ligation to the concatemer.

Figure 8:
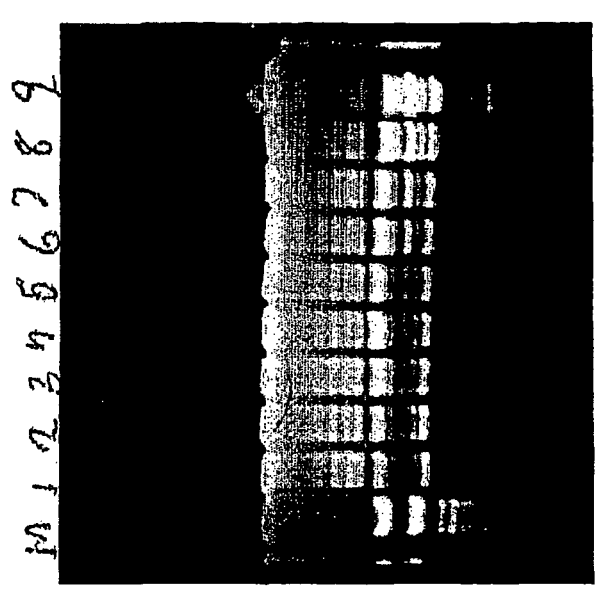
FIG. 8. shows the general concatenation strategy. On the left is shown a circular entry vector with restriction sites, spacers, promoter, expressible nucleotide sequence and terminator. These are excised and ligated randomly.
Figure 8:
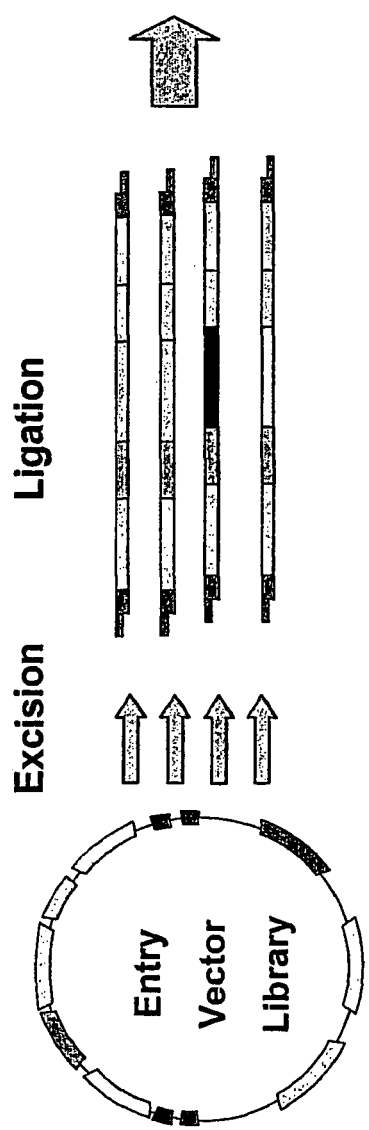

The ratio of vector arms to cassettes determines the maximum number of cassettes in the concatemer as illustrated in FIG. 8. The vector arms preferably are artificial chromosome vector arms such as those described in FIG. 7.

It is of course also possible to add stopper fragments to the concatenation solution, the stopper fragments each having a RS2 or RS2' in one end and a non-complementary overhang or a blunt end in the other end. The ratio of stopper fragments to cassettes can likewise control the maximum size of the concaterner.

The complete sequence of steps to be taken when starting with the isolation of mRNA until inserting into an entry vector may include the following steps
i) isolating mRNA from an expression state;
ii) obtaining substantially full length cDNA corresponding to the mRNA sequences,
iii) inserting the substantially full length cDNA into a cloning site in a cassette in a primary vector, said cassette being of the general formula in 5'→3' direction:

[RS1-RS2-SP-PR-CS-TR-SP-RS2'-RS1']

wherein CS denotes a cloning site.

In preparation of the concatemer, genes may be isolated from different entry libraries to provide the desired selection of genes. Accordingly, concatenation may further comprise selection of vectors having expressible nucleotide sequences from at least two different expression states, such as from two different species. The two different species may be from two different classes, such as from two different divisions, more preferably from two different sub-kingdoms, such as from two different kingdoms.

As an alternative to including vector arms in the concatenation reaction it is possible to ligate the concatemer into an artificial chromosome selected from the group comprising yeast artificial chromosome, mega yeast artificial chromosome, bacterial artificial chromosome, mouse artificial chromosome, human artificial chromosome.

Preferably at least one inserted concatemer further comprises a selectable marker. The marker(s) are conveniently not included in the concatemer as such but rather in an artificial chromosome vector, into which the concatemer is inserted. Selectable markers generally provide a means to select, for growth, only those cells which contain a vector. Such markers are of two types: drug resistance and auxotrophy. A drug resistance marker enables cells to grow in the presence of an otherwise toxic compound. Auxotrophic markers allow cells to grow in media lacking an essential component by enabling cells to synthesise the essential component (usually an amino acid).

Illustrative and non-limiting examples of common compounds for which selectable markers are available with a brief description of their mode of action follow:
Prokaryotic
   Ampicillin: interferes with a terminal reaction in bacterial cell wall synthesis. The resistance gene (bla) encodes beta-lactamase which cleaves the beta-lactam ring of the antibiotic thus detoxifying it.
   Tetracycline: prevents bacterial protein synthesis by binding to the 30S ribosomal subunit. The resistance gene (tet) specifies a protein that modifies the bacterial membrane and prevents accumulation of the antibiotic in the cell.
   Kanamycin: binds to the 70S ribosomes and causes misreading of messenger RNA. The resistant gene (npth) modifies the antibiotic and prevents interaction with the ribosome.
   Streptomycin: binds to the 30S ribosomal subunit, causing misreading of messenger RNA. The resistance gene (Sm) modifies the antibiotic and prevents interaction with the ribosome.
   Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.
Eukaryotic
   Hygromycin: a aminocyclitol that inhibits protein synthesis by disrupting ribosome translocation and promoting mistranslation. The resistance gene (hph) detoxifies hygromycin-B-phosphorylation.

Histidinol: cytotoxic to mammalian cells by inhibiting histidyl-tRNA synthesis in histidine free media. The resistance gene (hisD) product inactivates histidinol toxicity by converting it to the essential amino acid, histidine.

Neomycin (G418): blocks protein synthesis by interfering with ribosomal functions. The resistance gene ADH encodes amino glycoside phosphotransferase which detoxifies G418.

Uracil: Laboratory yeast strains carrying a mutated gene which encodes orotidine-5'-phosphate decarboxylase, an enzyme essential for uracil biosynthesis, are unable to grow in the absence of exogenous uracil. A copy of the wild-type gene (ura4+, *S. pombe* or URA3 *S. cerevisiae*) carried on the vector will complement this defect in transformed cells.

Adenosine: Laboratory strains carrying a deficiency in adenosine synthesis may be complemented by a vector carrying the wild type gene, ADE 2.

Amino acids: Vectors carrying the wild-type genes for LEU2, TRP 1, HIS 3 or LYS 2 may be used to complement strains of yeast deficient in these genes.

Zeocin: this new bleomycin-family antibiotic intercalates into the DNA and cleaves it. The Zeocin resistance gene encodes a 13,665 dalton protein. This protein confers resistance to Zeocin by binding to the antibiotic and preventing it from binding DNA. Zeocin is effective on most aerobic cells and can be used for selection in mammalian cell lines, yeast, and bacteria.

Transgenic Cells

In one aspect of the invention, the concatemers comprising the multitude of cassettes are introduced into a host cell, in which the concatemers can be maintained and the expressible nucleotide sequences can be expressed in a co-ordinated way. The cassettes comprised in the concatemers may be isolated from the host cell and re-assembled due to their uniform structure with—preferably—concatemer restriction sites between the cassettes.

The host cells selected for this purpose are preferably cultivable under standard laboratory conditions using standard culture conditions, such as standard media and protocols. Preferably the host cells comprise a substantially stable cell line, in which the concatemers can be maintained for generations of cell division. Standard techniques for transformation of the host cells and in particular methods for insertion of artificial chromosomes into the host cells are known.

It is also of advantage if the host cells are capable of undergoing meiosis to perform sexual recombination. It is also advantageous that meiosis is controllable through external manipulations of the cell culture. One especially advantageous host cell type is one where the cells can be manipulated through external manipulations into different mating types.

The genome of a number of species have already been sequenced more or less completely and the sequences can be found in databases. The list of species for which the whole genome has been sequenced increases constantly. Preferably the host cell is selected from the group of species, for which the whole genome or essentially the whole genome has been sequenced. The host cell should preferably be selected from a species that is well described in the literature with respect to genetics, metabolism, physiology such as model organism used for genomics research.

The host organism should preferably be conditionally deficient in the abilities to undergo homologous recombination. The host organism should preferably have a codon usage similar to that of the donor organisms. Furthermore, in the case of genomic DNA, if eukaryotic donor organisms are used, it is preferable that the host organism has the ability to process the donor messenger RNA properly, e.g., splice out introns.

The host cells can be bacterial, archaebacteria, or eukaryotic and can constitute a homogeneous cell line or mixed culture. Suitable cells include the bacterial and eukaryotic cell lines commonly used in genetic engineering and protein expression.

Preferred prokaryotic host organisms may include but are not limited to *Escherichia coli*, *Bacillus subtilis*, *B licehniformis*, *B. cereus*, *Streptomyces lividans*, *Streptomyces coelicolor*, *Pseudomonas aeruginosa*, *Myxococcus xanthus*. *Rhodococcus*, *Streptomycetes*, *Actinomycetes*, *Corynebacteria*, *Bacillus*, *Pseudomonas*, *Salmonella*, and *Erwinia*. The complete genome sequences of *E. coli* and *Bacillus subtilis* are described by Blattner et al., Science 277, 1454-1462 (1997); Kunst et al., Nature 390, 249-256 (1997)).

Preferred eukaryotic host organisms are mammals, fish, insects, plants, algae and fungi.

Examples of mammalian cells include those from, e.g., monkey, mouse, rat, hamster, primate, and human, both cell lines and primary cultures. Preferred mammalian host cells include but are not limited to those derived from humans, monkeys and rodents, such as chinese hamster ovary (CHO) cells, NIH/3T3, COS, 293, VERO, HeLa etc (see Kriegler M. in "Gene Transfer and Expression: A Laboratory Manual", New York, Freeman & Co. 1990), and stem cells, including embryonic stem cells and hemopoietic stem cells, zygotes, fibroblasts, lymphocytes, kidney, liver, muscle, and skin cells.

Examples of insect cells include baculo lepidoptera.

Examples of plant cells include maize, rice, wheat, cotton, soybean, and sugarcane. Plant cells such as those derived from Nicotiana and Arabidopsis are preferred Examples of fungi include penicillium, aspergillus, such as *Aspergillus nidulans*, podospora, neurospora, such as *Neurospora crassa*, saccharomyces, such as *Saccharomyces cerevisiae* (budding yeast), Schizosaccharomyces, such as *Schizosaccharomyces pombe* (fission yeast), Pichia spp, such as *Pichia pastoris*, and *Hansenula polymorpha* (methylotropic yeasts).

In a preferred embodiment the host cell is a yeast cell, and an illustrative and not limiting list of suitable yeast host cells comprise: baker's yeast, *Kluyveromyces marxianus*, *K. lactis*, *Candida utilis*, *Phaffia rhodozyma*, *Saccharomyces boulardii*, *Pichia pastoris*, *Hansenula polymorpha*, *Yarrowia lipolytica*, *Candida paraffinica*, *Schwanniomyces castellii*, *Pichia stipitis*, *Candida shehatae*, *Rhodotorula glutinis*, *Lipomyces lipofer*, *Cryptococcos curvatus*, *Candida* spp. (e.g. *C. palmioleophila*), *Yarrowia lipolytica*, *Candida guilliermondii*, *Candida*, *Rhodotorula* spp., *Saccharomycopsis* spp., *Aureobasidium pullulans*, *Candida brumptii*, *Candida hydrocarbofumarica*, *Torulopsis*, *Candida tropicalis*, *Saccharomyces cerevisiae*, *Rhodotorula rubra*, *Candida flaveri*, *Eremothecium ashbyii*, *Pichia* spp., *Pichia pastoris*, *Kluyveromyces*, *Hansenula*, *Kloeckera*, *Pichia*, *Pachysolen* spp., or *Torulopsis bornbicola*.

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. Particularly advantageous hosts are *E. coli*, lactobacilli, Streptomycetes, Actinomycetes, Saccharomyces and filamentous fungi.

In any one host cell it is possible to make all sorts of combinations of expressible nucleotide sequences from all possible sources. Furthermore, it is possible to make combinations of promoters and/or spacers and/or introns and/or terminators in combination with one and the same expressible nucleotide sequence.

Thus in any one cell there may be expressible nucleotide sequences from two different expression states. Furthermore, these two different expression states may be from one species or advantageously from two different species. Any one host cell may also comprise expressible nucleotide sequences from at least three species, such as from at least four, five, six, seven, eight, nine or ten species, or from more than 15 species such as from more than 20 species, for example from more than 30, 40 or 50 species, such as from more than 100 different species, for example from more than 300 different species, such as form more than 500 different species, for example from more than 1000 different species, thereby obtaining combinations of large numbers of expressible nucleotide sequences from a large number of species. In this way potentially unlimited numbers of combinations of expressible nucleotide sequences can be combined across different expression states. These different expression states may represent at least two different tissues, such as at least two organs, such as at least two species, such as at least two genera. The different species may be from at least two different phylae, such as from at least two different classes, such as from at least two different divisions, more preferably from at least two different sub-kingdoms, such as from at least two different kingdoms.

Any two of these species may be from two different classes, such as from two different divisions, more preferably from two different sub-kingdoms, such as from two different kingdoms. Thus expressible nucleotide sequences may be combined from a eukaryot and a prokaryot into one and the same cell.

According to another embodiment of the invention, the expressible nucleotide sequences may be from one and the same expression state. The products of these sequences may interact with the products of the genes in the host cell and form new enzyme combinations leading to novel biochemical pathways. Furthermore, by putting the expressible nucleotide sequences under the control of a number of promoters it becomes possible to switch on and off groups of genes in a co-ordinated manner. By doing this with expressible nucleotide sequences from only one expression states, novel combinations of genes are also expressed.

The number of concatemers in one single cell may be at least one concatemer per cell, preferably at least 2 concatemers per cell, more preferably 3 per cell, such as 4 per cell, more preferably 5 per cell, such as at least 5 per cell, for example at least 6 per cell, such as 7, 8, 9 or 10 per cell, for example more than 10 per cell. As described above, each concatemer may preferably comprise up to 1000 cassettes, and it is envisages that one concatemer may comprise up to 2000 cassettes. By inserting up to 10 concatemers into one single cell, this cell may thus be enriched with up to 20,000 heterologous expressible genes, which under suitable conditions may be turned on and off by regulation of the regulatable promoters.

Often it is more preferable to provide cells having anywhere between 10 and 1000 heterologous genes, such as 20-900 heterologous genes, for example 30 to 800 heterologous genes, such as 40 to 700 heterologous genes, for example 50 to 600 heterologous genes, such as from 60 to 300 heterologous genes or from 100 to 400 heterologous genes which are inserted as 2 to 4 artificial chromosomes each containing one concatemer of genes. The genes may advantageously be located on 1 to 10 such as from 2 to 5 different concatemers in the cells. Each concatemer may advantageously comprise from 10 to 1000 genes, such as from 10 to 750 genes, such as from 10 to 500 genes, such as from 10 to 200 genes, such as from 20 to 100 genes, for example from 30 to 60 genes, or from 50 to 100 genes.

The concatemers may be inserted into the host cells according to any known transformation technique, preferably according to such transformation techniques that ensure stable and not transient transformation of the host cell. The concatemers may thus be inserted as an artificial chromosome which is replicated by the cells as they divide or they may be inserted into the chromosomes of the host cell. The concatemer may also be inserted in the form of a plasmid such as a plasmid vector, a phage vector, a viral vector, a cosmid vector, that is replicated by the cells as they divide. Any combination of the three insertion methods is also possible. One or more concatemers may thus be integrated into the chromosome(s) of the host cell and one or more concatemers may be inserted as plasmids or artificial chromosomes. One or more concatemers may be inserted as artificial chromosomes and one or more may be inserted into the same cell via a plasmid.

EXAMPLES

Example 1

In the examples 1-3 an Asc1 site was introduced into the EcoR1 site in pYAC4 (Sigma, Burke D T et al. 1987, Science vol 236, p 806), so that sticky ends match the Asc1 site(=RS2 in general formula of this patent) of the cassettes in pEVE vectors
Preparation of EVACs (EVolvable Artificial Chromosomes) Including Size Fractioning
Preparation of pYAC4-Asc Arms
1. inoculate 150 ml of LB (sigma) with a single colony of *E. coli* DH5α containing pYAC4-Asc
2. grow to OD600~1, harvest cells and make plasmid preparation
3. digest 100 µg pYAC4-Asc w. BamH1 and Asc1
4. dephosphorylate fragments and heat inactivate phosphatase (20 min, 80 C)
5. purify fragments (e.g. Qiaquick Gel Extraction Kit)
6. run 1% agarose gel to estimate amount of fragment
Preparation of Expression Cassettes
1. take 100 µg of plasmid preparation from each of the following libraries
   a) pMA-CAR
   b) pCA-CAR
   c) Phaffia cDNA library
   d) Carrot cDNA library
2. digest w. Srf1 (10 units/prep, 37 C overnight)
3. dephosphorylate (10 units/prep, 37 C, 2 h)
4. heat inactivate 80 C, 20 min
5. concentrate and change buffer (precipitation or ultra filtration),
6. digest w. Asc1. (10 units/prep, 37 C, overnight)
7. adjust volume of preps to 100 µL
Preparation of EVACs Different types of EVACs have been made by varying the ratio of the different libraries that goes into the ligation reaction.

| EVAC | pMA-CAR | pCA-CAR | Phaffia cDNA | Carrot cDNA |
|------|---------|---------|--------------|-------------|
| A    | 40%     | 40%     | 10%          | 10%         |
| B    | 25%     | 25%     | 25%          | 25%         |

1. add ~100 ng arms of pYAC4-Asc/100 μg of cassette mixture
2. concentrate to <33.5 μL
3. add 2.5 units of T4 DNA-ligase+4 μL 10× ligase buffer. Adjust to 40 μL
4. ligate 3 h, 16 C
5. stop reaction by adding 2 μL of 500 mM EDTA
6. bring reaction volume to 125 μL, add 25 μL loading mix, heat at 60 C for 5 min
7. distribute evenly in 10 wells of a 1% LMP agarose gel
8. run pulsed field gel (CHEF III, 1% LMP agarose, ½ strength TBE (BioRad), angle 120, temperature 12 C, voltage 5.6 V/cm, switch time ramping 5-25 s, run time 30 h)
9. stain part of the gel that contains molecular weight markers+1 sample lane for quality check
10. cut remaining 9 sample lanes corresponding to mw. 97-194 kb (fraction 1); 194-291 kb (fraction 2); 291-365 kb (fraction 3) from the gel
11. agarase gel in high NaCl agarase buffer. 1 u agarase/100 μg gel. 40 C 3 h
12. concentrate preparation to <20 μL
13. transform suitable yeast strain w. preparation using alkali/cation transformation
14. plate on selective minimal media plates
15. incubate 30 C for 4-5 days
16. pick colonies
17. analyse colonies Example 2

Preparation of EVACs (EVolvable Artificial Chromosomes) with Direct Transformation Preparation of pYAC4-Asc Arms
1. inoculate 150 ml of LB with a single colony of DH5α containing pYAC4-Asc
2. grow to OD600~1, harvest cells and make plasmid preparation
3. digest 100 μg pYAC4-Asc w. BamH1 and Asc1
4. dephosphorylate fragments and heat inactivate phosphatase (20 min, 80 C)
5. purify fragments (e.g. Qiaquick Gel Extraction Kit)
1. run 1% agarose gel to estimate amount of fragment
Preparation of Expression Cassettes
1. take 100 μg of plasmid preparation from each of the following libraries
  e) pMA-CAR
  f) pCA-CAR
  g) Phaffia cDNA library
  h) Carrot cDNA library
2. digest w. Srf1 (10 units/prep, 37 C overnight)
3. dephosphorylate (10 units/prep, 37 C, 2 h)
4. heat inactivate 80 C, 20 min
5. concentrate and change buffer (precipitation or ultra filtration),
6. digest w. Asc1. (10 units/prep, 37 C, overnight)
7. adjust volume of preps to 100 μL
Preparation of EVACs Different types of EVACs have been made by varying the ratio of the different libraries that goes into the ligation reaction.

| EVAC | pMA-CAR | pCA-CAR | Phaffia cDNA | Carrot cDNA |
|---|---|---|---|---|
| A | 40% | 40% | 10% | 10% |
| B | 25% | 25% | 25% | 25% |

1. concentrate to <32 μL
2. add 1 unit of T4 DNA-ligase+4 μL 10× ligase buffer. Adjust to 40 μL
3. ligate 2 h, 16 C
4. stop reaction by adding 2 μL of 500 mM EDTA, heat inactivate 60 C, 20 min
5. bring reaction volume to 500 μL with dH$_2$O, concentrate to 30 μL
6. add 10 U Asc1, 4 μL 10×Asc1 buffer, bring to 40 μL
7. incubate at 37 C for 1 h (alternatively 15 min 30 min)
8. heat inactivate 60 C, 20 min
9. add 2 μg YAC4-Asc arms, 1 U T4 DNA ligase, 10 μL 10× ligase buffer, bring to 100 μL
10. incubate ON, 16 C
11. add water to 500 μL
12. concentrate to 25 μL
13. transform suitable yeast strain w. preparation using alkali/cation transformation or other suitable transformation method
14. plate on selective minimal media plates
15. incubate 30 C for 4-5 days
16. pick colonies
17. analyse colonies Example 3

Preparation of EVACs (EVolvable Artificial Chromosomes) (Small Scale Preparation)

Preparation of Expression Cassettes
1. inoculate 5 ml of LB-medium (Sigma) with library inoculum corresponding to a 10+ fold representation of library. Grow overnight
2. make plasmid miniprep from 1.5 ml of culture (E.g. Qiaprep spin miniprep kit)
3. digest plasmid W. Srf 1
4. dephosphorylate fragments and heat inactivate phosphatase (20 min, 80 C)
5. digest w. Asc1
6. run 1/10 of reaction in 1% agarose to estimate amount of fragment
Preparation of pYAC4-Asc Arms
1. inoculate 150 ml of LB with a single colony of *E. coli* DH5α containing pYAC4-Asc
2. grow to OD600~1, harvest cells and make plasmid preparation
3. digest 100 μg pYAC4-Asc w. BamH1 and Asc1
4. dephosphorylate fragments and heat inactivate phosphatase (20 min, 80 C)
5. purify fragments (E.g. Qiaquick Gel Extraction Kit)
6. run 1% agarose gel to estimate amount of fragment
Preparation of EVACs
1. mix expression cassette fragments with YAC-arms so that cassette/arm ration is ~1000/1
2. if needed concentrate mixture (use e.g. Microcon YM30) so fragment concentration >75 ng/μL reaction
3. add 1 U T4 DNA ligase, incubate 16 C, 1-3 h. Stop reaction by adding 1 μL of 500 mM EDTA 4. run pulsed field gel (CHEF III, 1% LMP agarose, ½ strength TBE, angle 120, temperature 12 C, voltage 5.6 V/cm, switch time ramping 5-25 s, run time 30 h) Load sample in 2 lanes.
5. stain part of the gel that contains molecular weight markers
6. cut sample lanes corresponding to mw. 100-200 kb
7. agarase gel in high NaCl agarase buffer. 1 U agarase/100 mg gel
8. concentrate preparation to <20 μL
9. transform suitable yeast strain w. preparation using electroporation
10. plate on selective minimal media plates
11. incubate 30 C for 4-5 days
12. pick colonies

Example 4 cDNA Libraries Used in the Production of EVACs

1. *Daucus carota*, carrot root library:
   Full length
   Oligo dT primed, directional cDNA library
   cDNA library made using a pool of 3 Evolva EVE 4, 5 & 8 vectors (FIGS. 4, 5, 6)
   Number of independent clones: $41.6 \times 10^6$
   Average size: 0.9-2.9 kb
   Number of different genes present: 5000-10000
2. *Xanthophyllomyces dendrorhous*, (yeast), hole organism library
   Full length
   Oligo dT primed, directional cDNA library
   cDNA library made using a pool of 3 Evolva EVE 4, 5 & 8 vectors (FIGS. 4, 5, 6)
   Number of independent clones: $48.0 \times 10^6$
   Average size: 1.0-3.8 kb
   Number of different genes present: 5000-10000
3. Target carotenoid gene cDNA library
   Full length and normalised
   Directional cDNA cloning
   Library made by cloning each gene individually in 2 Evolva EVE 4, 5 & 8 vectors (FIGS. 4, 5, 6)
   Number of different genes: 48
   Species and genes used:
   Gentiana sp., ggps, psy, pds, zds, lcy-b, lcy-e, bhy, zep
   *Rhodobacter capsulatus*, idi, crtC, crtF
   *Erwinia uredovora*, crtE, crtB, crtI, crtY, crtZ
   *Nostoc anabaena*, zds
   *Synechococcus* PCC7942, pds
   *Erwinia herbicola*, crtE, crtB, crtI, crtY, crtZ
   *Staphylococcus aureus*, crtM, crtN
   *Xanthophyllomyces dendrorhous*, crtI, crtYb
   *Capsicum annuum*, ccs, crtL
   *Nicotiana tabacum*, crtL, bchy
   *Prochlorococcus* sp., lcy-b, lcy-e
   *Saccharomyces cerevisiae*, idi
   *Corynebacterium* sp., crtI, crtYe, crtYf, crtEb
   *Lycopersicon esculentum*, psy-1
   *Neurospora crassa*, al1

Example 5

Transformation of EVACs

Example 5a

Transformation

1. Inoculate a single colony into 100 ml YPD broth and grow with aeration at 30° C. to mid log, $2 \times 10^6$ to $2 \times 10^7$ cells/ml.
2. Spin to pellet cells at 400×g for 5 minutes; discard supernatant.
3. Resuspend cells in a total of 9 ml TE, pH 7.5. Spin to pellet cells and discard supernatant.
4. Gently resuspend cells in 5 ml 0.1 M Lithium/Cesium Acetate solution, pH 7.5.
5. Incubate at 30° C. for 1 hour with gentle shaking.
6. Spin at 400×g for 5 minutes to pellet cells and discard supernatant.
7. Gently resuspend in 1 ml TE, pH 7.5. Cells are now ready for transformation.
8. In a 1.5 ml tube combine:
   100 μl yeast cells
   5 μl Carrier DNA (10 mg/ml)
   5 μl Histamine Solution
   ⅕ of an EVAC preparation in a 10 μl volume (max). (One EVAC preparation is made of 100 μg of concatenation reaction mixture)
9. Gently mix and incubate at room temperature for 30 minutes.
10. In a separate tube, combine 0.8 ml 50% (w/v) PEG 4000 and 0.1 ml TE and 0.1 ml of 1 M LiAc for each transformation reaction. Add 1 ml of this PEG/TE/LiAc mix to each transformation reaction. Mix cells into solution with gentle pipetting.
11. Incubate at 30° C. for 1 hour.
12. Heat shock at 42° C. for 15 minutes; cool to 30° C.
13. Pellet cells in a microcentrifuge at high speed for 5 seconds and remove supernatant.
14. Resuspend in 200 μl of rich media and plate in appropriate selective media
15. Incubate at 30° C. for 48-72 hours until transformant colonies appear.

Example 5b

Transformation of EVACs using Electroporation 100 ml of YPD is inoculated with one yeast colony and grown to $OD_{600}=1.3$ to 1.5. The culture is harvested by centrifuging at 4000×g and 4° C. The cells are resuspended in 16 ml sterile $H_2O$. Add 2 ml 10×TE buffer, pH 7.5 and swirl to mix. Add 2 ml 10× lithium acetate solution (1 M, pH 7.5) and swirl to mix. Shake gently 45 min at 30° C. Add 1.0 ml 0.5 M DTE while swirling. Shake gently 15 min at 30° C. The yeast suspension is diluted to 100 ml with sterile water. The cells are washed and concentrated by centrifuging at 4000×g, resuspending the pellet in 50 ml ice-cold sterile water, centrifuging at 4000×g, resuspending the pellet in 5 ml ice-cold sterile water, centrifuging at 4000×g and resuspending the pellet in 0.1 ml ice-cold sterile 1 M sorbitol. The electroporation was done using a Bio-Rad Gene Pulser. In a sterile 1.5-ml microcentrifuge tube 40 μl concentrated yeast cells were mixed with 5 μl 1:10 diluted EVAC preparation. The yeast-DNA mix is transferred to an ice-cold 0.2-cm-gap disposable electroporation cuvette and pulsed at 1.5 kV, 25 μF, 200 Ω. 1 ml ice-cold 1 M sorbitol is added to the cuvette to recover the yeast. Aliquots are spread on selective plates containing 1 M sorbitol. Incubate at 30° C. until colonies appear.

Example 6

Rare Restriction Enzymes with Recognition Sequence and Cleavage Points

In this example, rare restriction enzymes are listed together with their recognition sequence and cleavage points. (^) indicates cleavage points 5'-3' sequence and (_) indicates cleavage points in the complementary sequence.

| 6a) | Unique, palindromic overhang |
|---|---|
| AscI | GG^CGCG_CC |
| AsiSI | GCG_AT^CGC |
| CciNI | GC^GGCC_GC |
| CspBI | GC^GGCC_GC |
| FseI | GG_CCGG^CC |
| MchAI | GC^GGCC_GC |
| NotI | GC^GGCC_GC |
| PacI | TTA_AT^TAA |
| SbfI | CC_TGCA^GG |
| SdaI | CC_TGCA^GG |
| SgfI | GCG_AT^CGC |
| SgrAI | CR^CCGG_YG |
| Sse232I | CG^CCGG_CG |
| Sse8387I | CC_TGCA^GG |
| 6b) | No overhang |
| BstRZ246I | ATTT^AAAT |
| BstSWI | ATTT^AAAT |
| MspSWI | ATTT^AAAT |
| MssI | GTTT^AAAC |
| PmeI | GTTT^AAAC |
| SmiI | ATTT^AAAT |
| SrfI | GCCC^GGGC |
| SwaI | ATTT^AAAT |
| 6c) | Non-palindromic and/or variable overhang |
| AarI | CACCTGCNNNN^NNNN_ (SEQ ID NO: 5) |
| AbeI | CC^TCA_GC |
| AloI | ^NNNNN_NNNNNNNGAACNNNNNNTCCNNNNNNN_NNNNN^ (SEQ ID NO: 6) |
| BaeI | ^NNNNN_NNNNNNNNNNACNNNNGTAYCNNNNNNN_NNNNN^ (SEQ ID NO: 7) |
| BbvCI | CC^TCA_GC |
| CpoI | CG^GWC_CG |
| CspI | CG^GWC_CG |
| Pfl27I | RG^GWC_CY |
| PpiI | ^NNNNN_NNNNNNNGAACNNNNNCTCNNNNNNN_NNNNN^ (SEQ ID NO: 8) |
| PpuMI | RG^GWC_CY |
| PpuXI | RG^GWC_CY |

| | -continued |
|---|---|
| Psp5II | RG^GWC_CY |
| PspPPI | RG^GWC_CY |
| RsrII | CG^GWC_CG |
| Rsr2I | CG^GWC_CG |
| SanDI | GG^GWC_CC |
| SapI | GCTCTTCN^NNN_ (SEQ ID NO: 9) |
| SdiI | GGCCN_NNN^NGGCC (SEQ ID NO: 10) |
| SexAI | A^CCWGG_T |
| SfiI | GGCCN_NNN^NGGCC (SEQ ID NO: 11) |
| Sse1825I | GG^GWC_CC |
| Sse8647I | AG^GWC_CT |
| VpaK32I | GCTCTTCN^NNN_ (SEQ ID NO: 12) |
| 6d) | Meganucleases |
| I-Sce I | TAGGGATAA_CAGG^GTAAT (SEQ ID NO: 13) |
| I-Ceu I | ACGGTC_CTAA^GGTAG (SEQ ID NO: 14) |
| I-Cre I | AAACGTC_GTGA^GACAGTTT (SEQ ID NO: 15) |
| I-Sce II | GGTC_ACCC^TGAAGTA (SEQ ID NO: 16) |
| I-Sce III | GTTTTGG_TAAC^TATTTAT (SEQ ID NO: 17) |
| Endo. Sce I | GATGCTGC_AGGC^ATAGGCTTGTTTA (SEQ ID NO: 18) |
| PI-Sce I | GG_GTGC^GGAGAA (SEQ ID NO: 19) |
| PI-Psp I | TGGCAAACAGCTA_TTAT^GGGTATTATGGGT (SEQ ID NO: 20) |
| I-Ppo I | CTCTC_TTAA^GGTAG (SEQ ID NO: 21) |
| HO | TTTCCGC_AACA^GT (SEQ ID NO: 22) |
| I-Tev I | NN_NN^NNTCAGTAGATGTTTTTCTTGGTCTACCGTTT (SEQ ID NO: 23) |

W = A or T;
N = A, C, G, or T

More meganucleases have been identified, but their precise sequence of recognition has not been determined, see e.g. www DOT meganuclease DOT com (URL inactivated in accordance with 37 CFR 1.57(d) by replacement of "." with "DOT".)

Example 7

Concatemer Size Limitation Experiments (Use of Stoppers)

Materials used:
pYAC4 (Sigma. Burke et al. 1987, science, vol 236, p 806) was digested w. EcoR1 and BamH1 and dephosphorylated pSE420 (invitrogen) was linearised using EcoR1 and used as the model fragment for concatenation.
T4 DNA ligase (Amersham-pharmacia biotech) was used for ligation according to manufacturers instructions.
Method: Fragments and arms were mixed in the ratios (concentrations are arbitrary units) indicated on FIGS. 9a and 9b. Ligation was allowed to proceed for 1 h at 16 C. Reaction was stopped by the addition of 1 μL 500 mM EDTA. Products were analysed by standard agarose GE (1% agarose, ½ strength TBE) or by PFGE (CHEF III, 1% LMP agarose, 2 strength TBE, angle 120, temperature 12 C, voltage 5.6 V/cm, switch time ramping 5-25 s, run time 30 h)

The results are shown in FIG. 9, wherein it is shown that the size of concatemers is proportional to the ratio of cassettes per YAC arms.

Example 8

Integration of Expression Cassettes into Artificial Chromosomes

Integration of expression cassettes into YAC12 was done essentially as done by Sears D. D., Hieter P., Simchen G., Genetics, 1994, 138, 1055-1065.

An AscI site was introduced into the Bgl II site of the integration vectors pGS534 and pGS525.

A β-galactosidase gene, as well as crtE, crtB, crtI and crtY from *Erwinia Uredovora* were cloned into pEVE4. These expression cassettes were ligated into AscI of the modified integration vectors pGS534 and pGS525.

Linearised pGS534 and pGS525 containing the expression cassettes were transformed into haploid yeast strains containing the appropriate target YAC which carries the Ade" gene. Red Ade-transformants were selected (the parent host strain is red due to the ade2-101 mutation).

Additional confirmation of correct integration of the β-galactosidase expression cassette was done using a β-galactosidase assay.

Example 9

Re-Transformation of Cells that Already Contain Artificial Chromosomes to Obtain at Least 2 Artificial Chromosomes Per Cell Yeast strains containing YAC12, Sears D. D., Hieter P., Simchen G., Genetics, 1994, 138, 1055-1065 were transformed with EVACs following the protocol described in example 4a. The transformed cells were plated on plates that select for cells that contained both YAC12 and EVACs.

Example 10

Example of Different Expression Patterns "Phenotypes" Obtained Using the Same Yeast Clones under Different Expression Conditions Colonies were picked with a sterile toothpick and streaked sequentially onto plates corresponding to the four repressed and/or induced conditions (−Ura/−Trp, −Ura/−Trp/−Met, −Ura/−Trp/+200 μM Cu$_2$SO$_4$, −Ura/−Trp/−Met/+200 μM Cu$_2$SO$_4$). 20 mg adenin was added to the media to suppress the ochre phenotype.

---

The invention claimed is:

1. A nucleotide concatemer comprising a cassette of nucleotide sequence of the general formula in the 5'→3' direction:

[rs$_2$-SP-PR-X-TR-SP-rs$_1$]$_n$ wherein
rs$_1$ and rs$_2$ together comprise a rare restriction site, denoted rs$_1$-rs$_2$, comprising a
recognition sequence of 7 to 30 non-N bases,
each SP individually denotes a spacer of at least two nucleotide bases,
PR denotes a promoter, capable of functioning in a cell,
X denotes an expressible nucleotide sequence,
TR denotes a terminator, and
n≧25, and
wherein at least a first cassette is different from a second cassette.

2. The concatemer according to claim 1, wherein the expressible nucleotide sequence comprises a DNA sequence selected from the group consisting of cDNA and genomic DNA.

3. The concatemer according to claim 1, wherein the rs$_1$-rs$_2$ restriction site of at least two cassettes are recognised by the same restriction enzyme.

4. A cell comprising at least one concatemer of individual oligonucleotide cassettes, each concatemer comprising an oligonucleotide of the following formula in 5'→3' direction:

[rs$_2$-SP-PR-X-TR-SP-rs$_1$]$_n$ wherein
rs$_1$ and rs$_2$ together comprise a rare restriction site, denoted rs$_1$-rs$_2$, comprising a
recognition sequence of 7 to 30 non-N bases,
each SP individually denotes a spacer of at least two nucleotide bases,
PR denotes a promoter, capable of functioning in the cell,
X denotes an expressible nucleotide sequence,
TR denotes a terminator, and
wherein n≧25, and
wherein at least two expressible nucleotide sequences are from different expression states.

5. A cell comprising at least one concatemer of individual oligonucleotide cassettes, each concatemer comprising an oligonucleotide of the following formula in 5'→3' direction:

[rs$_2$-SP-PR-X-TR-SP-rs$_1$]$_n$ wherein
rs$_1$ and rs$_2$ together comprise a rare restriction site, denoted rs$_1$-rs$_2$, comprising a
recognition sequence of 7 to 30 non-N bases,
each SP individually denotes a spacer of at least two nucleotide bases,
PR denotes a promoter, capable of functioning in the cell,
X denotes an expressible nucleotide sequence,
TR denotes a terminator, and
wherein n≧25, and
wherein rs$_1$-rs$_2$ in at least two cassettes is recognised by the same restriction enzyme.

6. The cell according to any one of claim 4 or 5, wherein substantially all rs$_1$-rs$_2$ sequences are recognised by the same restriction enzyme.

7. The cell according to any one of claim 4 or 5, being a yeast cell selected from the group consisting of baker's yeast, *Kluyveromyces marxianus, K. lactis, Candida utilis, Phaffia rhodozyma, Saccharomyces boulardii, Pichia pastoris, Hansenula polymorpha, Yarrowia lipolytica, Candida parafinica, Schwanniomyces castellii, Pichia stipitis, Candida shehatae, Rhodotorula glutinis, Lipomyces lipofer, Cryptococcus curvatus, Candida* spp., *Yarrowia lipolytica, Candida guilliermondii, Candida, Rhodotorula* spp., *Saccharomycopsis* spp., *Aureobasidiumpullulans, Candida brumptii, Candida hydrocarbofumarica, Torulopsis, Candida tropicalis, Saccharomyces cerevisiae, Rhodotorula rubra, Candida flav-*

*eri, Eremothecium ashbyii, Pichia* spp., *Kluyveromyces, Hansenula, Kloeckera, Pichia, Pachysolen* spp, and *Torulopsis bombicola*.

8. The cell according to claim 7, wherein at least a first cassette is different from a second cassette.

9. The concatemer according to claim 1, wherein said first cassette differs from said second cassette due to different expressible nucleotide sequences from materials of different expression states.

10. The concatemer according to claim 9, wherein the different expression states represent at least two different species.

11. The concatemer according to claim 9, wherein the different expression states represent at least two different kingdoms.

12. The concatemer according to claim 11, wherein said different expression states represent a eukaryotic species and a prokaryotic species.

13. The concatemer according to claim 1, wherein substantially all cassettes are different.

14. The concatemer of claim 1 wherein $rs_1$-$rs_2$ comprises a recognition sequence of at least 8 bases.

15. The concatemer according to claim 1, wherein the expressible nucleotide sequence is obtained through chemical synthesis.

16. The concatemer according to claim 1, wherein the recognition sequence is palindromic.

17. The cell according to claim 4, wherein the expressible nucleotide sequence is obtained through chemical synthesis.

18. The cell according to claim 4, wherein the recognition sequence is palindromic.

19. The cell according to claim 5, wherein the expressible nucleotide sequence is obtained through chemical synthesis.

20. The cell according to claim 5, wherein the recognition sequence is palindromic.

21. The concatemer according to claim 1, wherein n is at least 30, 75, 100, 200, 500, 750, 1000, 1500, or 2000.

22. The concatemer according to claim 1, wherein n is at least 30 to 60.

23. The cell according to any of claim 4 or 5, wherein n is at least 30, 75, 100, 200, 500, 750, 1000, 1500, or 2000.

24. The cell according to any of claim 4 or 5, wherein n is at least 30 to 60.

* * * * *

SEQUENCE LISTING

```
<160> NUMBER OF SEQ ID NOS: 23

<210> SEQ ID NO 1
<211> LENGTH: 3417
<212> TYPE: DNA
<213> ORGANISM: Artificial
<220> FEATURE:
<223> OTHER INFORMATION: Synthetic
<220> FEATURE:
<221> NAME/KEY: promoter
<222> LOCATION: (49)..(437)
<223> OTHER INFORMATION: Met25 promoter
<220> FEATURE:
<221> NAME/KEY: terminator
<222> LOCATION: (495)..(823)
<223> OTHER INFORMATION: ADH1
<220> FEATURE:
<221> NAME/KEY: rep_origin
<222> LOCATION: (959)..(1899)
<223> OTHER INFORMATION: ColE1
<220> FEATURE:
<221> NAME/KEY: misc_feature
<222> LOCATION: (1902)..(2759)
<223> OTHER INFORMATION: Ampicillin resistance gene
<220> FEATURE:
<221> NAME/KEY: misc_feature
<222> LOCATION: (2891)..(3347)
<223> OTHER INFORMATION: f1-phage origin of replication

<400> SEQUENCE: 1
ctgatttgcc cgggcagttc aggctcatca ggcgcgccat gcagggattc ttcggatgca      60
agggttcgaa tcccttagct ctcattattt tttgcttttt ctcttgaggt cacatgatcg     120
caaaatggca aatggcacgt gaagctgtcg atattgggga actgtggtgg ttggcaaatg     180
actaattaag ttagtcaagg cgccatcctc atgaaaactg tgtaacataa taaccgaagt     240
gtcgaaaagg tggcaccttg tccaattgaa cacgctcgat gaaaaaaata agatatatat     300
```

```
aaggttaagt aaagcgtctg ttagaaagga agttttttcct tttcttgct ctcttgtctt      360 ttcatctact atttccttcg tgtaatacag ggtcgtcaga tacatagata caattctatt      420 accccatcc atacaagctt ggcgccgaat tcgtcgaccc ggggatccgc ggccgcaggc       480
ctaaattgat ctagagcttt ggacttcttc gccagaggtt tggtcaagtc tccaatcaag     540
gttgtcggct tgtctacctt gccagaaatt tacgaaaaga tggaaaaggg tcaaatcgtt     600
ggtagatacg ttgttgacac ttctaaataa gcgaatttct tatgatttat gatttttatt     660
attaaataag ttataaaaaa ataagtgtta tacaaatttt aaagtgactc ttaggtttta     720
aaacgaaaat tcttgttctt gagtaactct ttcctgtagg tcaggttgct ttctcaggta     780
tagcatgagg tcgctcttat tgaccacacc tctaccggca tgcccatggg ttaactgatc     840
aatgcatcct gcatggcgcg cctgatgagc ctgaactgcc cggcaaatc agctggacgt      900 ctgcctgcat taatgaatcg gccaacgcgc ggggagaggc ggtttgcgta ttgggcgctc     960
ttccgcttcc tcgctcactg actcgctgcg ctcggtcgtt cggctgcggc gagcggtatc    1020
agctcactca aaggcggtaa tacggttatc cacagaatca ggggataacg caggaaagaa    1080
catgtgagca aaaggccagc aaaaggccag gaaccgtaaa aaggccgcgt tgctggcgtt    1140
tttccatagg ctccgccccc ctgacgagca tcacaaaaat cgacgctcaa gtcagaggtg    1200
gcgaaacccg acaggactat aaagatacca ggcgtttccc cctggaagct ccctcgtgcg    1260
ctctcctgtt ccgaccctgc cgcttaccgg atacctgtcc gcctttctcc cttcgggaag    1320
cgtggcgctt tctcatagct cacgctgtag gtatctcagt tcggtgtagg tcgttcgctc    1380
caagctgggc tgtgtgcacg aacccccgt tcagcccgac cgctgcgcct tatccggtaa    1440
ctatcgtctt gagtccaacc cggtaagaca cgacttatcg ccactggcag cagccactgg    1500
taacaggatt agcagagcga ggtatgtagg cggtgctaca gagttcttga agtggtggcc    1560
taactacggc tacactagaa ggacagtatt tggtatctgc gctctgctga gccagttac     1620 cttcggaaaa agagttggta gctcttgatc cggcaaacaa accaccgctg gtagcggtgg    1680
tttttttgtt tgcaagcagc agattacgcg cagaaaaaaa ggatctcaag aagatccttt    1740
gatcttttct acggggtctg acgctcagtg gaacgaaaac tcacgttaag ggattttggt    1800
catgagatta tcaaaaagga tcttcaccta gatcctttta aattaaaaat gaagttttaa    1860
atcaatctaa agtatatatg agtaaacttg gtctgacagt taccaatgct taatcagtga    1920
ggcacctatc tcagcgatct gtctatttcg ttcatccata gttgcctgac tccccgtcgt    1980
gtagataact acgatacggg agggcttacc atctggcccc agtgctgcaa tgataccgcg    2040
agacccacgc tcaccggctc cagatttatc agcaataaac cagccagccg aagggccga    2100 gcgcagaagt ggtcctgcaa ctttatccgc ctccatccag tctattaatt gttgccggga    2160
agctagagta agtagttcgc cagttaatag tttgcgcaac gttgttgcca ttgctacagg    2220
catcgtggtg tcacgctcgt cgtttggtat ggcttcattc agctccggtt cccaacgatc    2280
aaggcgagtt acatgatccc ccatgttgtg caaaaaagcg gttagctcct tcggtcctcc    2340
gatcgttgtc agaagtaagt tggccgcagt gttatcactc atggttatgg cagcactgca    2400
taattctctt actgtcatgc catccgtaag atgcttttct gtgactggtg agtactcaac    2460
caagtcattc tgagaatagt gtatgcggcg accgagttgc tcttgcccgg cgtcaatacg    2520
ggataatacc gcgccacata gcagaacttt aaaagtgctc atcattggaa aacgttcttc    2580
ggggcgaaaa ctctcaagga tcttaccgct gttgagatcc agttcgatgt aacccactcg    2640
tgcacccaac tgatcttcag catcttttac tttcaccagc gtttctgggt gagcaaaaac    2700
```

-continued

```
aggaaggcaa aatgccgcaa aaaagggaat aagggcgaca cggaaatgtt gaatactcat    2760
actcttcctt tttcaatatt attgaagcat ttatcagggt tattgtctca tgagcggata    2820
catatttgaa tgtatttaga aaaataaaca aatagggtt ccgcgcacat ttccccgaaa     2880
agtgccacct gacgcgccct gtagcggcgc attaagcgcg gcgggtgtgg tggttacgcg    2940
cagcgtgacc gctacacttg ccagcgccct agcgcccgct cctttcgctt tcttcccttc    3000
ctttctcgcc acgttcgccg gctttccccg tcaagctcta atcgggggc tcccttagg     3060 gttccgattt agtgctttac ggcacctcga ccccaaaaaa cttgattagg gtgatggttc    3120
acgtagtggg ccatcgccct gatagacggt ttttcgccct tgacgttgg agtccacgtt    3180 ctttaatagt ggactcttgt tccaaactgg aacaacactc aaccctatct cggtctattc    3240
ttttgattta taggattt tgccgatttc ggcctattgg ttaaaaaatg agctgattta      3300 acaaaatt aacgcgaatt ttaacaaaat attaacgctt acaatttcca ttcgccattc      3360
aggctgcgca actgttggga agggcgatcg gtgcgggcct cttcgctatt acgccag       3417
```

<210> SEQ ID NO 2
<211> LENGTH: 3501
<212> TYPE: DNA
<213> ORGANISM: Artificial
<220> FEATURE:
<223> OTHER INFORMATION: Synthetic
<220> FEATURE:
<221> NAME/KEY: promoter
<222> LOCATION: (49)..(519)
<223> OTHER INFORMATION: Cup1 promoter
<220> FEATURE:
<221> NAME/KEY: terminator
<222> LOCATION: (579)..(907)
<223> OTHER INFORMATION: ADH1
<220> FEATURE:
<221> NAME/KEY: rep_origin
<222> LOCATION: (1043)..(1983)
<223> OTHER INFORMATION: ColE1
<220> FEATURE:
<221> NAME/KEY: misc_feature
<222> LOCATION: (1986)..(2843)
<223> OTHER INFORMATION: Ampicillin resistance gene
<220> FEATURE:
<221> NAME/KEY: misc_feature
<222> LOCATION: (2975)..(3431)
<223> OTHER INFORMATION: f1-phage origin of replication

<400> SEQUENCE: 2

```
ctgatttgcc cgggcagttc aggctcatca ggcgcgccat gcagggataa gccgatccca      60
ttaccgacat ttgggcgcta tacgtgcata tgttcatgta tgtatctgta tttaaaacac     120
ttttgtatta ttttcctca tatatgtgta taggttata cggatgattt aattattact       180
tcaccaccct ttatttcagg ctgatatctt agccttgtta ctagttagaa aaagacattt     240
ttgctgtcag tcactgtcaa gagattcttt tgctggcatt tcttctagaa gcaaaaagag    300
cgatgcgtct tttccgctga accgttccag caaaaaagac taccaacgca atatggattg    360
tcagaatcat ataaaagaga agcaaataac tccttgtctt gtatcaattg cattataata    420
tcttcttgtt agtgcaatat catatagaag tcatcgaaat agatattaag aaaaacaaac    480
tgtacaatca atcaatcaat catcacataa aatgttcaaa gcttggcgcc gaattcgtcg    540
acccggggat ccgcggccgc aggcctaaat tgatctagag cttggacttc ttcgccaga     600 ggtttggtca agtctccaat caaggttgtc ggcttgtcta ccttgccaga aatttacgaa    660
aagatggaaa agggtcaaat cgttggtaga tacgttgttg acacttctaa ataagcgaat    720
ttcttatgat ttatgatttt tattattaaa taagttataa aaaaaataag tgtatacaaa    780
```

```
ttttaaagtg actcttaggt tttaaaacga aaattcttgt tcttgagtaa ctctttcctg    840
taggtcaggt tgctttctca ggtatagcat gaggtcgctc ttattgacca cacctctacc    900
ggcatgccca tgggttaact gatcaatgca tcctgcatgg cgcgcctgat gagcctgaac    960
tgcccgggca aatcagctgg acgtctgcct gcattaatga atcggccaac gcgcggggag   1020
aggcggtttg cgtattgggc gctcttccgc ttcctcgctc actgactcgc tgcgctcggt   1080
cgttcggctg cggcgagcgg tatcagctca ctcaaaggcg gtaatacggt tatccacaga   1140
atcaggggat aacgcaggaa agaacatgtg agcaaaaggc cagcaaaagg ccaggaaccg   1200
taaaaaggcc gcgttgctgg cgttttttcca taggctccgc ccccctgacg agcatcacaa   1260
aaatcgacgc tcaagtcaga ggtggcgaaa cccgacagga ctataaagat accaggcgtt   1320
tccccctgga agctccctcg tgcgctctcc tgttccgacc ctgccgctta ccggatacct   1380
gtccgccttt ctcccttcgg gaagcgtggc gctttctcat agctcacgct gtaggtatct   1440
cagttcggtg taggtcgttc gctccaagct gggctgtgtg cacgaacccc ccgttcagcc   1500
cgaccgctgc gccttatccg gtaactatcg tcttgagtcc aacccggtaa gacacgactt   1560
atcgccactg gcagcagcca ctggtaacag gattagcaga gcgaggtatg taggcggtgc   1620
tacagagttc ttgaagtggt ggcctaacta cggctacact agaaggacag tatttggtat   1680
ctgcgctctg ctgaagccag ttaccttcgg aaaaagagtt ggtagctctt gatccggcaa   1740
acaaaccacc gctggtagcg gtggtttttt tgtttgcaag cagcagatta cgcgcagaaa   1800
aaaaggatct caagaagatc ctttgatctt ttctacgggg tctgacgctc agtggaacga   1860
aaactcacgt taagggattt tggtcatgag attatcaaaa aggatcttca cctagatcct   1920
tttaaattaa aaatgaagtt ttaaatcaat ctaaagtata tatgagtaaa cttggtctga   1980
cagttaccaa tgcttaatca gtgaggcacc tatctcagcg atctgtctat ttcgttcatc   2040
catagttgcc tgactccccg tcgtgtagat aactacgata cgggagggct taccatctgg   2100
ccccagtgct gcaatgatac cgcgagaccc acgctcaccg gctccagatt tatcagcaat   2160
aaaccagcca gccggaaggg ccgagcgcag aagtggtcct gcaactttat ccgcctccat   2220
ccagtctatt aattgttgcc gggaagctag agtaagtagt tcgccagtta atagtttgcg   2280
caacgttgtt gccattgcta caggcatcgt ggtgtcacgc tcgtcgtttg gtatggcttc   2340
attcagctcc ggttcccaac gatcaaggcg agttacatga tcccccatgt tgtgcaaaaa   2400
agcggttagc tccttcggtc ctccgatcgt tgtcagaagt aagttggccg cagtgttatc   2460
actcatggtt atggcagcac tgcataattc tcttactgtc atgccatccg taagatgctt   2520
ttctgtgact ggtgagtact caaccaagtc attctgagaa tagtgtatgc ggcgaccgag   2580
ttgctcttgc ccggcgtcaa tacgggataa taccgcgcca catagcagaa ctttaaaagt   2640
gctcatcatt ggaaaacgtt cttcggggcg aaaactctca aggatcttac cgctgttgag   2700
atccagttcg atgtaaccca ctcgtgcacc caactgatct tcagcatctt ttactttcac   2760
cagcgtttct gggtgagcaa aaacaggaag gcaaaatgcc gcaaaaaagg gaataagggc   2820
gacacggaaa tgttgaatac tcatactctt ccttttttcaa tattattgaa gcatttatca   2880
gggttattgt ctcatgagcg gatacatatt tgaatgtatt tagaaaaata aacaaatagg   2940
ggttccgcgc acatttcccc gaaaagtgcc acctgacgcg ccctgtagcg cgcattaag    3000
cgcggcgggt gtggtggtta cgcgcagcgt gaccgctaca cttgccagcg ccctagcgcc   3060
cgctcctttc gctttcttcc cttcctttct cgccacgttc gccggctttc cccgtcaagc   3120
tctaaatcgg gggctccctt tagggttccg atttagtgct ttacggcacc tcgaccccaa   3180
```

-continued

| | |
|---|---|
| aaaacttgat taggggtgatg gttcacgtag tgggccatcg ccctgataga cggttttcg | 3240 |
| cccctttgacg ttggagtcca cgttctttaa tagtggactc ttgttccaaa ctggaacaac | 3300 |
| actcaaccct atctcggtct attcttttga tttataaggg attttgccga tttcggccta | 3360 |
| ttggttaaaa aatgagctga tttaacaaaa atttaacgcg aattttaaca aaatattaac | 3420 |
| gcttacaatt tccattcgcc attcaggctg cgcaactgtt gggaagggcg atcggtgcgg | 3480 |
| gcctcttcgc tattacgcca g | 3501 |

<210> SEQ ID NO 3
<211> LENGTH: 4188
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (49)..(574)
<223> OTHER INFORMATION: lambda spacer DNA (22428-22923)
<220> FEATURE:
<221> NAME/KEY: promoter
<222> LOCATION: (582)..(969)
<223> OTHER INFORMATION: Met25 promoter
<220> FEATURE:
<221> NAME/KEY: terminator
<222> LOCATION: (1027)..(1355)
<223> OTHER INFORMATION: ADH1
<220> FEATURE:
<221> NAME/KEY: misc_feature
<222> LOCATION: (1365)..(1603)
<223> OTHER INFORMATION: ARS1 (autonomous replicating sequence) for
    Yeast replication
<220> FEATURE:
<221> NAME/KEY: rep_origin
<222> LOCATION: (1730)..(2670)
<223> OTHER INFORMATION: ColE1
<220> FEATURE:
<221> NAME/KEY: misc_feature
<222> LOCATION: (2673)..(3530)
<223> OTHER INFORMATION: Ampicillin resistance gene
<220> FEATURE:
<221> NAME/KEY: misc_feature
<222> LOCATION: (3662)..(4118)
<223> OTHER INFORMATION: f1-phage origin of replication

<400> SEQUENCE: 3

| | |
|---|---|
| ctgatttgcc cgggcagttc aggctcatca ggcgcgccat gcagggattc tggaaattgc | 60 |
| aacgaaggaa gaaacctcgt tgctggaagc ctggaagaag tatcgggtgt tgctgaaccg | 120 |
| tgttgataca tcaactgcac ctgatattga gtggcctgct gtccctgtta tggagtaatc | 180 |
| gttttgtgat atgccgcaga aacgttgtat gaaataacgt tctgcggtta gttagtatat | 240 |
| tgtaaagctg agtattggtt tatttggcga ttattatctt caggagaata atggaagttc | 300 |
| tatgactcaa ttgttcatag tgtttacatc accgccaatt gcttttaaga ctgaacgcat | 360 |
| gaaatatggt ttttcgtcat gttttgagtc tgctgttgat atttctaaag tcggtttttt | 420 |
| ttcttcgttt tctctaacta ttttccatga aatacatttt tgattattat ttgaatcaat | 480 |
| tccaattacc tgaagtcttt catctataat tggcattgta tgtattggtt tattggagta | 540 |
| gatgcttgct tttctgagcc atagctctga tatcagatct tcttcggatg caagggttcg | 600 |
| aatcccttag ctctcattat tttttgcttt ttctcttgag gtcacatgat cgcaaaatgg | 660 |
| caaatggcac gtgaagctgt cgatattggg gaactgtggt ggttggcaaa tgactaatta | 720 |
| agttagtcaa ggcgccatcc tcatgaaaac tgtgtaacat aataaccgaa gtgtcgaaaa | 780 |
| ggtggcacct tgtccaattg aacacgctcg atgaaaaaaa taagatatat ataaggttaa | 840 |
| gtaaagcgtc tgttagaaag gaagtttttc cttttcttg ctctcttgtc ttttcatcta | 900 |

```
ctatttcctt cgtgtaatac agggtcgtca gatacataga tacaattcta ttaccccat      960
ccatacaagc ttggcgccga attcgtcgac ccggggatcc gcggccgcag gcctaaattg     1020
atctagagct ttggacttct tcgccagagg tttggtcaag tctccaatca aggttgtcgg     1080
cttgtctacc ttgccagaaa tttacgaaaa gatggaaaag ggtcaaatcg ttggtagata     1140
cgttgttgac acttctaaat aagcgaattt cttatgattt atgatttta ttattaaata      1200
agttataaaa aaataagtg tatacaaatt ttaaagtgac tcttaggttt taaaacgaaa      1260
attcttgttc ttgagtaact ctttcctgta ggtcaggttg ctttctcagg tatagcatga     1320
ggtcgctctt attgaccaca cctctaccgg catgcccatg ggttcttttg aaaagcaagc     1380
ataaaagatc taaacataaa atctgtaaaa taacaagatg taaagataat gctaaatcat     1440
ttggctttt gattgattgt acaggaaaat atacatcgca ggggttgac tttaccatt        1500
tcaccgcaat ggaatcaaac ttgttgaaga gaatgttcac aggcgcatac gctacaatga     1560
cccgattctt gctagccttt tctcggtctt gcaaacaacc gccaactgat caatgcatcc     1620
tgcatggcgc gcctgatgag cctgaactgc ccgggcaaat cagctggacg tctgcctgca     1680
ttaatgaatc ggccaacgcg cggggagagg cggtttgcgt attgggcgct cttccgcttc     1740
ctcgctcact gactcgctgc gctcggtcgt tcggctgcgg cgagcggtat cagctcactc     1800
aaaggcggta atacggttat ccacagaatc agggggataac gcaggaaaga acatgtgagc   1860
aaaaggccag caaaaggcca ggaaccgtaa aaaggccgcg ttgctggcgt ttttccatag     1920
gctccgcccc cctgacgagc atcacaaaaa tcgacgctca agtcagaggt ggcgaaaccc     1980
gacaggacta taaagatacc aggcgtttcc ccctggaagc tccctcgtgc gctctcctgt     2040
tccgaccctg ccgcttaccg gatacctgtc cgcctttctc ccttcgggaa gcgtggcgct    2100
ttctcatagc tcacgctgta ggtatctcag ttcggtgtag gtcgttcgct ccaagctggg    2160
ctgtgtgcac gaacccccg ttcagcccga ccgctgcgcc ttatccggta actatcgtct     2220
tgagtccaac ccggtaagac acgacttatc gccactggca gcagccactg gtaacaggat    2280
tagcagagcg aggtatgtag gcggtgctac agagttcttg aagtggtggc ctaactacgg    2340
ctacactaga aggacagtat ttggtatctg cgctctgctg aagccagtta ccttcggaaa    2400
aagagttggt agctcttgat ccggcaaaca aaccaccgct ggtagcggtg gtttttttgt    2460
ttgcaagcag cagattacgc gcagaaaaaa aggatctcaa gaagatcctt tgatcttttc    2520
tacggggtct gacgctcagt ggaacgaaaa ctcacgttaa gggattttgg tcatgagatt    2580
atcaaaaagg atcttcacct agatcctttt aaattaaaaa tgaagtttta aatcaatcta    2640
aagtatatat gagtaaactt ggtctgacag ttaccaatgc ttaatcagtg aggcaccta    2700
ctcagcgatc tgtctatttc gttcatccat agttgcctga ctccccgtcg tgtagataac    2760
tacgatacgg gagggcttac catctggccc cagtgctgca atgataccgc gagacccacg   2820
ctcaccggct ccagatttat cagcaataaa ccagccagcc ggaagggccg agcgcagaag   2880
tggtcctgca actttatccg cctccatcca gtctattaat tgttgccggg aagctagagt   2940
aagtagttcg ccagttaata gtttgcgcaa cgttgttgcc attgctacag gcatcgtggt   3000
gtcacgctcg tcgtttggta tggcttcatt cagctccggt tcccaacgat caaggcgagt   3060
tacatgatcc cccatgttgt gcaaaaaagc ggttagctcc ttcggtcctc cgatcgttgt   3120
cagaagtaag ttggccgcag tgttatcact catggttatg gcagcactgc ataattctct   3180
tactgtcatg ccatccgtaa gatgcttttc tgtgactggt gagtactcaa ccaagtcatt   3240
ctgagaatag tgtatgcggc gaccgagttg ctcttgcccg gcgtcaatac gggataatac   3300
```

```
cgcgccacat agcagaactt taaaagtgct catcattgga aaacgttctt cggggcgaaa    3360
actctcaagg atcttaccgc tgttgagatc cagttcgatg taacccactc gtgcacccaa    3420
ctgatcttca gcatctttta ctttcaccag cgtttctggg tgagcaaaaa caggaaggca    3480
aaatgccgca aaaagggaa taagggcgac acggaaatgt tgaatactca tactcttcct    3540
ttttcaatat tattgaagca tttatcaggg ttattgtctc atgagcggat acatatttga    3600
atgtatttag aaaaataaac aatagggggt tccgcgcaca tttccccgaa aagtgccacc    3660
tgacgcgccc tgtagcggcg cattaagcgc ggcgggtgtg gtggttacgc gcagcgtgac    3720
cgctacactt gccagcgccc tagcgcccgc tcctttcgct ttcttccctt cctttctcgc    3780
cacgttcgcc ggctttcccc gtcaagctct aaatcggggg ctccctttag ggttccgatt    3840
tagtgcttta cggcacctcg accccaaaaa acttgattag ggtgatggtt cacgtagtgg    3900
gccatcgccc tgatagacgg ttttcgccc tttgacgttg gagtccacgt tctttaatag    3960
tggactcttg ttccaaactg gaacaacact caacccatc tcggtctatt cttttgattt    4020
ataagggatt ttgccgattt cggcctattg gttaaaaaat gagctgattt aacaaaaatt    4080
taacgcgaat tttaacaaaa tattaacgct tacaatttcc attcgccatt caggctgcgc    4140
aactgttggg aagggcgatc ggtgcgggcc tcttcgctat tacgccag               4188
```

<210> SEQ ID NO 4
<211> LENGTH: 11466
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1962)..(2765)
<223> OTHER INFORMATION: URA3, orotidine-5'-phosphate decarboxylase
      coding sequence
<220> FEATURE:
<221> NAME/KEY: misc_feature
<222> LOCATION: (3560)..(4247)
<223> OTHER INFORMATION: Tetrahymena thermophila macronuclear telomere
<220> FEATURE:
<221> NAME/KEY: misc_feature
<222> LOCATION: (4893)..(5552)
<223> OTHER INFORMATION: HIS3, imidazoleglycerolphosphate dehydratase,
      coding sequence
<220> FEATURE:
<221> NAME/KEY: misc_feature
<222> LOCATION: (6024)..(6711)
<223> OTHER INFORMATION: Tetrahymena thermophila macronuclear telomere
<220> FEATURE:
<221> NAME/KEY: rep_origin
<222> LOCATION: (7198)..(7198)
<223> OTHER INFORMATION: Origin of replication, PMB1
<220> FEATURE:
<221> NAME/KEY: misc_feature
<222> LOCATION: (7956)..(8816)
<223> OTHER INFORMATION: AP(R), beta-lactamase, ampR ampicillin
      resistance, coding sequence
<220> FEATURE:
<221> NAME/KEY: misc_feature
<222> LOCATION: (9129)..(9803)
<223> OTHER INFORMATION: TRP1, phosphoribosylanthranilate isomerase,
      coding sequence
<220> FEATURE:
<221> NAME/KEY: misc_feature
<222> LOCATION: (9644)..(10388)
<223> OTHER INFORMATION: Autonomous replicating sequence
<220> FEATURE:
<221> NAME/KEY: misc_feature
<222> LOCATION: (10488)..(11465)
<223> OTHER INFORMATION: Centromere IV

<400> SEQUENCE: 4

```
ttctcatgtt tgacagctta tcatcgataa gctttaatgc ggtagtttat cacagttaaa      60
ttgctaacgc agtcaggcac cgtgtatgaa atctaacaat gcgctcatcg tcatcctcgg     120
caccgtcacc ctggatgctg taggcatagg cttggttatg ccggtactgc cgggcctctt     180
gcgggatatc gtccattccg acagcatcgc cagtcactat ggcgtgctgc tagcgctata     240
tgcgttgatg caatttctat gcgcacccgt tctcggagca ctgtccgacc gctttggccg     300
ccgcccagtc ctgctcgctt cgctacttgg agccactatc gactacgcga tcatggcgac     360
cacacccgtc ctgtggatca attcccttta gtataaattt cactctgaac catcttggaa     420
ggaccggtaa ttatttcaaa tctctttttc aattgtatat gtgttatgtt atgtagtata     480
ctctttcttc aacaattaaa tactctcggt agccaagttg gtttaaggcg caagacttta     540
atttatcact acggaattgg cgcgccaatt ccgtaatctt gagatcgggc gttcgatcgc     600
cccgggagat ttttttgttt tttatgtctt ccattcactt cccagacttg caagttgaaa     660
tatttctttc aagggaattg atcctctacg ccggacgcat cgtggccggc atcaccggcg     720
ccacaggtgc ggttgctggc gcctatatcg ccgacatcac cgatggggaa gatcgggctc     780
gccacttcgg gctcatgagc gcttgtttcg gcgtgggtat ggtggcaggc cccgtggccg     840
ggggactgtt gggcgccatc tccttgcatg caccattcct tgcggcggcg gtgctcaacg     900
gcctcaacct actactgggc tgcttcctaa tgcaggagtc gcataaggga gagcgtcgac     960
cgatgccctt gagagccttc aacccagtca gctccttccg gtgggcgcgg ggcatgacta    1020
tcgtcgccgc acttatgact gtcttcttta tcatgcaact cgtaggacag gtgccggcag    1080
cgctctgggt cattttcggc gaggaccgct ttcgctggag cgcgacgatg atcggcctgt    1140
cgcttgcggt attcggaatc ttgcacgccc tcgctcaagc cttcgtcact ggtcccgcca    1200
ccaaacgttt cggcgagaag caggccatta tcgccggcat ggcggccgac gcgctgggct    1260
acgtcttgct ggcgttcgcg acgcgaggct ggatggcctt ccccattatg attcttctcg    1320
cttccggcgg catcgggatg cccgcgttgc aggccatgct gtccaggcag gtagatgacg    1380
accatcaggg acagcttcaa ggatcgctcg cggctcttac cagcctaact tcgatcactg    1440
gaccgctgat cgtcacggcg atttatgccg cctcggcgag cacatggaac gggttggcat    1500
ggattgtagg cgccgcccta taccttgtct gcctccccgc gttgcgtcgc ggtgcatgga    1560
gccgggccac ctcgacctga atggaagccg gcggcacctc gctaacggat tcaccactcc    1620
aagaattgga gccaatcaat tcttgcggag aactgtgaat gcgcaaacca acccttggca    1680
gaacatatcc atcgcgtccg ccatctccag cagccgcacg cggcgcatcc ccccccccct    1740
ttcaattcaa ttcatcattt ttttttttatt ctttttttg atttcggttt ctttgaaatt    1800
tttttgattc ggtaatctcc gaacagaagg aagaacgaag gaaggagcac agacttagat    1860
tggtatatat acgcatatgt agtgttgaag aaacatgaaa ttgcccagta ttcttaaccc    1920
aactgcacag aacaaaaacc tgcaggaaac gaagataaat catgtcgaaa gctacatata    1980
aggaacgtgc tgctactcat cctagtcctg ttgctgccaa gctatttaat atcatgcacg    2040
aaaagcaaac aaacttgtgt gcttcattgg atgttcgtac caccaaggaa ttactggagt    2100
tagttgaagc attaggtccc aaaatttgtt tactaaaaac acatgtggat atcttgactg    2160
atttttccat ggagggcaca gttaagccgc taaaggcatt atccgccaag tacaattttt    2220
tactcttcga agacagaaaa tttgctgaca ttggtaatac agtcaaattg cagtactctg    2280
cgggtgtata cagaatagca gaatgggcag acattacgaa tgcacacggt gtggtgggcc    2340
caggtattgt tagcggtttg aagcaggcgg cagaagaagt aacaaaggaa cctagaggcc    2400
```

```
ttttgatgtt agcagaattg tcatgcaagg gctccctatc tactggagaa tatactaagg   2460
gtactgttga cattgcgaag agcgacaaag attttgttat cggctttatt gctcaaagag   2520
acatgggtgg aagagatgaa ggttacgatt ggttgattat gacacccggt gtgggtttag   2580
atgacaaggg agacgcattg ggtcaacagt atagaaccgt ggatgatgtg gtctctacag   2640
gatctgacat tattattgtt ggaagaggac tatttgcaaa gggaagggat gctaaggtag   2700
agggtgaacg ttacagaaaa gcaggctggg aagcatattt gagaagatgc ggccagcaaa   2760
actaaaaaac tgtattataa gtaaatgcat gtatactaaa ctcacaaatt agagcttcaa   2820
tttaattata tcagttatta ctcgggcgta atgatttta taatgacgaa aaaaaaaaaa   2880
ttggaaagaa aagggggggg gggcagcgtt gggtcctggc cacgggtgcg catgatcgtg   2940
ctcctgtcgt tgaggacccg gctaggctgg cggggttgcc ttactggtta gcagaatgaa   3000
tcaccgatac gcgagcgaac gtgaagcgac tgctgctgca aaacgtctgc gacctgagca   3060
acaacatgaa tggtcttcgg tttccgtgtt tcgtaaagtc tggaaacgcg gaagtcagcg   3120
ccctgcacca ttatgttccg gatctgcatc gcaggatgct gctggctacc ctgtggaaca   3180
cctacatctg tattaacgaa gcgctggcat tgacccgag tgattttct ctggtcccgc   3240
cgcatccata ccgccagttg tttaccctca caacgttcca gtaaccgggc atgttcatca   3300
tcagtaaccc gtatcgtgag catcctctct cgtttcatcg gtatcattac ccccatgaac   3360
agaaattccc ccttacacgg aggcatcaag tgaccaaaca ggaaaaaacc gcccttaaca   3420
tggcccgctt tatcagaagc cagacattaa cgcttctgga gaaactcaac gagctggacg   3480
cggatgaaca ggcagacatc tgtgaatcgc ttcacgacca cgctgatgag ctttaccgca   3540
gccctcgagg gataagcttc attttttagat aaaatttatt aatcatcatt aatttcttga   3600
aaaacatttt atttattgat cttttataac aaaaaacccct tctaaaagtt tattttttgaa   3660
tgaaaaactt ataaaaattt atgaaaacta caaaaaataa aatttttaat taaaataatt   3720
ttgataagaa cttcaatctt tgactagcta gcttagtcat ttttgagatt taattaatat   3780
tttatgttta ttcatatata aactattcaa aatattatag aatttaaaca ttttaacatc   3840
ttaatcattc ataaataact aaaaatcaaa gtattacatc aataaataac ttttactcaa   3900
tgtcaaagaa ttattggggt tggggttggg gttggggttg gggttggggt tggggttggg   3960
gttggggttg gggttggggt tggggttggg gttggggttg gggttggggt tggggttggg   4020
gttggggttg gggttggggt tggggttggg gttggggttg gggttggggt tggggttggg   4080
gttggggttg gggttggggt tggggttggg gttggggttg gggttggggt tggggttggg   4140
gttggggttg gggttggggt tggggttggg gttggggttg gggtgggaaa acagcattca   4200
ggtattagaa gaatatcctg attcaggtga aaatattgtt gatgcgcggg atcctcgggg   4260
acaccaaata tggcgatctc ggccttttcg tttcttggag ctgggacatg tttgccatcg   4320
atccatctac caccagaacg gccgttagat ctgctgccac cgttgtttcc accgaagaaa   4380
ccaccgttgc cgtaaccacc acgacggttg ttgctaaaga agctgccacc gccacggcca   4440
ccgttgtagc cgccgttgtt gttattgtag ttgctcatgt tatttctggc acttcttggt   4500
tttcctctta agtgaggagg aacataacca ttctcgttgt tgtcgttgat gcttaaattt   4560
tgcacttgtt cgctcagttc agccataata tgaaatgctt ttcttgttgt tcttacggaa   4620
taccacttgc cacctatcac cacaactaac ttttcccgt tcctccatct cttttatatt   4680
tttttctcg atcgagttca agagaaaaaa aagaaaaag caaaagaaa aaggaaagc   4740
gcgcctcgtt cagaatgaca cgtatagaat gatgcattac cttgtcatct tcagtatcat   4800
```

```
actgttcgta tacatactta ctgacattca taggtataca tatatacaca tgtatatata    4860
tcgtatgctg cagcttttaaa taatcggtgt cactacataa gaacaccttt ggtggaggga   4920
acatcgttgg taccattggg cgaggtggct tctcttatgg caaccgcaag agccttgaac   4980
gcactctcac tacggtgatg atcattcttg cctcgcagac aatcaacgtg gagggtaatt   5040
ctgctagcct ctgcaaagct ttcaagaaaa tgcgggatca tctcgcaaga gagatctcct   5100
actttctccc tttgcaaacc aagttcgaca actgcgtacg gcctgttcga aagatctacc   5160
accgctctgg aaagtgcctc atccaaaggc gcaaatcctg atccaaacct ttttactcca   5220
cgcgccagta gggcctcttt aaaagcttga ccgagagcaa tcccgcagtc ttcagtggtg   5280
tgatggtcgt ctatgtgtaa gtcaccaatg cactcaacga ttagcgacca gccggaatgc   5340
ttggccagag catgtatcat atggtccaga aaccctatac ctgtgtggac gttaatcact   5400
tgcgattgtg tggcctgttc tgctactgct tctgcctctt tttctgggaa gatcgagtgc   5460
tctatcgcta ggggaccacc ctttaaagag atcgcaatct gaatcttggt ttcatttgta   5520
atacgcttta ctagggcttt ctgctctgtc atctttgcct tcgtttatct tgcctgctca   5580
ttttttagta tattcttcga agaaatcaca ttactttata taatgtataa ttcattatgt   5640
gataatgcca atcgctaaga aaaaaaaga gtcatccgct aggtggaaaa aaaaaaatga    5700
aaatcattac cgaggcataa aaaaatatag agtgtactag aggaggccaa gagtaataga   5760 aaagaaaat tgcgggaaag gactgtgtta tgacttccct gactaatgcc gtgttcaaac    5820
gataactggc agtgactcct agcgctcacc aagctcttaa aacgagaatt aagaaaaagt   5880
cgtcatcttt cgataagttt ttcccacagc aaagcaatag tagaaaaaaa caatgggaaa   5940
cgttgaatga agacaaagcg tcgtggttta aaaggaaata cgctcacgta catgctaggg   6000
aacaggaccg tgcagcggat cccgcgcatc aacaatattt tcacctgaat caggatattc   6060
ttctaatacc tgaatgctgt tttcccaccc caaccccaac cccaaccca accccaaccc    6120 caaccccaac cccaaccca accccaaccc caaccccaac cccaaccca accccaaccc    6180 caaccccaac cccaaccca accccaaccc caaccccaac cccaaccca accccaaccc    6240 caaccccaac cccaaccca accccaaccc caaccccaac cccaaccca accccaaccc    6300 caaccccaac cccaaccca accccaaccc caaccccaac cccaaccca accccaataa    6360 ttctttgaca ttgagtaaaa gttatttatt gatgtaatac tttgatttt agttatttat    6420 gaatgattaa gatgttaaaa tgtttaaatt ctataatatt ttgaatagtt tatatatgaa   6480
taaacataaa atattaatta aatctcaaaa atgactaagc tagctagtca aagattgaag   6540
ttcttatcaa aattattta attaaaaatt ttatttttg tagttttcat aaattttat     6600 aagttttca ttcaaaaata aactttaga agggttttt gttataaaag atcaataaat      6660
aaaatgtttt tcaagaaatt aatgatgatt aataaatttt atctaaaaat gaagcttatc   6720
cctcgagggc tgcctcgcgc gtttcggtga tgacggtgaa aacctctgac acatgcagct   6780
cccggagacg gtcacagctt gtctgtaagc ggatgccggg agcagacaag cccgtcaggg   6840
cgcgtcagcg ggtgttggcg ggtgtcgggg cgcagccatg acccagtcac gtagcgatag   6900
cggagtgtat actggcttaa ctatgcggca tcagagcaga ttgtactgag agtgcaccat   6960
atgcggtgtg aaataccgca cagatgcgta aggagaaaat accgcatcag gcgctcttcc   7020
gcttcctcgc tcactgactc gctgcgctcg gtcgttcggc tgcggcgagc ggtatcagct   7080
cactcaaagg cggtaatacg gttatccaca gaatcagggg ataacgcagg aaagaacatg   7140
tgagcaaaag gccagcaaaa ggccaggaac cgtaaaaagg ccgcgttgct ggcgtttttc   7200
```

```
cataggctcc gccccctga cgagcatcac aaaaatcgac gctcaagtca gaggtggcga    7260
aacccgacag gactataaag ataccaggcg tttcccctg gaagctccct cgtgcgctct    7320
cctgttccga ccctgccgct taccggatac ctgtccgcct ttctcccttc gggaagcgtg    7380
gcgctttctc atagctcacg ctgtaggtat ctcagttcgg tgtaggtcgt tcgctccaag    7440
ctgggctgtg tgcacgaacc ccccgttcag cccgaccgct cgccttatc cggtaactat    7500 cgtcttgagt ccaacccggt aagacacgac ttatcgccac tggcagcagc cactggtaac    7560
aggattagca gagcgaggta tgtaggcggt gctacagagt tcttgaagtg gtggcctaac    7620
tacggctaca ctagaaggac agtatttggt atctgcgctc tgctgaagcc agttaccttc    7680 ggaaaagag ttggtagctc ttgatccggc aaacaaacca ccgctggtag cggtggtttt    7740
tttgtttgca agcagcagat tacgcgcaga aaaaaggat ctcaagaaga tcctttgatc    7800
ttttctacgg ggtctgacgc tcagtggaac gaaaactcac gttaagggat tttggtcatg    7860
agattatcaa aaaggatctt cacctagatc cttttaaatt aaaaatgaag ttttaaatca    7920
atctaaagta tatatgagta aacttggtct gacagttacc aatgcttaat cagtgaggca    7980
cctatctcag cgatctgtct atttcgttca tccatagttg cctgactccc cgtcgtgtag    8040
ataactacga tacgggaggg cttaccatct ggccccagtg ctgcaatgat accgcgagac    8100
ccacgctcac cggctccaga tttatcagca ataaaccagc cagccggaag ggccgagcgc    8160
agaagtggtc ctgcaacttt atccgcctcc atccagtcta ttaattgttg ccgggaagct    8220
agagtaagta gttcgccagt taatagtttg cgcaacgttg ttgccattgc tgcaggcatc    8280
gtggtgtcac gctcgtcgtt tggtatggct tcattcagct ccggttccca acgatcaagg    8340
cgagttacat gatccccat gttgtgcaaa aaagcggtta gctccttcgg tcctccgatc    8400
gttgtcagaa gtaagttggc cgcagtgtta tcactcatgg ttatggcagc actgcataat    8460
tctcttactg tcatgccatc cgtaagatgc ttttctgtga ctggtgagta ctcaaccaag    8520
tcattctgag aatagtgtat gcggcgaccg agttgctctt gcccggcgtc aacacgggat    8580
aataccgcgc cacatagcag aactttaaaa gtgctcatca ttggaaaacg ttcttcgggg    8640
cgaaaactct caaggatctt accgctgttg agatccagtt cgatgtaacc cactcgtgca    8700
cccaactgat cttcagcatc ttttactttc accagcgttt ctgggtgagc aaaaacagga    8760
aggcaaaatg ccgcaaaaaa gggaataagg gcgacacgga aatgttgaat actcatactc    8820 ttccttttc aatattattg aagcatttat cagggttatt gtctcatgag cggatacata    8880
tttgaatgta tttagaaaaa taaacaaata ggggttccgc gcacatttcc ccgaaaagtg    8940
ccacctgacg tctaagaaac cattattatc atgacattaa cctataaaaa taggcgtatc    9000
acgaggccct ttcgtcttca agaattaatt cggtcgaaaa agaaaagga gagggccaag    9060 agggaggca ttggtgacta ttgagcacgt gagtatacgt gattaagcac acaaaggcag    9120
cttggagtat gtctgttatt aatttcacag gtagttctgg tccattggtg aaagtttgcg    9180
gcttgcagag cacagaggcc gcagaatgtg ctctagattc cgatgctgac ttgctgggta    9240
ttatatgtgt gcccaataga aagagaacaa ttgacccggt tattgcaagg aaaatttcaa    9300
gtcttgtaaa agcatataaa aatagttcag gcactccgaa atacttggtt ggcgtgtttc    9360
gtaatcaacc taaggaggat gttttggctc tggtcaatga ttacggcatt gatatcgtcc    9420
aactgcatgg agatgagtcg tggcaagaat accaagagtt cctcggtttg ccagttatta    9480
aaagactcgt atttccaaaa gactgcaaca tactactcag tgcagcttca cagaaacctc    9540
attcgtttat tcccttgttt gattcagaag caggtgggac aggtgaactt ttggattgga    9600
```

```
actcgatttc tgactgggtt ggaaggcaag agagccccga aagcttacat tttatgttag    9660
ctggtggact gacgccagaa aatgttggtg atgcgcttag attaaatggc gttattggtg    9720
ttgatgtaag cggaggtgtg gagacaaatg gtgtaaaaga ctctaacaaa atagcaaatt    9780
tcgtcaaaaa tgctaagaaa taggttatta ctgagtagta tttatttaag tattgtttgt    9840
gcacttgcct gcaggccttt tgaaaagcaa gcataaaaga tctaaacata aaatctgtaa    9900
aataacaaga tgtaaagata atgctaaatc atttggcttt tgattgatt gtacaggaaa     9960 atatacatcg cagggggttg acttttacca tttcaccgca atggaatcaa acttgttgaa   10020
gagaatgttc acaggcgcat acgctacaat gacccgattc ttgctagcct tttctcggtc   10080
ttgcaaacaa ccgccggcag cttagtatat aaatacacat gtacatacct ctctccgtat   10140
cctcgtaatc attttcttgt atttatcgtc ttttcgctgt aaaaacttta tcacacttat   10200
ctcaaataca cttattaacc gcttttacta ttatcttcta cgctgacagt aatatcaaac   10260
agtgacacat attaaacaca gtggtttctt tgcataaaca ccatcagcct caagtcgtca   10320
agtaaagatt tcgtgttcat gcagatagat aacaatctat atgttgataa ttagcgttgc   10380
ctcatcaatg cgagatccgt ttaaccggac cctagtgcac ttaccccacg ttcggtccac   10440
tgtgtgccga acatgctcct tcactatttt aacatgtgga attaattcta aatcctcttt   10500
atatgatctg ccgatagata gttctaagtc attgaggttc atcaacaatt ggattttctg   10560
tttactcgac ttcaggtaaa tgaatgaga tgatacttgc ttatctcata gttaactcta    10620
agaggtgata cttatttact gtaaaactgt gacgataaaa ccggaaggaa gaataagaaa   10680
actcgaactg atctataatg cctatttcct gtaaagagtt taagctatga aagcctcggc   10740
attttggccg ctcctaggta gtgcttttt tccaaggaca aaacagtttc tttttcttga    10800
gcaggtttta tgtttcggta atcataaaca ataataaat tatttcattt atgtttaaaa    10860
ataaaaaata aaaagtatt ttaaattttt aaaaagttg attataagca tgtgacctttt    10920 tgcaagcaat taaattttgc aatttgtgat tttaggcaaa agttacaatt tctggctcgt   10980
gtaatatatg tatgctaaag tgaactttta caaagtcgat atggacttag tcaaaagaaa   11040
ttttcttaaa aatatatagc actagccaat ttagcacttc tttatgagat atattataga   11100
ctttattaag ccagatttgt gtattatatg tatttacccg gcgaatcatg gacatacatt   11160
ctgaaatagg taatattctc tatggtgaga cagcatagat aacctaggat acaagttaaa   11220
agctagtact gttttgcagt aatttttttc tttttttataa gaatgttacc acctaaataa    11280
gttataaagt caatagttaa gtttgatatt tgattgtaaa ataccgtaat atatttgcat   11340
gatcaaaagg ctcaatgttg actagccagc atgtcaacca ctatattgat caccgatata   11400
tggacttcca caccaactag taatatgaca ataaattcaa gatattcttc atgagaatgg   11460
cccaga                                                              11466
```

<210> SEQ ID NO 5
<211> LENGTH: 15
<212> TYPE: DNA
<213> ORGANISM: Artificial
<220> FEATURE:
<223> OTHER INFORMATION: AarI recognition site
<220> FEATURE:
<221> NAME/KEY: misc_feature
<222> LOCATION: (8)..(15)
<223> OTHER INFORMATION: n is a, c, g, or t

<400> SEQUENCE: 5
cacctgcnnn nnnnn                                                         15

```
<210> SEQ ID NO 6
<211> LENGTH: 37
<212> TYPE: DNA
<213> ORGANISM: Artificial
<220> FEATURE:
<223> OTHER INFORMATION: AloI recognition site
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (17)..(22)
<223> OTHER INFORMATION: n is a, c, g, or t
<220> FEATURE:
<221> NAME/KEY: misc_feature
<222> LOCATION: (26)..(37)
<223> OTHER INFORMATION: n is a, c, g, or t

<400> SEQUENCE: 6
nnnnnnnnnn nngaacnnnn nntcnnnnn nnnnnnn                              37

<210> SEQ ID NO 7
<211> LENGTH: 38
<212> TYPE: DNA
<213> ORGANISM: Artificial
<220> FEATURE:
<223> OTHER INFORMATION: BaeI recognition site
<220> FEATURE:
<221> NAME/KEY: misc_feature
<222> LOCATION: (1)..(15)
<223> OTHER INFORMATION: n is a, c, g, or t
<220> FEATURE:
<221> NAME/KEY: misc_feature
<222> LOCATION: (18)..(21)
<223> OTHER INFORMATION: n is a, c, g, or t
<220> FEATURE:
<221> NAME/KEY: misc_feature
<222> LOCATION: (27)..(38)
<223> OTHER INFORMATION: n is a, c, g, or t

<400> SEQUENCE: 7
nnnnnnnnnn nnnnnacnnn ngtaycnnnn nnnnnnn                             38

<210> SEQ ID NO 8
<211> LENGTH: 37
<212> TYPE: DNA
<213> ORGANISM: Artificial
<220> FEATURE:
<223> OTHER INFORMATION: PpiI recognition site
<220> FEATURE:
<221> NAME/KEY: misc_feature
<222> LOCATION: (1)..(12)
<223> OTHER INFORMATION: n is a, c, g, or t
<220> FEATURE:
<221> NAME/KEY: misc_feature
<222> LOCATION: (17)..(21)
<223> OTHER INFORMATION: n is a, c, g, or t
<220> FEATURE:
<221> NAME/KEY: misc_feature
<222> LOCATION: (25)..(37)
<223> OTHER INFORMATION: n is a, c, g, or t

<400> SEQUENCE: 8
nnnnnnnnnn nngaacnnnn nctcnnnnn nnnnnnn                              37

<210> SEQ ID NO 9
<211> LENGTH: 11
<212> TYPE: DNA
<213> ORGANISM: Artificial
<220> FEATURE:
<223> OTHER INFORMATION: SapI recognition site
```

```
<220> FEATURE:
<221> NAME/KEY: misc_feature
<222> LOCATION: (8)..(11)
<223> OTHER INFORMATION: n is a, c, g, or t

<400> SEQUENCE: 9
gctcttcnnn n                                                              11

<210> SEQ ID NO 10
<211> LENGTH: 13
<212> TYPE: DNA
<213> ORGANISM: Artificial
<220> FEATURE:
<223> OTHER INFORMATION: SdiI recognition site
<220> FEATURE:
<221> NAME/KEY: misc_feature
<222> LOCATION: (5)..(9)
<223> OTHER INFORMATION: n is a, c, g, or t

<400> SEQUENCE: 10
ggccnnnnng gcc                                                            13

<210> SEQ ID NO 11
<211> LENGTH: 13
<212> TYPE: DNA
<213> ORGANISM: Artificial
<220> FEATURE:
<223> OTHER INFORMATION: SfiI recognition site
<220> FEATURE:
<221> NAME/KEY: misc_feature
<222> LOCATION: (5)..(9)
<223> OTHER INFORMATION: n is a, c, g, or t

<400> SEQUENCE: 11
ggccnnnnng gcc                                                            13

<210> SEQ ID NO 12
<211> LENGTH: 11
<212> TYPE: DNA
<213> ORGANISM: Artificial
<220> FEATURE:
<223> OTHER INFORMATION: VpaK32I recognition site
<220> FEATURE:
<221> NAME/KEY: misc_feature
<222> LOCATION: (8)..(11)
<223> OTHER INFORMATION: n is a, c, g, or t

<400> SEQUENCE: 12
gctcttcnnn n                                                              11

<210> SEQ ID NO 13
<211> LENGTH: 18
<212> TYPE: DNA
<213> ORGANISM: Artificial
<220> FEATURE:
<223> OTHER INFORMATION: I-Sce I recognition site

<400> SEQUENCE: 13
tagggataac agggtaat                                                       18

<210> SEQ ID NO 14
<211> LENGTH: 15
<212> TYPE: DNA
<213> ORGANISM: Artificial
<220> FEATURE:
<223> OTHER INFORMATION: I-Ceu I recognition site

<400> SEQUENCE: 14
acggtcctaa ggtag                                                          15
```

```
<210> SEQ ID NO 15
<211> LENGTH: 19
<212> TYPE: DNA
<213> ORGANISM: Artificial
<220> FEATURE:
<223> OTHER INFORMATION: I-Cre I recognition site

<400> SEQUENCE: 15
aaacgtcgtg agacagttt                                              19

<210> SEQ ID NO 16
<211> LENGTH: 15
<212> TYPE: DNA
<213> ORGANISM: Artificial
<220> FEATURE:
<223> OTHER INFORMATION: I-Sce II recognition site

<400> SEQUENCE: 16
ggtcaccctg aagta                                                  15

<210> SEQ ID NO 17
<211> LENGTH: 18
<212> TYPE: DNA
<213> ORGANISM: Artificial
<220> FEATURE:
<223> OTHER INFORMATION: I-Sce III recognition site

<400> SEQUENCE: 17
gttttggtaa ctatttat                                               18

<210> SEQ ID NO 18
<211> LENGTH: 25
<212> TYPE: DNA
<213> ORGANISM: Artificial
<220> FEATURE:
<223> OTHER INFORMATION: Endo. Sce I recognition site

<400> SEQUENCE: 18
gatgctgcag gcataggctt gttta                                       25

<210> SEQ ID NO 19
<211> LENGTH: 12
<212> TYPE: DNA
<213> ORGANISM: Artificial
<220> FEATURE:
<223> OTHER INFORMATION: PI-Sce I recognition site

<400> SEQUENCE: 19
gggtgcggag aa                                                     12

<210> SEQ ID NO 20
<211> LENGTH: 30
<212> TYPE: DNA
<213> ORGANISM: Artificial
<220> FEATURE:
<223> OTHER INFORMATION: PI-Psp I recognition site

<400> SEQUENCE: 20
tggcaaacag ctattatggg tattatgggt                                  30

<210> SEQ ID NO 21
<211> LENGTH: 14
<212> TYPE: DNA
<213> ORGANISM: Artificial
<220> FEATURE:
<223> OTHER INFORMATION: I-Ppo I recognition site
```

```
<400> SEQUENCE: 21
ctctcttaag gtag                                                              14

<210> SEQ ID NO 22
<211> LENGTH: 13
<212> TYPE: DNA
<213> ORGANISM: Artificial
<220> FEATURE:
<223> OTHER INFORMATION: HO recognition site

<400> SEQUENCE: 22
tttccgcaac agt                                                               13

<210> SEQ ID NO 23
<211> LENGTH: 36
<212> TYPE: DNA
<213> ORGANISM: Artificial
<220> FEATURE:
<223> OTHER INFORMATION: I-Tev I recognition site
<220> FEATURE:
<221> NAME/KEY: misc_feature
<222> LOCATION: (1)..(6)
<223> OTHER INFORMATION: n is a, c, g, or t

<400> SEQUENCE: 23
nnnnnntcag tagatgtttt tcttggtcta ccgttt                                      36
```